United States Patent [19]

Yamada et al.

[11] Patent Number: 5,733,931
[45] Date of Patent: Mar. 31, 1998

[54] CYCLOHEXANEDIUREA DERIVATIVE AND PROCESS FOR ITS PRODUCTION

[75] Inventors: Toshihiro Yamada, Moriyama; Yoichi Nobuhara, Kusatsu; Ichinari Takagi, Koka-gun; Shiho Furumoto, Kyoto; Kazuhiro Kobayashi, Otsu; Kiyohito Ikemoto, Kusatsu, all of Japan

[73] Assignee: Nissin Food Products Co., Ltd., Osaka, Japan

[21] Appl. No.: 617,828

[22] PCT Filed: Sep. 7, 1994

[86] PCT No.: PCT/JP94/01475

§ 371 Date: Mar. 8, 1996

§ 102(e) Date: Mar. 8, 1996

[87] PCT Pub. No.: WO95/07258

PCT Pub. Date: Mar. 16, 1995

[30] Foreign Application Priority Data

Sep. 10, 1993 [JP] Japan ................. 5-226247

[51] Int. Cl.$^6$ ............................... A01N 47/28
[52] U.S. Cl. ................ 514/597; 514/308; 514/310; 514/313; 514/332; 514/352; 514/415; 514/471; 514/596; 546/140; 546/143; 546/162; 546/265; 546/309; 548/483; 549/472; 549/480; 564/48; 564/50; 564/305; 564/336
[58] Field of Search ...................... 514/308, 310, 514/313, 332, 352, 415, 471, 596, 597; 546/140, 143, 162, 265, 309; 548/483; 549/472, 480; 564/48, 50, 305, 336

[56] References Cited

U.S. PATENT DOCUMENTS 3,631,107  12/1971  Humber ................. 564/305
5,091,419  2/1992  Ito et al. ................. 514/596
5,166,429  11/1992  Ito et al. ................. 564/26
5,384,425  1/1995  Ito et al. ................. 560/138

FOREIGN PATENT DOCUMENTS 0325397  7/1989  European Pat. Off. .

OTHER PUBLICATIONS

Humber, L. G., J. Med. Chem. 1965, 8, pp. 401–404.

Primary Examiner—C. Warren Ivy
Assistant Examiner—Garth M. Dahlen
Attorney, Agent, or Firm—Sughrue, Mion, Zinn, Macpeak & Seas, PLLC

[57] ABSTRACT

The present invention provides a cyclohexanediurea derivative, inclusive of its salt, represented by the following formula (I):

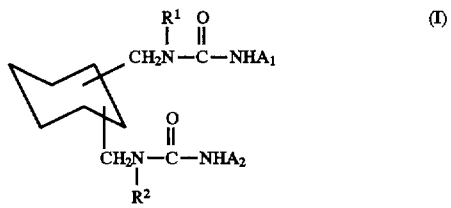

wherein $R^1$ and $R^2$ are the same or different and they each represent a straight-chain or branched alkyl group having at least 3 carbons, a cycloalkyl group, a cycloalkyl group having a bridge head, a furyl group, a furyl lower alkyl group or an aralkyl group, $A_1$ and $A_2$ are the same or different and they each represent a phenyl, pyridyl, quinolyl, isoquinolyl or indolyl group which may have substituents; a process for production thereof; an intermediate thereof; pharmaceutical use, a method for treatment and use thereof.

15 Claims, No Drawings

CYCLOHEXANEDIUREA DERIVATIVE AND PROCESS FOR ITS PRODUCTION

This application is a 371 of PCT/JP94/01475 filed Sep. 7, 1994.

TECHNICAL FIELD

The present invention relates to cyclohexanediurea derivatives which potently lower cholesterol and thus are useful as effective medicines for hyperlipidemia, atherosclerosis, etc.

BACKGROUND ART

Lipometabolism disorders in hyperlipidemia, atherosclerosis, etc. are considered as a risk factor which closely relates to cerebral apoplexy, myocardial infarction, etc. Recent research has shown that cholesterol is esterified before its intestinal absorption and that esterification of cholesterol is also necessary for its accumulation on the endarterium or in the liver. It has been further elucidated that the enzyme which catalyzes the esterification of cholesterol is Acyl-CoA: cholesterol acyltransferase (hereinafter referred to as "ACAT"). Since the compounds inhibiting the activities of ACAT can inhibit the esterification of cholesterol, they are expected to prevent intestinal absorption of cholesterol or cholesterol accumulation on the endarterium and considered as very potential medicines for hyperlipidemia and atherosclerosis and various diseases caused by them. Conventional ACAT enzyme inhibitors can be classified based on the chemical structure into three groups: amido derivatives (Japanese Unexamined Patent Publications Nos. 23848/1988 and 278038/1990), urea derivatives (Japanese Unexamined Patent Publications Nos. 6455/1990, 294256/1991 and 220168/1991) and diurea derivatives (Japanese Unexamined Patent Publications Nos. 203360/1989 and 117651/1990). There has been no report of the diurea compound in which urea groups are linked to a cyclohexane ring through alkylene chains, which is the chemical structure according to the present invention.

In search of a new ACAT enzyme inhibitor more powerful than those of the prior art and effective as a medicine for hyperlipidemia, atherosclerosis, etc., the inventors of the present invention studied 1,2-, 1,3- and 1,4-positions on the cyclohexane ring and cis- or trans- isomers of diurea compounds in these positions and finally found that some isomers of cyclohexanediurea derivatives in specific positions are the compounds which fulfill the above-mentioned requirements. The present invention has been accomplished based on this finding.

DISCLOSURE OF THE INVENTION

The present invention provides a cyclohexanediurea derivative represented by the following formula (I):

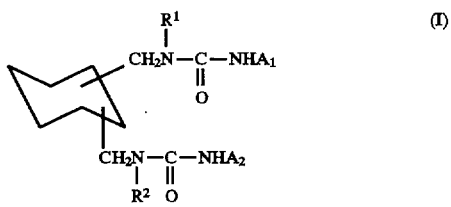

wherein $R^1$ and $R^2$ are the same or different and they each represent a straight-chain or branched alkyl group having at least 3 carbons, a cycloalkyl group, a cycloalkyl group having a bridge head, a furyl group, a furyl lower alkyl or an aralkyl group and $A_1$ and $A_2$ are the same or different and they each represent a phenyl, pyridyl, quinolyl, isoquinolyl or indolyl group which may have substituent(s); or a salt thereof.

The present invention also provides a cyclohexanediamine derivative represented by the following formula (II):

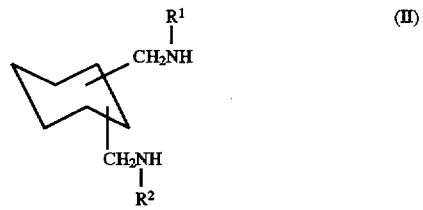

wherein $R^1$ and $R^2$ are as defined above; or a salt thereof.

The present invention further provides an ACAT enzyme inhibitor which comprises an effective amount of the cyclohexanediurea derivative of formula (I) or its salt and a pharmaceutically acceptable carrier.

The present invention also provides a medicine for hyperlipidemia which comprises an effective amount of the cyclohexanediurea derivative of formula (I) or its salt and a pharmaceutically acceptable carrier.

The present invention further provides a medicine for atherosclerosis which comprises an effective amount of the cyclohexanediurea derivative of formula (I) or its salt and a pharmaceutically acceptable carrier.

Furthermore, the present invention provides a method for inhibiting an ACAT enzyme which comprises administering an effective amount of the cyclohexanediurea derivative of formula (I) or its salt to a patient.

The present invention also provides a method for treating hyperlipidemia which comprises administering an effective amount of the cyclohexanediurea derivative of formula (I) or its salt to a patient.

The present invention also provides a method for treating atherosclerosis which comprises administering an effective amount of the cyclohexanediurea derivative of formula (I) or its salt to a patient.

Furthermore, the present invention provides use of the cyclohexanediurea derivative of formula (I) or its salt in inhibition of ACAT enzyme.

The present invention also provides use of the cyclohexanediurea derivative of formula (I) or its salt in treatment of hyperlipidemia.

The present invention further provides use of the cyclohexanediurea derivative of formula (I) or its salt in treatment of atherosclerosis.

Furthermore, the present invention provides use of the cyclohexanediurea derivative of formula (I) or its salt in preparation of an ACAT enzyme inhibitor.

The present invention also provides use of the cyclohexanediurea derivative of formula (I) or its salt in preparation of a medicine for hyperlipidemia.

The present invention also provides use of the cyclohexanediurea derivative of formula (I) or its salt in preparation of a medicine for atherosclerosis.

The present invention also provides a process for preparing the cyclohexanediurea derivative of formula (I):

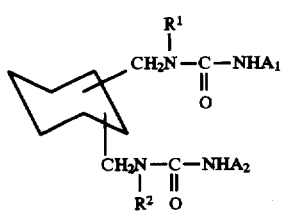
(I)

wherein $R^1$, $R^2$, $A_1$ and $A_2$ are as defined above, in accordance with one of the following <Process A> to <Process D>:

<Process A>

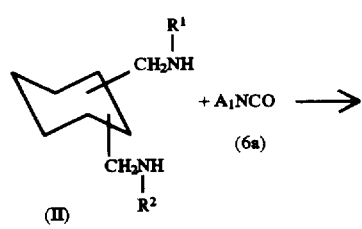
(II)
+ $A_1NCO$ (6a) →

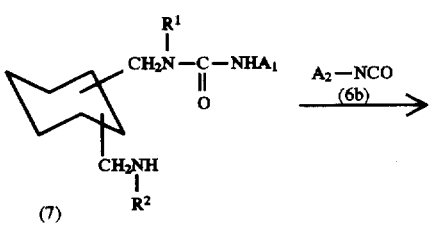
(7)
$A_2$—NCO (6b) →

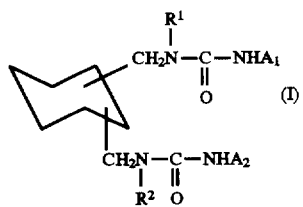
(I)

wherein $R^1$, $R^2$, $A_1$ and $A_2$ are as defined above,

<Process B>

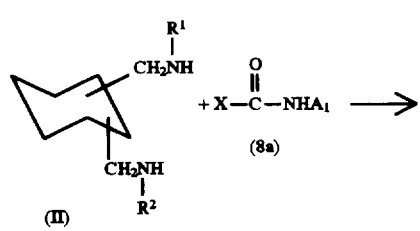
(II)
+ X—C(=O)—NHA$_1$ (8a) →

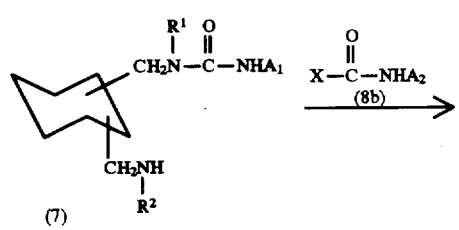
(7)
X—C(=O)—NHA$_2$ (8b) →

-continued
<Process B>

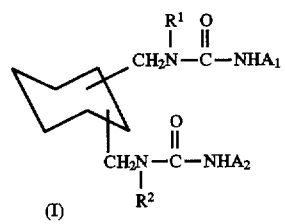
(I)

wherein $R^1$, $R^2$, $A_1$ and $A_2$ are as defined above,

<Process C>

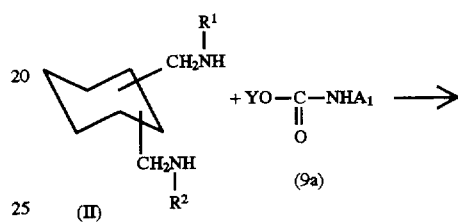
(II)
+ YO—C(=O)—NHA$_1$ (9a) →

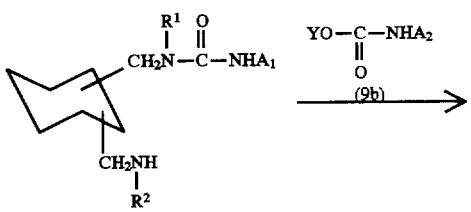
YO—C(=O)—NHA$_2$ (9b) →

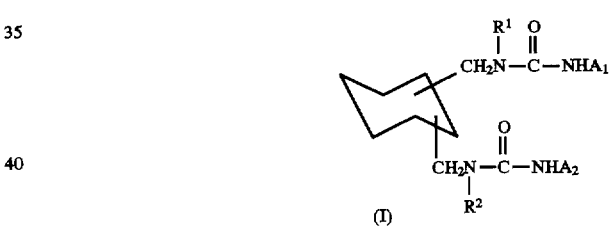
(I)

wherein $R^1$, $R^2$, $A_1$ and $A_2$ defined above, and

<Process D>

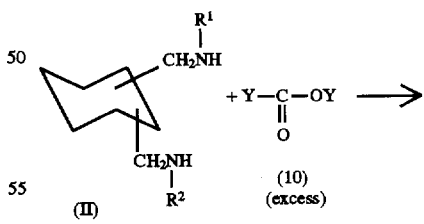
(II)
+ Y—C(=O)—OY (10) (excess) →

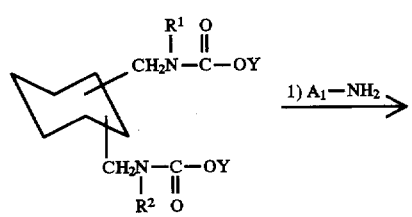
(11)
1) $A_1$—NH$_2$ →

-continued
<Process D>

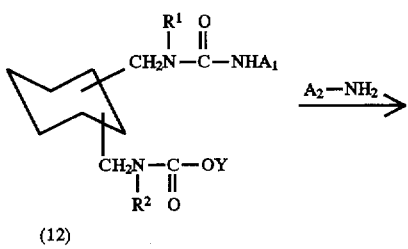

(12)

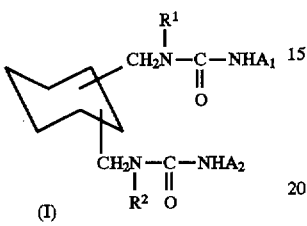

(I)

wherein $R^1$, $R^2$, $A_1$ and $A_2$ are as defined above.

The cyclohexanediurea derivative (II) synthetic intermediate for preparation of the cyclohexanediurea derivative of formula (I) or its salt.

The present invention will be described below in detail. The compound (I) of the invention has such a structure that two urea derivatives are linked to a cyclohexane ring through methylene chains, and includes a trans-1,2, cis-1,2, trans-1,3, cis-1,3, trans-1,4 or cis-1,4 cyclohexanediurea derivative, which varies depending on how the urea derivatives are linked. The compound (I) of the present invention preferably has trans-1,4, cis-1,4, or cis-1,3 bond. The cyclohexane ring may be chair or boat form.

In the definition of the formula (I), "the straight-chain or branched alkyl group having at least 3 carbon atoms" includes a $C_{3-10}$ straight-chain or branched alkyl group, such as propyl, isopropyl, butyl, isobutyl, sec-butyl, tert-butyl, pentyl, isopentyl, tert-pentyl, neopentyl, hexyl, 1,3-dimethylbutyl, 3,3-dimethylbutyl, heptyl, 1-methylheptyl, 1-methylhexyl, 2-methylhexyl, 1-ethylpentyl, 1,1-dimetylpentyl, 1,2-dimethylpentyl, octyl, 1,5-dimethylhexyl, tert-octyl, nonyl, decyl and so on.

"The cycloalkyl group" includes a $C_{3-10}$ cycloalkyl group which may have a $C_{1-4}$ lower alkyl group, such as cyclopropyl, cyclobutyl, cyclopentyl, cyclohexyl, 2-methylcyclohexyl, 3-methylcyclohexyl, 4-methylcyclohexyl, 4-ethylcyclohexyl, 4-propylcyclohexyl, 4-butylcyclohexyl, cycloheptyl, cyclooctyl, cyclononyl, cyclodecyl and so on.

"The cycloalkyl group which has a bridge head" includes adamantyl, norbornyl and so on.

"The furyl group" includes 2-furyl, 3-furyl and so on.

"The furyl lower alkyl group" includes furylmethyl, furylethyl, furylpropyl, furylisopropyl, furylbutyl, furylisobutyl, furyl sec-butyl, furyl tert-butyl, furylpentyl, furylisopentyl, furyl tert-pentyl, furylneopentyl and so on.

The substituent of "the phenyl, pyridyl, isoquinolyl, quinolyl or indolyl group which may have substituent(s)" includes a $C_{1-5}$ lower alkyl group, a cyclic amino group, a mono(lower)alkylamino group, a di(lower)alkylamino group having the same or different alkyl groups, a hydroxyl group, a lower alkoxy group, a lower alkoxycarbonyl group, a lower alkoxycarbonyloxy group, a cyano group, a nitro group, a halogen atom, a lower alkylcarbonyloxy group, a trihalogenomethyl group, and an acylamino group.

Among the substituents, the $C_{1-5}$ lower alkyl group includes a straight-chain or branched alkyl group such as methyl, ethyl, propyl, isopropyl, butyl, isobutyl, sec-butyl, tert-butyl, pentyl, tert-pentyl and neopentyl. The cyclic amino group includes pyrrolidino, piperidino, morpholino, piperazino, homopiperazino and so on. The mono(lower)alkylamino group and the di(lower)alkylamino group having the same or different alkyl groups include an amino group substituted by one or two $C_{1-5}$ lower alkyl groups mentioned above. The lower alkoxy group includes a $C_{1-5}$ alkoxy group such as methoxy, ethoxy, propoxy, isopropyl, butoxy, sec-butoxy, tert-butoxy, pentoxy, sec-pentoxy, tert-pentoxy and so on. The lower alkoxycarbonyl group includes a $C_{2-6}$ alkoxycarbonyl group such as methoxycarbonyl, ethoxycarbonyl, propoxycarbonyl, isopropoxycarbonyl, butoxycarbonyl, sec-butoxycarbonyl, tert-butoxycarbonyl, pentoxycarbonyl, sec-pentoxycarbonyl, tert-pentoxycarbonyl and so on. The lower alkoxycarbonyloxy group includes methoxycarbonyloxy, ethoxycarbonyloxy, propoxycarbonyloxy, isopropoxycarbonyloxy, butoxycarbonyloxy, sec-butoxycarbonyloxy, tert-butoxycarbonyloxy, pentoxycarbonyloxy, sec-pentoxycarbonyloxy, tert-pentoxycarbonyloxy and so on. The halogen atom includes fluorine, chlorine, bromine and iodine. The lower alkylcarbonyloxy group includes a $C_{2-6}$ alkylcarbonyloxy group such as methylcarbonyloxy, ethylcarbonyloxy, propylcarbonyloxy, isopropylcarbonyloxy, butylcarbonyloxy, sec-butylcarbonyloxy, tert-butylcarbonyloxy, pentylcarbonyloxy, sec-pentylcarbonyloxy, tert-pentylcarbonyloxy and so on. The trihalogenomethyl group includes trifluoromethyl, trichloromethyl and so on. The acylamino group includes a $C_{2-5}$ acylamino group such as acetylamino, propionylamino, isopropionylamino, butyrylamino, isobutyrylamino, valerylamino, isovalerylamino, pivaloylamino and so on.

The phenyl, pyridyl, quinolyl, isoquinolyl or indolyl group represented by A may have one or more substituents mentioned above. Examples of such phenyl groups are 3-dimethylaminophenyl, 4-dimethylaminophenyl, 4-ethylmethylaminophenyl, 4-dietylaminophenyl, and 4-piperidinophenyl.

The said phenyl (2–6 positions), pyridyl (2–6 positions), quinolyl (2–8 positions), isoquinolyl (1, 3–8 positions) or indolyl (2–7 positions) may be linked to the amino group of urea in any of these positions.

Preferred species of the compound of formula (I) are as follows:

I. a cyclohexanediurea derivative of formula (I) wherein the urea derivatives are linked to the cyclohexane ring by trans-1,4, cis-1,4 or cis-1,3 bond, and $R^1$ or $R^2$ represents a cycloalkyl group or a branched alkyl group; and $A_1$ or $A_2$ represents 4-dimethylaminophenyl, 4-pyrrolidinophenyl or 4-piperidinophenyl; or a salt thereof;

II. a cyclohexanediurea derivative of formula (I) wherein $R^1=R^2$ and $A_1=A_2$; or a salt thereof;

III. a cyclohexanediurea derivative of formula (I) wherein $R^1$ and $R^2$ are the same or different and they each represent cyclopentyl, cyclohexyl, cycloheptyl or 4-methylcyclohexyl; or a salt thereof;

IV. a cyclohexanediurea derivative of formula (I) wherein $A_1$ and $A_2$ are the same or different and they each represent 4-dimethylaminophenyl, 4-diethylaminophenyl, 4-pyrrolidinophenyl, 4-piperidinophenyl or 4-morpholinophenyl; or a salt thereof; and V. a cyclohexanediurea derivative or salt thereof which is one of the compounds or salts given below in (1)–(10):

(1) a trans-1,4-bis[[1-cyclopentyl-3-(4-dimethylaminophenyl)ureido]methyl]cyclohexane or a salt thereof;

(2) a trans-1,4-bis[[1-cyclohexyl-3-(4-dimethylaminophenyl)ureido]methyl]cyclohexane or a salt thereof;

(3) a trans-1,4-bis[[1-cyclohexyl-3-(4-diethylaminophenyl)ureido]methyl]cyclohexane or a salt thereof;

(4) a trans-1,4-bis[[1-cyclohexyl-3-(4-pyrrolidinophenyl)ureido]methyl]cyclohexane or a salt thereof;

(5) a trans-1,4-bis[[1-cyclohexyl-3-(4-piperidinophenyl)ureido]methyl]cyclohexane or a salt thereof;

(6) a trans-1,4-bis[[3-(4-dimethylaminophenyl)-1-(4-methylcyclohexyl)ureido]methyl]cyclohexane or a salt thereof;

(7) a trans-1,4-bis[[1-cycloheptyl-3-(4-dimethylaminophenyl)ureido]methyl]cyclohexane or a salt thereof;

(8) a trans-1,4-bis[[1-cycloheptyl-3-(4-diethylaminophenyl)ureido]methyl]cyclohexane or a salt thereof;

(9) a trans-1,4-bis[[1-cycloheptyl-3-(4-pyrrolidinophenyl)ureido]methyl]cyclohexane or a salt thereof; and

(10) a trans-1,4-bis[[1-cycloheptyl-3-(4-piperidinophenyl)ureido]methyl]cyclohexane or a salt thereof.

The compounds of formula (I) can also be formed into salts. Acid addition salts of the compound (I) are included in the present invention. The acid used to form such salts includes mineral acids and organic acids such as hydrochloric acid, hydrobromic acid, sulfuric acid, nitric acid, phosphoric acid, acetic acid, citric acid, succinic acid, oxalic acid, fumaric acid, maleic acid, malic acid, tartaric acid, methanesulfonic acid, ethanesulfonic acid, p-toluenesulfonic acid and so on. The salts can be produced by reacting these acids with the compound of formula (I) by conventional methods.

The compound of the invention can be prepared by various methods and there is no specific limitation on the method. The compound can be prepared, for example, by the following <Reaction scheme A>.

<Reaction scheme A>

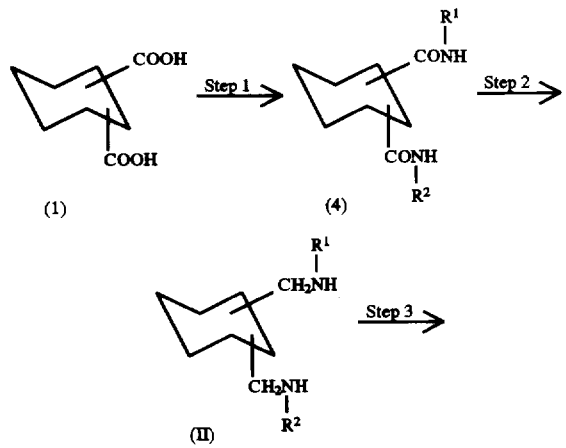

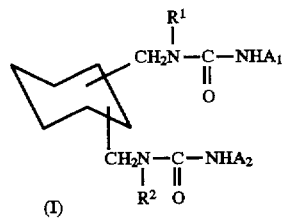

wherein $R^1$, $R^2$, $A_1$ and $A_2$ are as defined above.
<Step 1> to <Step 3> are described below.

<Step 1>

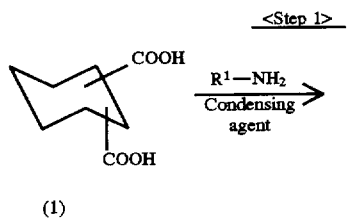

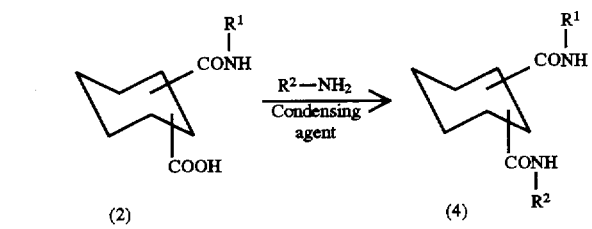

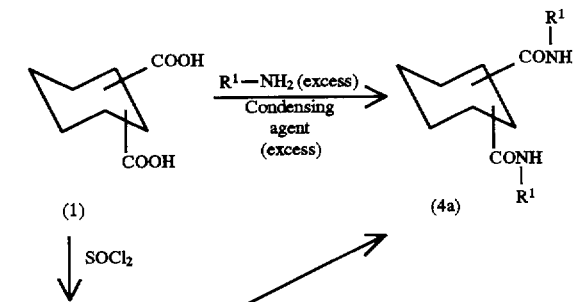

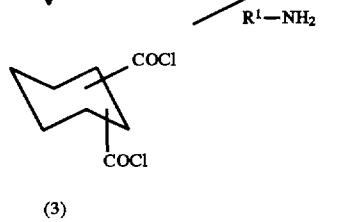

wherein $R^1$ and $R^2$ are as defined above.

The cyclohexanedicarbonic acid of formula (1) (which is a cis or trans, 1,2-, 1,3-, or 1,4-isomer) is reacted with a primary amine derivative represented by $R^1NH_2$ in the presence of a condensing agent to give a monoamide (2). The monoamide (2) is reacted with a primary amine derivative represented by $R^2NH_2$ in the presence of a condensing agent to give a diamide of formula (4).

The reaction between cyclohexanedicarbonic acid and $R^1NH_2$ is carried out using about 0.9–1.1 moles of $R^1NH_2$ and about 1.0–1.1 moles of a condensing agent per mole of cyclohexanedicarbonic acid in a solvent under cooling or at room temperature for about 1–5 hours. Examples of useful solvents are benzene, toluene, tetrahydrofuran (THF), dimethylformamide (DMF), dimethyl sulfoxide (DMSO), etc.

Examples of useful condensing agents are N,N'-dicyclohexylcarbodiimide (DCC), 1-ethyl-3-(3-dimethylaminopropyl)carbodiimide hydrochloride acid salt (WSCD.HCl), carbonyldiimidazole, etc. A reaction promoter such as triethylamine, 1-hydroxybenzotriazole (HOBt) and N-hydroxysuccinimido can also be added in the reaction. The reaction mixture containing the starting dicarbonic acid, object monoamide (2) and diamide is subjected to separation and purification by a conventional method such as recrystallization, column chromatography or extraction with a solvent, thus giving an object monoamide (2).

The monoamide (2) is then reacted with $R^2NH_2$ in the presence of a condensing agent under the same conditions as mentioned above, thus giving a diamide (4).

The diamide (4) wherein $R^1=R^2$ can be prepared by reacting cyclohexanecarbonic acid with an excess (at least 2 equivalents) of $R^1NH_2$ and a condensing agent in the same manner as mentioned above.

The diamide (4a) wherein $R^1=R^2$ can also be prepared by reacting cyclohexanedicarbonic acid (1) with a chlorizing agent such as thionylchloride and oxazalylchloride under cooling or at room temperature in the absence of a solvent or in a solvent inert to the reaction, such as benzene, toluene, hexane, dichloromethane and chloroform, thus converting cyclohexanedicarbonic acid into an acid chloride derivative of formula (3) and then allowing the derivative to react in an inert solvent such as benzene, toluene, hexane, dichloromethane, chloroform, THF, DMF and DMSO under ice-cooling or at room temperature, optionally using an inorganic base such as sodium carbonate, potassium carbonate and sodium hydrogencarbonate or an organic base such as triethylamine and pyridine to promote the reaction. The amine derivative represented by $R^1NH_2$ is usually used in an amount of 2 moles to an excess mole per mole of dicarbonic acid.

The diamide (4a) wherein $R^1=R^2$ can also be obtained by using at least 2 equivalents of an amine represented by $R^1NH_2$ and an condensing agent relative to the dicarbonic acid (1).

<Step 2>

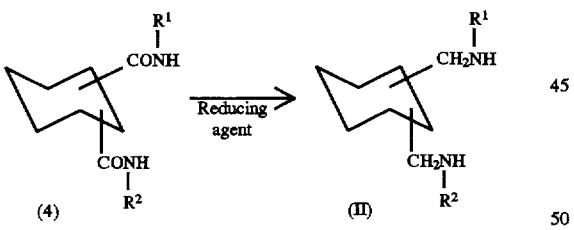

wherein $R^1$ and $R^2$ are as defined above.

Step 2 is a reduction reaction of carbonyl groups of the diamide derivative of formula (4). In step 2, a diamide derivative of formula (4) is reacted in a solvent in the presence of a reducing agent, thus giving a reductant (II). The reaction is carried out using an equimolar to excess amount of the reducing agent relative to the diamide (4) at room temperature to about 100° C. for about 2–24 hours.

Examples of useful solvents in the reduction reaction include solvents inert to the reaction, such as benzene, toluene, dioxane THF, ether, and the like, among which THF is preferred. Examples of useful reducing agents include lithiumaluminum hydride (LAH), diisobutylaluminum hydride, sodium dihydro-bis(2-methoxyethoxy)aluminate, diborane, borantetrahydrofuran complex, borane dimethyl sulfide complex, and so on.

<Step 3>

The compound (I) according to the present invention can be produced by various methods. Some typical methods are shown below.

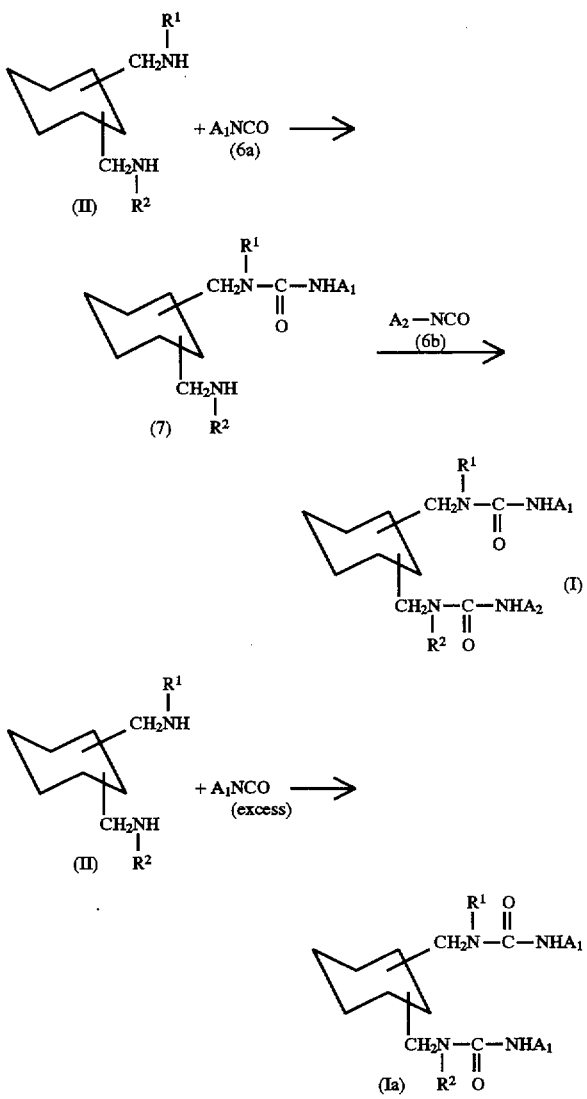

wherein $R^1$, $R^2$, $A_1$ and $A_2$ are as defined above.

The amine derivative of formula (II) is reacted with an isocyanate (6a) represented by $A_1NCO$ in a solvent at room temperature to approximately the boiling point of the solvent for 3–72 hours, thus giving a monourea (7). The monourea (7) is reacted with an isocyanate (6b) to provide an object compound (I). Examples of useful solvents are pyridine, benzene, toluene, dioxane, THF, ether, dichloromethane, chloroform, n-hexane, acetonitrile, DMF, etc. The isocyanate (6a) is used in an amount of 0.9–1.1 equivalents per mole of the diamine of formula (II). After completion of the reaction, the monourea (7) is separated and purified by a conventional purification method such as extraction with a solvent, recrystallization and column chromatography. The diurea of formula (I) can be prepared by reacting the monourea (7) with an isocyanate (6b) under the same conditions as mentioned above. The diurea of formula (Ia) wherein $A_1=A_2$ is usually prepared using 2 moles to an excess of an isocyanate (6a) per mole of the amine derivative (II).

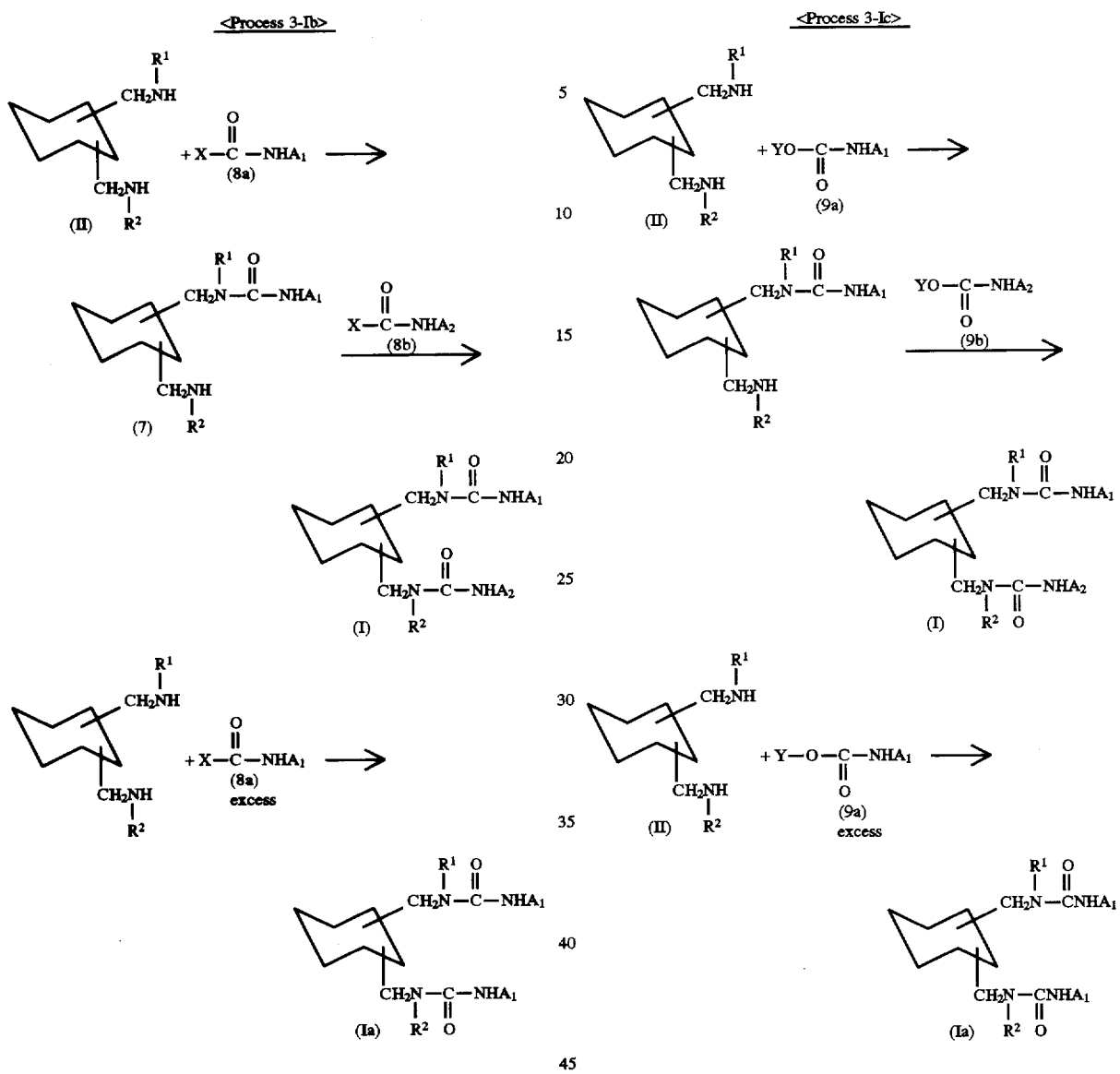

wherein X is a chlorine, bromine or iodine atom and $R^1$, $R^2$, $A_1$ and $A_2$ are as defined above.

One mole of an amine derivative of formula (II) is reacted with 1.0–1.1 moles of carbonyl halide (8a) in a solvent under ice-cooling or at room temperature for 1–6 hours to give a monourea (7). Examples of useful solvents are those inert to the reaction, such as benzene, toluene, dioxane, THF, ether, dichloromethane and chloroform. In the reaction, a base such as triethylamine, pyridine and dimethylaminopyridine can also be added in an amount of about 1.0–1.5 moles. After completion of the reaction, the reaction mixture is subjected to separation and purification in the same manner as in the above process 3-Ia, thus giving a monourea (7). The monourea (7) is reacted with carbonyl halide (8b) under the same conditions as mentioned above to give an object compound of formula (I).

The compound (Ia) wherein $A_1=A_2$ can be prepared by reacting an amine derivative of formula (II) with 2 equivalents to an excess of carbonyl halide (8a).

wherein Y represents a $C_{1-5}$ lower alkyl group or a phenyl group, and $R^1$, $R^2$, $A_1$ and $A_2$ are as defined above.

One mole of an amine derivative of formula (II) is reacted with about 0.9–1.1 moles of a carbamic acid ester of formula (9a) in the presence of a solvent at about 0° C. to approximately the boiling point of the solvent for 5–24 hours to give a monoamide (7). The monoamide (7) is separated and purified by a conventional purification method such as solvent extraction, column chromatography and recrystallization. The monoamide (7) is reacted with a carbamic acid ester of formula (9b) under the same conditions as mentioned above, thus giving an object compound of formula (I).

Examples of useful solvents are inert solvents such as benzene, toluene, dioxane, ether, THF, DMF, acetonitrile, chloroform, dichloromethane.

The compound (Ia) wherein $A_1=A_2$ according to the invention can be prepared by reacting an amine derivative of formula (II) with 2 equivalents to an excess of a carbamic acid ester (9a).

The carbamic acid ester used as the starting compound in the above reaction can be prepared by the following reaction:

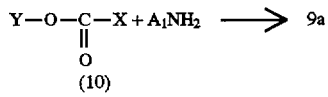
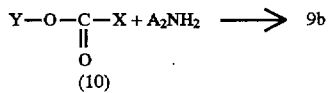

wherein Y, X, $A_1$ and $A_2$ are as defined above.

The carbamic acid ester (9a) or (9b) can be prepared by reacting a carbonic acid halide (10) such as isobutylcarbonic acid chloride, methylcarbonic acid chloride and phenylcarbonic acid chloride with $A_1NH_2$ or $A_2NH_2$ in a solvent in the presence or absence of a base. Examples of useful solvents are inert solvents, such as benzene, toluene, dioxane, ether, THF, chloroform, and dichloromethane. Examples of useful bases are potassium carbonate, sodium carbonate, sodium hydrogencarbonate, potassium hydroxide, sodium hydroxide, triethylamine, and N,N-dimethylaniline. The reaction is carried out under cooling or at room temperature for about 1–5 hours.

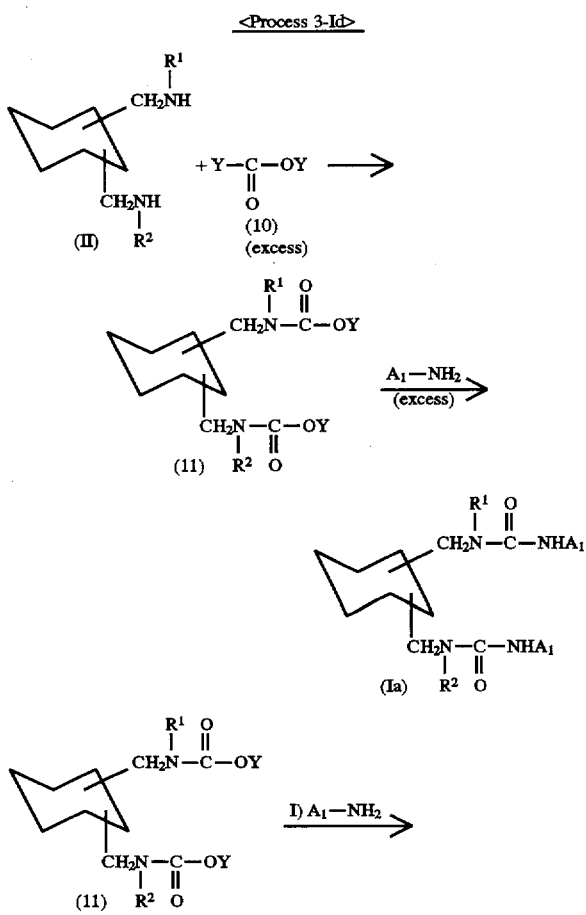

<Process 3-Id>

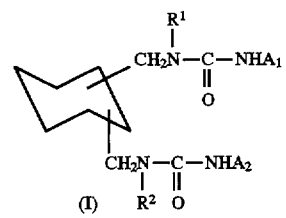

wherein Y, $R^1$, $R^2$, $A_1$ and $A_2$ are as defined above.

One mole of an diamine derivative of formula (II) is reacted with 2 equivalents to an excess of a carbonic acid halide (10) in a solvent under ice-cooling or at room temperature for 1–5 hours to give a dicarbamic acid ester (11). One mole of the ester (11) is reacted with 2 moles to an excess of $A_1NH_2$ at room temperature to approximately the melting point of the solvent for 2–12 hours to give a compound of formula (Ia).

Examples of useful solvents are inert solvents such as benzene, toluene, dioxane, ether, THF, chloroform and dichloromethane. The reaction between the diamine derivative of formula (II) and the carbonic acid halide (10) is carried out advantageously in the presence of a base such as potassium carbonate, sodium carbonate, sodium hydrogencarbonate, potassium hydroxide, sodium hydroxide, triethylamine and N,N-dimetylaniline.

The substitution reaction can be promoted by means of a phase transfer catalyst such as benzyltriethylammonium chloride, benzyltriethylammonium bromide, tetra-n-butylammonium chloride, tetra-n-butylammonium bromide, and tetra-n-butylammonium hydrogensulfate. The compound of formula (I) can also be prepared by reacting 1 mole of an ester (11) with 1 mole of $A_1NH_2$ and reacting the resulting monourea (12) with 1 mole or an excess of $A_1NH_2$ under the same conditions as mentioned above.

The isolation and purification can be done by a conventional chemical operation, such as extraction, recrystallization and various chromatographies.

The compound (I) of the present invention or a pharmacologically acceptable salt can be provided in a variety of dosage forms of preventive or therapeutic medicine. Examples of such forms are compositions for oral administration, injections, suppositories, attaching agents such as cataplasms and taping agents, ointments, creams and lotions. These dosage forms can be manufactured by conventional methods for preparing pharmaceutical compositions.

Solid pharmaceutical compositions for oral administration can be manufactured by optionally adding a binder, a disintegrator, a lubricant, a coloring agent, a flavor, a perfume, etc. to the compound of the invention and preparing the composition in the form of tablets, coated tablets, granule, powder, capsules, etc. by conventional methods. Conventional additives in this field can be used as such additives. Examples of useful excipients are lactose, sucrose, sodium chloride, glucose, starch, calcium carbonate, kaolin, crystalline cellulose and silicic acid.

Examples of useful binders are water, ethanol, propanol, simple syrup, glucose syrup, starch solution, gelatin solution, carboxymethylcellulose, carboxypropylcellulose, hydroxypropylstarch, methylcellulose, ethylcellulose, shellac, calcium phosphate, and polyvinylpyrrolidone. Examples of useful disintegrators are dry starch, sodium alginate, agar powder, sodium hydrogen carbonate, calcium carbonate, sodium lauryl sulfate, stearyl monoglyceride, and lactose. Examples of useful lubricants are purified talc, salts of stearic acid, boric acid powder, and polyethylene glycol. Examples of useful flavors are sucrose, bitter orange peel, citric acid, and tartaric acid.

Liquid pharmaceutical compositions for oral administration can be manufactured by optionally adding a flavor, a buffer, a stabilizer, a perfume, etc. to the compound of the invention and preparing the composition in the form of internal medicine, syrup, elixir, etc. by conventional methods. Examples of useful flavors are the same as mentioned above. Examples of useful buffers include sodium citrate. Examples of useful stabilizers include tragacanth, gum arabic, and gelatin.

Injections can be manufactured by optionally adding a pH adjusting agent, a buffer, a stabilizer, an isotonic agent, a local anesthetic, etc. to the compound of the invention and preparing hypodermic, intramuscular or intravenous injections by conventional methods. Examples of useful pH adjusting agents and buffers are sodium citrate, sodium acetate, sodium phosphate, etc. Examples of useful stabilizers are sodium pyrosulfite, EDTA, thioglycollic acid, thiolactic acid, etc. Examples of useful local anesthetics are procaine hydrochloride, lidocaine hydrochloride, etc.

Suppositories can be manufactured by adding a known pharmaceutically acceptable carrier such as polyethylene glycol, lanolin, cacao butter and fatty acid triglyceride and optionally a surfactant such as Tween (trademark) to the compound of the invention and preparing suppositories by conventional methods.

Ointments can be manufactured by optionally adding a base, a stabilizer, a humectant, a preservative, etc. to the compound of the present invention and mixing them by a conventional method to form ointments. Examples of useful bases are liquid paraffin, white vaseline, bleached bee wax, octyldodecyl alcohol, paraffin, etc. Examples of useful preservatives are methyl para-hydroxybenzoate, ethyl para-hydroxybenzoate, propyl para-hydroxybenzoate, etc.

Attaching agents can be manufactured by applying the above-mentioned ointment, cream, gel, paste, or the like to conventional substrates by conventional methods. Examples of suitable substrates are woven fabric of cotton, staple fiber or artificial fiber, unwoven fabrics, film of soft vinyl chloride, polyethylene or polyurethane, and expanded sheet.

Examples of the "pharmaceutically acceptable carrier" added to the compound of formula (I) are various additives mentioned above in the pharmaceutical preparations.

The amount of the compound of the invention to be incorporated in the above-mentioned dosage unit form may vary depending on the patient's condition, dosage form, etc. In the case of compositions for oral administration or injections, about 0.1–200 mg of the compound of the invention is preferably incorporated into a dosage unit form. The daily dosage of the medicament in the above-mentioned forms varies depending on patient's condition, weight, age, sex, etc. but generally, it is preferably about 0.1–200 mg per adult. This amount is preferably administered once or in 2–4 divided doses.

EXAMPLES

The following experimental examples and examples are intended to illustrate the invention in further detail and should by no means be construed as limiting the scope of the invention.

Examples illustrate the synthesis of compounds according to the invention. Synthesis Examples illustrate the synthesis of the starting compound and intermediate for the production of the compound of the invention. $^1$H-NMR means hydrogen nuclear magnetic resonance spectrum, mp melting point, MS mass spectrometry, and IR infrared absorption spectrum.

A. Synthesis of diamide

Synthesis Example 1

A 4.30 g quantity of trans-1,4-cyclohexanedicarbonic acid, 11.5 g of 1-ethyl-3-(3-dimethylamino-propyl) carbodiimide hydrochloride, 7.75 g of n-octylamine and 8.10 g of 1-hydroxybenzotriazole were dissolved in 200 ml of DMF and reacted at room temperature for 12 hours. The solvent was distilled off. The residue was extracted with ethyl acetate, washed with diluted hydrochloric acid, sodium carbonate and water in this order and dried over magnesium sulfate and the solvent was distilled off, thus giving 9.55 g (yield: 96.8%) of trans-1,4-cyclohexanedioctylamide.

Synthesis Examples 2–83

Diamide derivatives were prepared in the same manner as in Synthesis Example 1. Table 1 shows positions of the substituents of the diamide derivatives obtained in Synthesis Examples 1–83 and data on the results of measurement.

TABLE 1

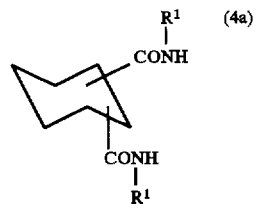

(4a)

| Synthesis Examples (Corresponding Example No.) | Position | $R^1$ | mp (°C.) | IR(νNH, νC = O) |
|---|---|---|---|---|
| 1(1) | trans-1,4 | -n(CH$_2$)$_7$CH$_3$ | 230–238 | 3320, 1637 |
| 2(2) | trans-1,4 | -n(CH$_2$)$_4$CH$_3$ | 271–278 | 3298, 1635 |
| 3(3) | trans-1,4 | -n(CH$_2$)$_5$CH$_3$ | 185(dec) | 3399, 1637 |

TABLE 1-continued $$\text{(4a)}$$

Structure: cyclohexane with R¹–NHCO– and –CONH–R¹ substituents

| Synthesis Examples (Corresponding Example No.) | Position | R¹ | mp (°C.) | IR(νNH, νC=O) |
|---|---|---|---|---|
| 4(4) | trans-1,4 | -n(CH₂)₆CH₃ | 232–239 | 3302, 1637 |
| 5(5) | trans-1,4 | -n(CH₂)₈CH₃ | 226–234 | 3319, 1633 |
| 6(6) | trans-1,4 | -n(CH₂)₉CH₃ | 225–230 | 3324, 1637 |
| 7(7) | trans-1,4 | —CH₂CCH₃)₃ | 279–285 | 3290, 1647 |
| 8(8) | trans-1,4 | —CH₂-cC₆H₁₁ | 285–295 | 3292, 1637 |
| 9(9) | trans-1,4 | —CH(CH₃)₂ | >300 | 3290, 1637 |
| 10(10) | trans-1,4 | —CH(CH₂CH₂CH₃)₂ | >300 | 3288, 1637 |
| 11(11) | trans-1,4 | -cC₅H₉ | >300 | 3293, 1633 |
| 12(12–14-12) | trans-1,4 | -cC₆H₁₁ | >300 | 3294, 1637 |
| 13(15–25) | trans-1,4 | -cC₇H₁₃ | >300 | 3299, 1631 |
| 14(26) | trans-1,4 | -cC₈H₁₅ | >300 | 3267, 1633 |
| 15(27) | trans-1,4 | -2-Norbornyl | >300 | 3284, 1635 |
| 16(28–28-3) | trans-1,4 | -cC₆H₁₀-4-CH₃ | >300 | 3298, 1635 |
| 17(29) | trans-1,4 | -2-Adamantyl | 268–272 | 3320, 1637 |
| 18(30) | trans-1,4 | —CH₂Ph | >300 | 3284, 1637 |
| 19(31) | trans-1,4 | —CH₂CH₂Ph | 281–290 | 3299, 1637 |
| 20(32) | trans-1,4 | —CH₂CH₂-1-cHexenyl | 275–278 | 3290, 1635 |
| 21(33) | trans-1,4 | -Furfuryl | >300 | 3320, 1631 |
| 22(34) | cis-1,4 | -n(CH₂)₆CH₃ | 52–56 | 3334, 1643 |
| 23(35) | cis-1,4 | -n(CH₂)₇CH₃ | 56–60 | 3334, 1637 |
| 24(36) | cis-1,4 | -n(CH₂)₈CH₃ | 52–57 | 3313, 1635 |
| 25(37) | cis-1,4 | -n(CH₂)₉CH₃ | 54–56 | 3311, 1633 |
| 26(38) | cis-1,4 | —CH₂C(CH₃)₃ | 201–207 | 2964, 1647 |
| 27(39) | cis-1,4 | —CH₂-cC₅H₁₁ | 147–150 | 3305, 1645 |
| 28(40) | cis-1,4 | —CH(CH₂CH₂CH₃)₂ | 151–155 | 3328, 1639 |
| 29(41) | cis-1,4 | -cC₅H₉ | 215–222 | 3284, 1631 |
| 30(42) | cis-1,4 | -cC₅H₁₁ | 154–158 | 2947, 1635 |
| 31(43) | cis-1,4 | -cC₇H₁₃ | 210–216 | 3298, 1641 |
| 32(44) | cis-1,4 | -CC₈H₁₅ | 160–182 | 2929, 1639 |
| 33(45) | cis-1,4 | -2-Norbornyl | 244–245 | 3336, 1641 |
| 34(46) | cis-1,4 | -2-Adamantyl | 294–300 | 3303, 1641 |
| 35(47) | cis-1,4 | —CH₂Ph | 130–132 | 3326, 1647 |
| 36(48) | cis-1,4 | —CH₂CH₂Ph | 105–106 | 3292, 1635 |
| 37(49) | cis-1,4 | —CH₂CH₂-1-cHexenyl | 100–103 | 3319, 1637 |
| 38(50) | cis-1,4 | -Furfuryl | 130–145 | 3305, 1647 |
| 39(51) | trans-1,3 | -n(CH₂)₄CH₃ | 94–96 | 3291, 1637 |
| 40(52) | trans-1,3 | -n(CH₂)₅CH₃ | 71–74 | 3296, 1639 |
| 41(53) | trans-1,3 | -n(CH₂)₆CH₃ | 75–79 | 3290, 1637 |
| 42(54) | trans-1,3 | -n(CH₂)₇CH₃ | 75–80 | 3313, 1639 |
| 43(55) | trans-1,3 | -n(CH₂)₈CH₃ | 80–82 | 3315, 1639 |
| 44(56) | trans-1,3 | -n(CH₂)₉CH₃ | 86–91 | 3307, 1637 |
| 45(57) | trans-1,3 | —CH₂-cC₅H₁₁ | 190–192 | 3291, 1637 |
| 46(58) | trans-1,3 | —CH(CH₂CH₂CH₃)₂ | 210–218 | 3292, 1641 |
| 47(59) | trans-1,3 | -cC₅H₉ | 230–239 | 3291, 1635 |
| 48(60) | trans-1,3 | -cC₆H₁₁ | 230–235 | 3296, 1637 |
| 49(61) | trans-1,3 | -cC₇H₁₃ | 236–239 | 3298, 1637 |
| 50(62) | trans-1,3 | -2-Norbornyl | 252–258 | 3322, 1639 |
| 51(63) | trans-1,3 | -cC₅H₁₀-4-CH₃ | 206–212 | 3284, 1639 |
| 52(64) | trans-1,3 | —CH₂Ph | 105–109 | 3286, 1637 |
| 53(65) | trans-1,3 | —CH₂CH₂Ph | 106–109 | 3320, 1643 |
| 54(66) | trans-1,3 | —CH₂CH₂-cHexenyl | 125–130 | 3280, 1637 |
| 55(67) | cis-1,3 | -n(CH₂)₄CH₃ | 225–227 | 3291, 1639 |
| 56(68) | cis-1,3 | -n(CH₂)₅CH₃ | 209–214 | 3286, 1639 |
| 57(69) | cis-1,3 | -n(CH₂)₆CH₃ | 208–211 | 3292, 1639 |
| 58(70) | cis-1,3 | -n(CH₂)₇CH₃ | 175–181 | 3292, 1639 |
| 59(71) | cis-1,3 | -n(CH₂)₈CH₃ | 198–201 | 3298, 1639 |
| 60(72) | cis-1,3 | -n(CH₂)₉CH₃ | 194–197 | 3301, 1639 |
| 61(73) | cis-1,3 | —CH₂C(CH₃)₃ | 252–261 | 3292, 1644 |
| 62(74) | cis-1,3 | —CH₂-cC₈H₁₁ | 245–249 | 3295, 1639 |
| 63(75) | cis-1,3 | —CH(CH₃)₂ | 279–290 | 3292, 1639 |
| 64(76) | cis-1,3 | —CH(CH₂CH₃)₂ | 272–281 | 3282, 1642 |
| 65(77) | cis-1,3 | —CH(CH₂CH₂CH₃)₂ | 258–266 | 3322, 1637 |
| 66(78) | cis-1,3 | -cC₅H₉ | >300 | 3272, 1631 |

TABLE 1-continued $$\text{(4a)}$$

Structure: cyclohexane with CONH-R¹ groups

| Synthesis Examples (Corresponding Example No.) | Position | R¹ | mp (°C.) | IR(vNH, vC = 0) |
|---|---|---|---|---|
| 67(79-82) | cis-1,3 | -cC₆H₁₁ | 299–306 | 3299, 1639 |
| 68(83) | cis-1,3 | -cC₇H₁₃ | >300 | 3298, 1637 |
| 69(84) | cis-1,3 | -cC₈H₁₅ | 291–295 | 3245, 1633 |
| 70(85) | cis-1,3 | -2-Norbornyl | >300 | 3282, 1637 |
| 71(86) | cis-1,3 | —CH₂Ph | 195(dec) | 3294, 1637 |
| 72(87) | cis-1,3 | —CH₂CH₂Ph | 251–253 | 3292, 1639 |
| 73(88) | cis-1,3 | —CH₂CH₂-1-cHexenyl | 221–228 | 3288, 1641 |
| 74(89) | cis-1,3 | -Furfuryl | 230–237 | 3293, 1641 |
| 75(90) | cis-1,2 | -n(CH₂)₈CH₃ | 112–115 | 3299, 1643 |
| 76(91) | trans-1,2 | -cC₆H₁₁ | 284–286 | 3309, 1641 |
| 77(92) | trans-1,2 | -cC₇H₁₃ | 277–281 | 3294, 1639 |
| 78(93) | trans-1,2 | —CH₂Ph | 219–225 | 3268, 1645 |
| 79(94) | trans-1,2 | -n(CH₂)₈CH₃ | 173–185 | 3299, 1644 |
| 80(95) | cis-1,2 | —CH₂-cC₆H₁₁ | 178–181 | 3276, 1641 |
| 81(96) | cis-1,2 | -cC₅H₁₁ | 266–268 | 2929, 1639 |
| 82(97) | cis-1,2 | -cC₇H₁₃ | 253–257 | 3251, 1639 |
| 83(98) | cis-1,2 | -Furfuryl | 132–136 | 3282, 1644 |

B. Synthesis of diamine

Preparation Example 1

Lithiumaluminum hydride, 2.17 g, was added little by little under ice-cooling to 150 ml of a THF suspension containing 8.70 g of the diamide derivative prepared in Synthesis Example 1. Stirring was continued for 1 hour and the reaction mixture was refluxed with heating for 65 hours. After adding 4.3 ml of water and 4.3 ml of a 2N aqueous sodium hydroxide solution under ice-cooling, the reaction mixture was allowed to stand at room temperature for 15 hours. The reaction mixture was filtered with suction and the filtrate was concentrated under reduced pressure. The residue was dissolved in hexane and washed with a saturated aqueous sodium bicarbonate solution and saturated brine. The organic layer was dried over anhydrous sodium sulfate and concentrated under reduced pressure to provide 5.03 g (yield: 76.2%) of a diamine derivative as a viscous oil compound.

Preparation Examples 2–83

Diamine derivatives were prepared in the same manner as in Preparation Example 1.

Table 2 shows positions of the substituents of the diamine derivatives obtained in Preparation Examples 1–83 and data on the results of measurement.

TABLE 2

Structure: cyclohexane with CH₂NH-R¹ groups

| Synthesis Examples (Corresponding Example No.) | Position | R¹ | IR(v) | NMR(DMSO-d6) δ:(CH₂NHR¹) |
|---|---|---|---|---|
| 1(1) | trans-1,4 | -n(CH₂)₇CH₃ | 1452, 2924 | 2.31 |
| 2(2) | trans-1,4 | -n(CH₂)₄CH₃ | 1450, 2924 | 2.31 |
| 3(3) | trans-1,4 | -n(CH₂)₅CH₃ | 1450, 2929 | 2.36 |
| 4(4) | trans-1,4 | -n(CH₂)₆CH₃ | 1454, 2927 | 2.31 |
| 5(5) | trans-1,4 | -n(CH₂)₈CH₃ | 1448, 2922 | 2.31 |
| 6(6) | trans-1,4 | -n(CH₂)₉CH₃ | 1448, 2922 | 2.31 |
| 7(7) | trans-1,4 | —CH₂C(CH₃)₃ | 1462, 2912 | 2.36 |

TABLE 2-continued

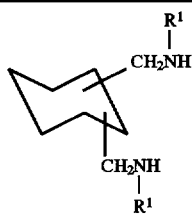

| Synthesis Examples (Corresponding Example No.) | Position | R¹ | IR(ν) | NMR(DMSO-d6) δ:(CH₂NHR¹) |
|---|---|---|---|---|
| 8(8) | trans-1,4 | —CH₂-cC₆H₁₁ | 1446, 2915 | 2.30 |
| 9(9) | trans-1,4 | —CH(CH₃)₂ | 1448, 2920 | 2.32 |
| 10(10) | trans-1,4 | —CH(CH₂CH₂CH₃)₂ | 1466, 2924 | 2.31 |
| 11(11) | trans-1,4 | -cC₅H₉ | 1444, 2914 | 2.31 |
| 12(12~14-12) | trans-1,4 | -cC₆H₁₁ | 1454, 2913 | 2.34 |
| 13(15-25) | trans-1,4 | -cC₇H₁₃ | 1460, 2925 | 2.32 |
| 14(26) | trans-1,4 | -cC₈H₁₅ | 1448, 2924 | 2.31 |
| 15(27) | trans-1,4 | -2-Norbornyl | 1448, 2949 | 2.32 |
| 16(28~28-3) | trans-1,4 | -cC₆H₁₀-4-CH₃ | 1441, 2918 | 2.31 |
| 17(29) | trans-1,4 | -2-Adamantyl | 1446, 2906 | 2.35 |
| 18(30) | trans-1,4 | —CH₂Ph | 1450, 2929 | 2.33 |
| 19(31) | trans-1,4 | —CH₂CH₂Ph | 1452, 2916 | 2.36 |
| 20(32) | trans-1,4 | —CH₂CH₂-1-cHexenyl | 1466, 2922 | 2.33 |
| 21(33) | trans-1,4 | -Furfuryl | 1448, 2916 | 2.33 |
| 22(34) | cis-1,4 | -n(CH₂)₆CH₃ | 1456, 2925 | 2.38 |
| 23(35) | cis-1,4 | -n(CH₂)₇CH₃ | 1463, 2923 | 2.39 |
| 24(36) | cis-1,4 | -n(CH₂)₈CH₃ | 1464, 2924 | 2.39 |
| 25(37) | cis-1,4 | -n(CH₂)₉CH₃ | 1466, 2924 | 2.38 |
| 26(38) | cis-1,4 | —CH₂C(CH₃)₃ | 1463, 2950 | 2.43 |
| 27(39) | cis-1,4 | —CH₂-cC₆H₁₁ | 1448, 2922 | 2.31 |
| 28(40) | cis-1,4 | —CH(CH₂CH₂CH₃)₂ | 1466, 2929 | 2.39 |
| 29(41) | cis-1,4 | -cC₅H₉ | 1450, 2922 | 2.38 |
| 30(42) | cis-1,4 | -cC₆H₁₁ | 1450, 2927 | 2.45 |
| 31(43) | cis-1,4 | -cC₇H₁₃ | 1448, 2924 | 2.43 |
| 32(44) | cis-1,4 | -cC₈H₁₅ | 1448, 2924 | 2.40 |
| 33(45) | cis-1,4 | -2-Norbornyl | 1448, 2952 | 2.37 |
| 34(46) | cis-1,4 | -2-Adamantyl | 1444, 2906 | 2.42 |
| 35(47) | cis-1,4 | —CH₂Ph | 1452, 2922 | 2.38 |
| 36(48) | cis-1,4 | —CH₂CH₂Ph | 1454, 2922 | 2.44 |
| 37(49) | cis-1,4 | —CH₂CH₂-1-cHexenyl | 1448, 2924 | 2.40 |
| 38(50) | cis-1,4 | -Furfuryl | 1450, 2924 | 2.40 |
| 39(51) | trans-1,3 | -n(CH₂)₄CH₃ | 1460, 2929 | 2.39 |
| 40(52) | trans-1,3 | -n(CH₂)₅CH₃ | 1461, 2927 | 2.38 |
| 41(53) | trans-1,3 | -n(CH₂)₆CH₃ | 1459, 2927 | 2.38 |
| 42(54) | trans-1,3 | -n(CH₂)₇CH₃ | 1464, 2925 | 2.40 |
| 43(55) | trans-1,3 | -n(CH₂)₈CH₃ | 1463, 2924 | 2.38 |
| 44(56) | trans-1,3 | -n(CH₂)₉CH₃ | 1464, 2925 | 2.38 |
| 45(57) | trans-1,3 | —CH₂-cC₆H₁₁ | 1448, 2921 | 2.31 |
| 46(58) | trans-1,3 | —CH(CH₂CH₂CH₃)₂ | 1460, 2952 | 2.38 |
| 47(59) | trans-1,3 | -cC₅H₉ | 1450, 2929 | 2.39 |
| 48(60) | trans-1,3 | -cC₆H₁₁ | 1450, 2929 | 2.41 |
| 49(61) | trans-1,3 | -cC₇H₁₃ | 1460, 2925 | 2.38 |
| 50(62) | trans-1,3 | -2-Norbornyl | 1462, 2952 | 2.36 |
| 51(63) | trans-1,3 | -cC₅H₁₀-4-CH₃ | 1450, 2924 | 2.38 |
| 52(64) | trans-1,3 | —CH₂Ph | 1454, 2923 | 2.38 |
| 53(65) | trans-1,3 | —CH₂CH₂Ph | 1454, 2925 | 2.42 |
| 54(66) | trans-1,3 | —CH₂CH₂-cHexenyl | 1448, 2925 | 2.38 |
| 55(67) | cis-1,3 | -n(CH₂)₄CH₃ | 1458, 2927 | 2.31 |
| 56(68) | cis-1,3 | -n(CH₂)₅CH₃ | 1458, 2925 | 2.31 |
| 57(69) | cis-1,3 | -n(CH₂)₆CH₃ | 1458, 2927 | 2.32 |
| 58(70) | cis-1,3 | -n(CH₂)₇CH₃ | 1448, 2927 | 2.32 |
| 59(71) | cis-1,3 | -n(CH₂)₈CH₃ | 1458, 2927 | 2.31 |
| 60(72) | cis-1,3 | -n(CH₂)₉CH₃ | 1458, 2923 | 2.32 |
| 61(73) | cis-1,3 | —CH₂C(CH₃)₃ | 1462, 2920 | 2.35 |
| 62(74) | cis-1,3 | —CH₂-cC₆H₁₁ | 1460, 2916 | 2.30 |
| 63(75) | cis-1,3 | —CH(CH₃)₂ | 1471, 2922 | 2.32 |
| 64(76) | cis-1,3 | —CH(CH₂CH₃)₂ | 1459, 2924 | 2.32 |
| 65(77) | cis-1,3 | —CH(CH₂CH₂CH₃)₂ | 1459, 2924 | 2.34 |
| 66(78) | cis-1,3 | -cC₅H₉ | 1448, 2922 | 2.31 |
| 67(79-82) | cis-1,3 | -cC₆H₁₁ | 1450, 2925 | 2.35 |
| 68(83) | cis-1,3 | -cC₇H₁₃ | 1448, 2925 | 2.31 |
| 69(84) | cis-1,3 | -cC₈H₁₅ | 1446, 2922 | 2.31 |
| 70(85) | cis-1,3 | -2-Norbornyl | 1450, 2943 | 2.31 |

TABLE 2-continued

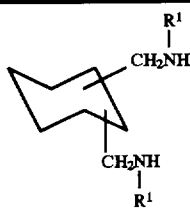

| Synthesis Examples (Corresponding Example No.) | Position | R¹ | IR(v) | NMR(DMSO-d6) δ:(CH₂NHR¹) |
|---|---|---|---|---|
| 71(86) | cis-1,3 | —CH₂Ph | 1454, 2920 | 2.32 |
| 72(87) | cis-1,3 | —CH₂CH₂Ph | 1454, 2922 | 2.35 |
| 73(88) | cis-1,3 | —CH₂CH₂-1-cHexenyl | 1446, 2922 | 2.32 |
| 74(89) | cis-1,3 | -Furfuryl | 1448, 2924 | 2.33 |
| 75(90) | cis-1,2 | -n(CH₂)₆CH₃ | 1448, 2929 | 2.42 |
| 76(91) | trans-1,2 | -cC₆H₁₁ | 1448, 2925 | 2.36 |
| 77(92) | trans-1,2 | -cC₇H₁₃ | 1448, 2929 | 2.35 |
| 78(93) | trans-1,2 | —CH₂Ph | 1452, 2922 | 2.36 |
| 79(94) | trans-1,2 | -n(CH₂)₆CH₃ | 1448, 2927 | 2.37 |
| 80(95) | cis-1,2 | —CH₂-cC₆H₁₁ | 1448, 2924 | 2.44 |
| 81(96) | cis-1,2 | -cC₆H₁₁ | 1450, 2929 | 2.33 |
| 82(97) | cis-1,2 | -cC₇H₁₃ | 1448, 2925 | 2.32 |
| 83(98) | cis-1,2 | -Furfuryl | 1448, 2925 | 2.40 |

Example 1

Trans-1,4-bis[3-(4-dimethylaminophenyl)-1-normaloctylureido]methyl]cyclohexane

A 1.28 g quantity of phenyl 4-dimethylaminophenylcarbamate, 0.28 g of tetrabutylammonium bromide (TBAB) and 0.33 g of potassium hydroxide were added to a solution of 0.73 g of trans-1,4-bis[(normaloctylamino)methyl]cyclohexane in 30 ml of acetonitrile and stirred at room temperature for 15 hours. After completion of the reaction, the crystals precipitated were separated by filtration and washed with ether, water and hexane. After purifying the crystals by silica gel column chromatography, the crystals were dissolved in chloroform and a 4N hydrochloric acid-dioxane solution was added to provide 1.21 g (yield: 79%) of white crystals precipitated.

mp: 185°–189° C. (dihydrochloric acid salt) MS(FAB): m/e=647 (M⁺+1) IR(KBr) v MAX: 2923, 2366(brs), 1644 (s), 1521(s) NMR(DMSO-d₆) δ: 8.27 (2H, brs, NH×2), 7.4–7.6 (8H, br, Ar—H ), 3.28 (4H, brs, NCH₂×2), 3.16 (4H, br, NCH₂×2), 3.05 (4H, br, N(CH₃)₂×2), 1.2–1.8 (32H, m), 0.8–1.0 (8H, m) Elemental analysis (for C₄₂H₇₀N₆O₂.2HCl.H₂O) Calculated (%): C, 64.51; H, 9.54; N, 10.75. Found (%): C, 64.72; H, 9.33; N, 10.68.

Example 2

Trans-1,4-bis[[3-(4-dimethylaminophenyl)-1-normalpentylureido]methyl]cyclohexane Trans-1,4-bis[(normalpentylamino)methyl]cyclohexane, 0.56 g, was dissolved in 10 ml of ether. A solution of 0.81 g of 4-dimethylaminophenyl isocyanate in 20 ml of acetonitrile was added. The reaction mixture was stirred at room temperature for 10 hours. The solvent of the reaction mixture was distilled off under reduced pressure and the residue was purified by silica gel column chromatography to provide 1.10 g (yield: 89%) of white crystals.

mp: 205°–208° C. (free form) MS(FAB): m/e=607 (M⁺+1) IR(KBr) v MAX: 2912, 1633(s), 1519(s) NMR(DMSO-d₆) δ: 7.66 (2H, s, NH×2), 7.20 (4H, d, J=9.2 Hz, Ar—H), 6.63 (4H, d, J=9.2 Hz, Ar—H), 3.1–3.3 (8H, m, NCH₂×2, NCH₂×2), 2.81 (12H, s, N(CH₃)₂×2), 1.2–1.8 (18H, m), 0.8–1.0 (10H, m) Elemental analysis (for C₃₆H₅₈N₆O₂.2H₂O) Calculated (%): C, 67.25; H, 9.72; N, 13.07. Found (%): C, 66.77; H, 9.94; N, 12.83.

Example 3

Trans-1,4-bis[[3-(4-dimethylaminophenyl)-1-normalhexylureido]methyl]cyclohexane

The title compound was synthesized by the method in accordance with Example 1.

mp: 160°–163° (dihydrochloric acid salt) MS(FAB): m/e= 635 (M⁺+1) IR(KBr) v MAX: 2927(brs), 1646(s), 1521(s) NMR(DMSO-d₆) δ: 8.27 (2H, brs, NH×2), 7.50–7.70 (8H, brs, Ar—H), 3.0–3.4 (20H, br, NCH₂×2, NCH₂×2, N(CH₃)₂×2), 1.2–1.8 (24H, m), 0.8–1.0 (8H, m) Elemental analysis (for C₃₈H₆₂N₆O₂.2HCl.H₂O) Calculated (%): C, 62.88; H, 9.16; N, 11.58. Found (%): C, 62.60; H, 9.40; N, 11.86.

Example 4

Trans-1,4-bis[[3-(4-dimethylaminophenyl)-1-normalheptylureido]methyl]cyclohexane The title compound was synthesized by the method in accordance with Example 1.

mp: 189°–191° C. (dihydrochloric acid salt) MS(FAB): m/e=662 (M⁺) IR(KBr) v MAX: 2925(brs), 1648(s), 1521(s) NMR(DMSO-d₆) δ: 8.32 (2H, s, NH×2), 7.4–7.7 (8H, m, Ar—H), 3.33 (4H, m, NCH₂×2), 3.22 (4H, m, NCH₂×2), 3.10 (12H, s, N(CH₃)₂×2), 1.5–1.8 (10H, m), 1.2–1.4 (16H, m), 0.8–1.0 (10H, m) Elemental analysis (for C₄₀H₆₆N₆O₂.2HCl.H₂O) Calculated (%): C, 63.72; H, 9.35; N, 11.15. Found (%): C, 63.91; H, 9.69; N, 11.10.

Example 5

Trans-1,4-bis[[3-(4-dimethylaminophenyl)-1-normalnonylureido]methyl]cyclohexane

The title compound was synthesized by the method in accordance with Example 1.

mp: 220°–223° C. (dihydrochloric acid salt) MS(FAB): m/e=719 (M⁺+1) IR(KBr) ν MAX: 2923(brs), 1643(s), 1521(s) NMR(DMSO-d₆) δ: 8.23 (2H, brs, NH×2), 7.4–7.6 (8H, br, Ar—H), 3.28 (4H, t, J=7.0 Hz, NCH₂×2), 3.16 (4H, d, J=7.3 Hz, NCH₂×2), 3.04 (12H, s, N(CH₃)₂×2), 1.2–1.8 (36H, m), 0.8–1.0 (8H, m) Elemental analysis (for C₄₄H₇₄N₆O₂.2HCl.½H₂O) Calculated (%): C, 65.98; H, 9.69; N, 10.49. Found (%): C, 66.05; H, 9.43; N, 10.42.

Example 6

Trans-1,4-bis[[3-(4-dimethylaminophenyl)-1-normaldecylureido]methyl]cyclohexane

The title compound was synthesized by the method in accordance with Example 1.

mp: 155°–160° C. (dihydrochloric acid salt) MS(FAB): m/e=746 (M⁺) IR(KBr) ν MAX: 2921, 2979(brs), 1671(s), 1643(s) NMR(DMSO-d₆) δ: 8.28 (2H, brs, NH×2), 7.4–7.7 (8H, br, Ar—H), 3.28 (4H, br, NCH₂×2), 3.16 (4H, br, NCH₂×2), 3.05 (12H, s, N(CH₃)₂×2), 1.4–1.8 (8H, m), 1.2–1.3 (32H, m), 0.92 (2H, m), 0.85 (6H, t, J=7.0 Hz, CH₃×2) Elemental analysis (for C₄₆H₇₈N₆O₂.2HCl.½H₂O) Calculated (%): C, 66.64; H, 9.85; N, 10.14. Found (%): C, 66.48; H, 10.02; N, 10.39.

Example 7

Trans-1,4-bis[[3-(4-dimethylaminophenyl)-1-neopentylureido]methyl]cyclohexane

The title compound was synthesized by the method in accordance with Example 1.

mp: 196°–198° C. (dihydrochloric acid salt) MS(FAB): m/e=607 (M⁺+1) IR(KBr) ν MAX: 2923(brs), 1652(s), 1519(s) NMR(DMSO-d₆) δ: 8.44 (2H, s, NH×2), 7.55 (8H, br, Ar—H), 3.0–3.3 (20H, m, NCH₂×4, N(CH₃)₂×2), 1.5–1.7 (6H, m), 0.8–1.0 (22H, m) Elemental analysis (for C₃₆H₅₈N₆O₂.2HCl.H₂O) Calculated (%): C, 61.96; H, 8.96; N, 12.04. Found (%): C, 61.90; H, 8.77; N, 12.20.

Example 8

Trans-1,4-bis[[1-cyclohexylmethyl-3-(4-dimethylaminophenyl)ureido]methyl]cyclohexane The title compound was synthesized by the method in accordance with Example 1.

mp: 210°–212° C. (dihydrochloric acid salt) MS(FAB): m/e=659 (M⁺+1) IR(KBr) ν MAX: 2919(brs), 1656(s), 1513(s) NMR(DMSO-d₆) δ: 8.25 (2H, s, NH×2), 7.4–7.7 (8H, s, Ar—H), 3.1–3.3 (20H, m, NCH₂×4, N(CH₃)₂×2), 1.5–1.7 (24H, m), 1.0–1.3 (4H, m), 0.8–1.0 (4H, m) Elemental analysis (for C₄₀H₆₂N₆O₂.2HCl.3/2H₂O) Calculated (%): C, 63.31; H, 8.90; N, 11.07. Found (%): C, 63.38; H, 8.84; N, 11.23.

Example 9

Trans-1,4-bis[[S-(4-dimethylaminophenyl)-1-isopropylureido]methyl]cyclohexane

The title compound was synthesized by the method in accordance with Example 1.

mp: 204°–207° C. (dihydrochloric acid salt) MS(FAB): m/e=551 (M⁺+1) IR(KBr) ν MAX: 2923(brs), 1635(s), 1448(s) NMR(DMSO-d₆) δ: 8.33 (2H, s, NH×2), 7.56 (8H, br, Ar—H), 4.20 (2H, m, NCH×2), 3.0–3.2 (16H, NCH₂×2, N(CH₃)₂×2), 1.5–1.7 (6H, m), 1.14 (12H, d, J=6.6 Hz, CH(CH₃)₂×2), 0.8–1.0 (4H, m) Elemental analysis (for C₃₂H₅₄N₆O₂.2HCl.H₂O) Calculated (%): C, 59.89; H, 8.48; N, 13.10. Found (%): C, 59.60; H, 8.48; N, 13.38.

Example 10

Trans-1,4-bis[[3-(4-dimethylaminophenyl)-1-(4-heptyl)ureido]methyl]cyclohexane

The title compound was synthesized by the method in accordance with Example 2.

mp: 173°–176° C. (free form) MS(FAB): m/e=663 (M⁺+1) IR(KBr) ν MAX: 2964(s), 1623(s), 1592(s), 1521(s) NMR(DMSO-d₆) δ: 7.57 (2H, s, NH×2), 7.18 (4H, d, J=9.0 Hz Ar—H), 6.62 (4H, d, J=9.0 Hz, Ar—H), 3.92 (2H, s, NCH×2), 2.97 (4H, d, J=7.3 Hz, NCH₂×2), 2.81 (12H, s, N(CH₃)₂×2), 1.2–1.8 (24H, m), 0.8–1.0 (16H, m) Elemental analysis (for C₄₀H₆₆N₆O₂) Calculated (%): C, 72.46; H, 10.03; N, 12.68. Found (%): C, 72.12; H, 10.22; N, 12.49.

Example 11

Trans-1,4-bis[[1-cyclopentyl-3-(4-dimethylaminophenyl)ureido]methyl]cyclohexane

The title compound was synthesized by the method in accordance with Example 1.

mp: 202°–204° C. (dihydrochloric acid salt) MS(FAB): m/e=602 (M⁺) IR(KBr) ν MAX: 2915(brs), 1631(s), 1519(s) NMR(DMSO-d₆) δ: 8.34 (2H, s, NH×2), 7.56 (8H, s, Ar—H), 4.17 (2H, m, NCH×2), 3.10 (4H, d, J=7.0 Hz, NCH₂×2), 3.06 (12H, s, N(CH₃)₂2), 1.5–1.8 (22H, m), 0.8–1.0 (4H, m) Elemental analysis (for C₃₆H₅₄N₆O₂.2HCl.H₂O) Calculated (%): C, 62.32; H, 8.43; N, 12.11.

Found (%): C, 61.80; H, 8.96; N, 12.00.

Example 12

Trans-1,4-bis[[1-cyclohexyl-3-(4-dimethylaminophenyl)ureido]methyl]cyclohexane

The title compound was synthesized by the method in accordance with Example 1.

mp: 200°–202° (dihydrochloric acid salt) MS(FAB): m/e= 631 (M⁺+1) IR(KBr) ν MAX: 2923(brs), 1652(s), 1519(s) NMR(DMSO-d₆) δ: 8.34 (2H, s, NH×2), 7.56 (8H, brs, Ar—H), 3.82 (2H, m, NCH×2), 3.09 (4H, d, J=7.0 Hz, NCH₂×2), 3.06 (12H, s, N(CH₃)₂x 2), 0.8–1.8 (30H, m) Elemental analysis (for C₃₈H₅₈N₆O₂.2HCl) Calculated (%): C, 62.45; H, 8.69; N, 11.50.

Found (%): C, 62.31; H, 8.82; N, 11.40.

Example 12-1

Trans-1,4-bis[[1-cyclohexyl-3-(4-dimethylaminophenyl)ureido]methyl]cyclohexane

The title compound was synthesized by the method in accordance with Example 1.

mp: 145°–147° (fumaric acid salt) MS(FAB): m/e=631 (M⁺+1) IR(KBr) ν MAX: 2922(brs), 1626(s), 1518(s) NMR (DMSO-d₆) δ: 7.66 (2H, s, NH×2), 7.18 (4H, d, J=9.2 Hz, Ar—H), 6.63 (4H, d, J=9.2 Hz, Ar—H), 6.62 (2H, s, =CH×2), 3.78 (2H, br, NCH×2), 3.03 (4H, d, J=6.9 Hz, NCH₂×2), 2.81 (12H, s, N(CH₃)₂×2), 0.8–1.8 (30H, m) Elemental analysis (for C₃₈H₅₈N₆O₂.C₄H₄O₄.H₂O) Calculated (%): C, 65.94; H, 8.43; N, 10.99. Found (%): C, 65.81; H, 8.62; N, 10.76.

Example 12-2

Trans-1,4-bis[[1-cyclohexyl-3-(4-dimethylaminophenyl)ureido]methyl]cyclohexane

The title compound was synthesized by the method in accordance with Example 1.

mp: 128°–131° C. (maleic acid salt) MS(FAB): m/e=631 (M$^+$+1) IR(KBr) v MAX: 2927(brs), 1633(s), 1518(s) NMR (DMSO-d$_6$) δ: 7.66 (2H, s, NH×2), 7.19 (4H, d, J=9.2 Hz, Ar—H), 6.63 (4H, d, J=9.2 Hz, Ar—H), 6.19 (2H, s, =CH×2), 3.79 (2H, br, NCH×2), 3.0–3.2 (4H, br, NCH$_2$×2), 2.83 (12H, s, N(CH$_3$)$_2$×0.8–1.8 (30H, m) Elemental analysis (for C$_{38}$H$_{58}$N$_6$O$_2$·C$_4$H$_4$O$_4$·½H$_2$O) Calculated (%): C, 66.73; H, 8.46; N, 11.12. Found (%): C, 66.75; H, 8.04; N, 10.90.

Example 12-3

Trans-1,4-bis[[1-cyclohexyl-3-(4-dimethylaminophenyl)ureido]methyl]cyclohexane

The title compound was synthesized by the method in accordance with Example 1.

mp: 110°–115° C. (dimethanesulfonic acid salt) MS(FAB): m/e=631 (M$^+$+1) IR(KBr) v MAX: 2922(brs), 1637(s), 1517(s) NMR(DMSO-d$_6$) δ: 8.20 (2H, br, NH×2), 7.2–7.6 (8H, br, Ar—H), 3.80 (2H, br, NCH×2), 3.0–3.2 (16H, br), 2.38 (6H, s, SCH$_3$×2), 0.8–1.8 (30H, m) Elemental analysis (for C$_{38}$H$_{58}$N$_6$O$_2$·2CH$_4$O$_3$S.3H$_2$O) Calculated (%): C, 54.78; H, 8.27; N, 9.58. Found (%): C, 54.49; H, 8.43; N, 9.76.

Example 13

Trans-1,4-bis[[1-cyclohexyl-3-(4-piperidinophenyl)ureido]methyl]cyclohexane

The title compound was synthesized by the method in accordance with Example 1.

mp: 174°–178° C. (dihydrochloric acid salt) MS(FAB): m/e=711 (M$^+$+1) IR(KBr) v MAX: 2938(brs), 1648(s), 1515(s) NMR(DMSO-d$_6$) δ: 8.34 (2H, s, NH×2), 7.5–7.7 (8H, m, Ar—H), 3.80 (2H, m, NCH×2), 3.4–3.5 (8H, N(CH$_2$)$_2$×2), 3.09 (4H, d, J=7.3 Hz, NCH$_2$×2), 0.8–1.8 (42H, m) Elemental analysis (for C$_{44}$H$_{66}$N$_6$O$_2$·2HCl.5/2H$_2$O) Calculated (%): C, 63.75; H, 8.88; N, 10.14. Found (%): C, 63.83; H, 8.85; N, 9.79.

Example 14

Trans-1,4-bis[[1-cyclohexyl-3-(4-diethylaminophenyl)ureido]methyl]cyclohexane

The title compound was synthesized by the method in accordance with Example 1.

mp: 212°–217° C. (dihydrochloric acid salt) MS(FAB): m/e=686 (M$^+$+1) IR(KBr) v MAX: 2925(brs), 1629(s), 1521(s) NMR(DMSO-d$_6$) δ: 8.39 (2H, s, NH×2), 7.5–7.7 (8H, m, Ar—H), 3.81 (2H, m, NCH×2), 3.4–3.6 (8H, N(CH$_2$)$_2$×2), 3.09 (4H, d, J=7.0 Hz, NCH$_2$×2), 0.8–1.8 (42H, m) Elemental analysis (for C$_{46}$H$_{66}$N$_6$O$_2$·2HCl.9/2H$_2$O) Calculated (%): C, 59.98; H, 9.22; N, 9.99. Found (%): C, 59.79; H, 8.80; N, 9.87.

Example 14-1

Trans-1,4-bis[[1-cyclohexyl-3-(4-pyrrolidinophenyl)ureido]methyl]cyclohexane

The title compound was synthesized by the method in accordance with Example 1.

mp: 149°–152° C. (dihydrochloric acid salt) MS(FAB): m/e=683 (M$^+$+1) IR(KBr) v MAX: 2929(brs), 1645(s), 1518(s) NMR(DMSO-d$_6$) δ: 8.18 (2H, br, NH×2), 7.2–7.6 (8H, br, Ar—H), 3.80 (2H, br, NCH×2), 3.59 (8H, N(CH$_2$)$_2$×2), 3.0–3.2 (4H, br, NCH$_2$×2), 0.8–2.2 (38H, m) Elemental analysis (for C$_{42}$H$_{62}$N$_6$O$_2$·2HCl.2H$_2$O) Calculated (%): C, 63.70; H, 8.65; N, 10.61. Found (%): C, 63.70; H, 8.34; N, 10.63.

Example 14-2

Trans-1,4-bis[[1-cyclohexyl-3-(4-homopiperidinophenyl)ureido]methyl]cyclohexane

The title compound was synthesized by the method in accordance with Example 1.

mp: 132°–135° C. (dihydrochloric acid salt) MS(FAB): m/e=739 (M$^+$+1) IR(KBr) v MAX: 2918(brs), 1655(s), 1518(s) NMR(DMSO-d$_6$) δ: 7.87 (2H, br, NH×2), 6.8–7.4 (8H, br, Ar—H), 3.80 (2H, br, NCH×2), 3.4–3.7 (8H, m, N(CH$_2$)$_2$×2), 3.0–3.2 (4H, br, NCH$_2$×2), 0.8–1.8 (46H, m) Elemental analysis (for C$_{42}$H$_{70}$N$_6$O$_2$·2HCl.2H$_2$O) Calculated (%): C, 65.15; H, 9.03; N, 9.91. Found (%): C, 65.43; H, 9.02; N, 9.95.

Example 14-3

Trans-1,4-bis[[1-cyclohexyl-3-(4-heptamethyleneiminophenyl)ureido]methyl]cyclohexane The title compound was synthesized by the method in accordance with Example 1.

mp: 126°–130° C. (dihydrochloric acid salt) MS(FAB): m/e=767 (M$^+$+1) IR(KBr) v MAX: 292Z(brs), 1635(s), 1522(s) NMR(DMSO-d$_6$) δ: 7.95 (2H, br, NH×2), 7.2–7.6 (8H, br, Ar—H), 3.78 (2H, br, NCH×2), 3.49 (8H, m, N(CH$_2$)$_2$×2), 3.0–3.2 (4H, br, NCH$_2$×2), 0.8–2.0 (50H, m) Elemental analysis (for C$_{48}$H$_{74}$N$_6$O$_2$·2HCl.5/2H$_2$O) Calculated (%): C, 64.47; H, 9.06; N, 9.81. Found (%): C, 64.28; H, 8.79; N, 9.79.

Example 14-4

Trans-1,4-bis[[1-cyclohexyl-3-(4-morpholinophenyl)ureido]methyl]cyclohexane

The title compound was synthesized by the method in accordance with Example 1.

mp: 156°–158° C. (dihydrochloric acid salt) MS(FAB): m/e=715 (M$^+$+1) IR(KBr) v MAX: 2929(brs), 1641(s), 1518(s) NMR(DMSO-d$_6$) δ: 8.18 (2H, br, NH×2), 7.3–7.6 (8H, br, Ar—H), 3.97 (8H, brs, O(CH$_2$)$_2$×2), 3.80 (2H, m, NCH×2), 3.35 (8H, brs, N(CH$_2$)$_2$×2), 3.08 (4H, d, J=6.9 Hz, NCH$_2$×2), 0.8–1.8 (30H, m) Elemental analysis (for C$_{42}$H$_{62}$N$_6$O$_4$·2HCl.3H$_2$O) Calculated (%): C, 59.92; H, 8.38; N, 9.98. Found (%): C, 59.80; H, 8.09; N, 9.96.

Example 14-5

Trans-1,4-bis[[1-cyclohexyl-3-(4-methylpiperadinophenyl)ureido]methyl]cyclohexane The title compound was synthesized by the method in accordance with Example 1.

mp: 205°–212° (tetrahydrochloric acid salt) MS(FAB): m/e=741 (M$^+$+1) IR(KBr) v MAX: 2929(brs), 1630(s), 1520(s) NMR(DMSO-d$_6$) δ: 7.86 (2H, br, NH×2), 7.30 (4H, d, J=8.8 Hz, Ar—H), 6.87 (4H, d, J=8.8 Hz, Ar—H), 3.0–3.8

(22H, m), 2.79 (6H, s, NCH$_2$×3), 0.8–1.8 (30H, m) Elemental analysis (for C$_{44}$H$_{68}$N$_8$O$_2$.4HCl.2H$_2$O) Calculated (%): C, 57.26; H, 8.08; N, 12.14. Found (%): C, 57.26; H, 8.00; N, 11.94.

Example 14-6

Trans-1,4-bis[[1-cyclohexyl-3-(4-diisobutylaminophenyl)ureido]methyl]cyclohexane The title compound was synthesized by the method in accordance with Example 2.

mp: 140°–142° C. (dihydrochloric acid salt) MS(FAB): m/e=799 (M$^+$+1) IR(KBr) ν MAX: 2931(brs), 1627(s), 1520(s) NMR(DMSO-d$_6$) δ: 8.20 (2H, br, NH×2), 7.2–7.6 (8H, br, Ar—H), 3.80 (2H, br, NCH×2), 3.4–3.7 (8H, m, N(CH$_2$)$_2$×3.0–3.2 (4H, br, NCH$_2$×2), 0.8–2.2 (58H, m) Elemental analysis (for C$_{50}$H$_{82}$N$_6$O$_2$.2HCl.2H$_2$O) Calculated (%): C, 66.13; H, 9.77; N, 9.25. Found (%): C, 66.37; H, 10.01; N, 9.20.

Example 14-7

Trans-1,4-bis[[1-cyclohexyl-3-(4-dinormalpropylaminophenyl)ureido]methyl]cyclohexane The title compound was synthesized by the method in accordance with Example 2.

mp: 147°–150° C. (dihydrochloric acid salt) MS(FAB): m/e=743 (M$^+$+1) IR(KBr) ν MAX: 2925(brs), 1637(s), 1518(s) NMR(DMSO-d$_6$) δ: 8.18 (2H, br, NH×2), 7.2–7.6 (8H, br, Ar—H), 3.78 (2H, br, NCH×2), 3.4–3.7 (8H, m, N(CH$_2$)$_2$×2), 3.0–3.2 (4H, br, NCH$_2$×2), 0.8–1.8 (50H, m) Elemental analysis (for C$_{46}$H$_{74}$N$_6$O$_2$.2HCl.4H$_2$O) Calculated (%): C, 62.21; H, 9.53; N, 9.46. Found (%): C, 62.10; H, 9.70; N, 9.46.

Example 14-8

Trans-1,4-bis[[1-cyclohexyl-3-(4-aminophenyl)ureido]methyl]cyclohexane

A 0.6 g quantity of 10% palladium carbon was added to 100 ml of a DMF solution containing 5.7 g of trans-1,4-bis[[1-cyclohexyl-3-(4-nitrophenyl)ureido]-metyl]cyclohexane synthesized in accordance with Example 2. Hydrogen was added at ordinal pressure and normal temperature for 15 hours. After completion of the reaction, palladium was separated by filtration and the reaction mixture was concentrated under reduced pressure. The reaction mixture was dissolved in chloroform and a 4N hydrochloric acid-dioxyane solution was added to provide 5.5 g (95%) of white crystals precipitated.

mp: 185°–188° C. (dihydrochloric acid salt) MS(FAB): m/e=575 (M$^+$+1) IR(KBr) ν MAX: 2927(brs), 1520(s) NMR (DMSO-d$_6$) δ: 9.92 (6H, br, N+H$_2$×2), 8.22 (2H, brs, NH×2), 7.50 (4H, d, J=8.8 Hz, Ar—H), 7.20 (4H, d, J=8.8 Hz, Ar—H), 3.79 (2H, m, NCH×2), 3.08 (4H, d, J=7.3 Hz, NCH$_2$×2), 0.8–1.8 (30H, m) Elemental analysis (for C$_{34}$H$_{50}$N$_6$O$_2$.2HCl.2H$_2$O) Calculated (%): C, 59.73; H, 8.26; N, 12.29. Found (%): C, 59.49; H, 8.55; N, 12.41.

Example 14-9

Trans-1,4-bis[[1-cyclohexyl-3-(4-acetaminophenyl)ureido]methyl]cyclohexane

A 0.25 g quantity of acetic anhydride and 0.25 g of triethylamine were added to 100 ml of a chloroform solution containing 0.58 g of trans-1,4-bis[[1-cyclohexyl-3-(4-aminophenyl)ureido]metyl]cyclohexane (free form) obtained in Example 14–8, and stirred at normal temperature for 3 hours. After completion of the reaction, the reaction mixture was concentrated under reduced pressure and distilled water was added to the residue. The crystals precipitated were washed with ether and dried under reduced pressure to provide 0.60 g (90%) of white crystals.

mp: 228°–231° C. MS(FAB): m/e=658 (M$^+$) IR(KBr) ν MAX: 2927(brs), 1637(s), 1512(s) NMR(DMSO-d$_6$) δ: 8.20 (2H, br, NH×2), 7.2–7.5 (8H, br, Ar—H), 3.76 (2H, m, NCH×2), 3.05 (4H, d, J=6.9HZ, NCH$_2$×2), 1.99 (6H, s, NCH$_3$), 0.8–1.8 (30H, m) Elemental analysis (for C$_{38}$H$_{54}$N$_6$O$_4$) Calculated (%): C, 69.27; H, 8.26; N, 12.76. Found (%): C, 69.43; H, 8.41; N, 12.59.

Example 14-10

Trans-1,4-bis[[1-cyclohexyl-3-(4-imidazolophenyl)ureido]methyl]cyclohexane

The title compound was synthesized by the method in accordance with Example 1.

mp: 253°–260° C. (dihydrochloric acid salt) MS(FAB): m/e=677 (M$^+$+1) IR(KBr) ν MAX: 2866(brs), 1635(s), 1525(s) NMR(DMSO-d$_6$) δ: 8.1–8.5 (4H, m), 7.5–7.6 (10H, br), 6.47 (2H, s, imidazolyl-H×2), 3.80 (2H, m, NCH×2), 3.09 (4H, d, J=7.3HZ, NCH$_2$×2), 0.8–2.2 (30H, m) Elemental analysis (for C$_{40}$H$_{52}$N$_8$O$_2$.2HCl.3/2H$_2$O) Calculated (%): C, 61.85; H, 7.14; N, 14.43. Found (%): C, 62.03; H, 7.01; N, 14.52.

Example 14-11

Trans-1,4-bis[[1-cyclohexyl-3-(4-ethylmethylaminophenyl)ureido]methyl]cyclohexane The title compound was synthesized by the method in accordance with Example 2.

mp: 151°–153° (dihydrochloric acid salt) MS(FAB): m/e= 659 (M$^+$+1) IR(KBr) ν MAX: 2927(brs), 1635(s), 1515(s) NMR(DMSO-d$_6$) δ: 8.26 (2H, br, NH×2), 7.2–7.7 (8H, m, Ar—H), 3.79 (2H, m, NCH×2), 3.48 (4H, m, NCH$_2$×2), 3.0–3.2 (10H, br), 0.8–1.8 (36H, m) Elemental analysis (for C$_{40}$H$_{62}$N$_6$O$_2$.2HCl.2H$_2$O) Calculated (%): C, 62.57; H, 8.93; N, 10.95. Found (%): C, 62.39; H, 9.15; N, 10.86.

Example 14-12

Trans-1,4-bis[[1-cyclohexyl-3-(4-methylpropylaminophenyl)ureido]methyl]cyclohexane The title compound was synthesized by the method in accordance with Example 2.

mp: 151°–153° (dihydrochloric acid salt) MS(FAB): m/e= 687 (M$^+$+1) IR(KBr) ν MAX: 2929(brs), 1631(s), 1522(s) NMR(DMSO-d$_6$) δ: 8.30 (2H, br, NH×2), 7.2–7.5 (8H, m, Ar—H), 3.80 (2H, br, NCH×2), 3.3–3.5 (4H, m, NCH$_2$×2), 3.0–3.2 (10H, br, NCH$_2$×2), 0.8–1.8 (40H, m) Elemental analysis (for C$_{42}$H$_{66}$N$_6$O$_2$.2HCl.2H$_2$O) Calculated (%): C, 63.38; H, 9.12; N, 10.56. Found (%): C, 63.70; H, 8.98; N, 10.24.

Example 15

Trans-1,4-bis[[1-cycloheptyl-3-(4-dimethylaminophenyl)ureido]methyl]cyclohexane

The title compound was synthesized by the method in accordance with Example 1.

mp: 159°–164° C. (dihydrochloric acid salt) MS(FAS): m/e=659 (M⁺+1) IR(KBr) ν MAX: 2917(brs), 1643(s), 1631(s), 1513(s) NMR(DMSO-d₆) δ: 8.26 (2H, s, NH×2), 7.4–7.7 (8H, m, Ar—H), 3.78 (2H, m, NCH×2), 3.0–3.2 (4H, m, NCH₂×2), 3.06 (12H, s, N(CH₃)₂×2), 1.3–1.8 (30H, m, CH₂×15), 0.8–1.0 (4H, m, CH₂×2) Elemental analysis (for C₄₀H₆₂N₆O₂.2HCl.3H₂O) Calculated (%): C, 61.13; H, 8.98; N, 10.69. Found (%): C, 61.28; H, 9.16; N, 10.92.

Example 16

Trans-1,4-bis[[1-cycloheptyl-3-(4-piperidinophenyl)ureido]methyl]cyclohexane

The title compound was synthesized by the method in accordance with Example 1.

mp: 175°–178° C. (dihydrochloric acid salt) MS(FAB): m/e=738 (M⁺+1) IR(KBr) ν MAX: 2927(brs), 1646(s), 1637(s), 1515(s) NMR(DMSO-d₆) δ: 8.29 (2H, brs, NH×2), 7.5–7.7 (8H, m, Ar—H), 3.78 (2H, m, NCH×2), 3.2–3.6 (8H, br, NCH₂×2), 3.09 (4H, d, J=7.0 Hz, NCH₂×2), 1.4–2.4 (42H, m), 0.90 (4H, m) Elemental analysis (for C₄₆H₇₀N₆O₂.2HCl.H₂O) Calculated (%): C, 66.56; H, 8.99; N, 10.13. Found (%): C, 66.48; H, 9.23; N, 10.08.

Example 17

Trans-1,4-bis[[1-cycloheptyl-3-(3-dimethylaminophenyl)ureido]methyl]cyclohexane

The title compound was synthesized by the method in accordance with Example 1.

mp: 151°–156° C. (dihydrochloric acid salt) MS(FAB): m/e=659 (M⁺+1) IR(KBr) ν MAX: 2919(brs), 1641(s), 1604(s), 1506(s) NMR(DMSO-d₆) δ: 8.32 (2H, brs, NH×2), 7.74 (2H, brs, Ar—H), 7.1–7.4 (6H, m, Ar—H), 3.80 (2H, m, NCH×2), 3.09 (4H, d, J=7.3 Hz, NCH₂×2), 3.04 (12H, s, N(CH₃)₂×2), 1.4–1.8 (30H, m), 0.91 (4H, m) Elemental analysis (for C₄₀H₆₂N₆O₂.2HCl.H₂O) Calculated (%): C, 64.07; H, 8.87; N 11.21. Found (%): C, 64.32; H, 9.10; N, 10.98.

Example 18

Trans-1,4-bis[[1-cycloheptyl-3-(4-diethylaminophenyl)ureido]methyl]cyclohexane

The title compound was synthesized by the method in accordance with Example 1.

mp: 170°–175° C. (dihydrochloric acid salt) MS(FAB): m/e=715 (M⁺+1) IR(KBr) ν MAX: 2925(brs), 1639(s), 1612(s), 1515(s) NMR(DMSO-d₆) δ: 8.33 (2H, brs, NH×2), 7.61 (8H, brs, Ar—H), 3.78 (2H, m, NCH×2), 3.3–3.6 (8H, br, NCH₂×4), 3.09 (4H, d, J=7.3 Hz, NCH₂×2), 1.4–1.9 (30H, m), 1.04 (12H, t, J=7.0 Hz, CH₂×2), 0.91 (4H, m) Elemental analysis (for C₄₄H₇₀N₆O₂.2HCl.H₂O) Calculated (%): C, 65.57; H, 9.25; N, 10.43. Found (%): C, 65.32; H, 9.51; N, 10.18.

Example 18-1

Trans-1,4-bis[[1-cycloheptyl-3-(4-pyrrolidinophenyl)ureido]methyl]cyclohexane

The title compound was synthesized by the method in accordance with Example 1.

mp: 152°–155° C. (dihydrochloric acid salt) MS(FAB): m/e=711 (M⁺+1) IR(KBr) ν MAX: 2931(brs), 1633(s), 1530(s) NMR(DMSO-d₆) δ: 8.29 (2H, brs, NH×2), 7.5–7.7 (8H, brs, Ar—H), 3.78 (2H, m, NCH×2), 3.5–3.7 (8H, m, N(CH₂)₂×2), 3.0–3.2 (4H, br, NCH₂×2), 0.9–2.2 (38H, m) Elemental analysis (for C₄₄H₆₆N₆O₂.2HCl.22H₂O) Calculated (%): C, 64.45; H, 8.85; N, 10.25. Found (%): C, 64.77; H, 9.04; N, 10.43.

Example 19

Trans-1,4-bis[[1-cycloheptyl-3-(6-quinoline)ureido]methyl]cyclohexane

The title compound was synthesized by the method in accordance with Example 1.

mp: 181°–184° C. (dihydrochloric acid salt) MS(FAB): m/e=675 (M⁺+1) IR(KBr) ν MAX: 2927(brs), 1644(s), 1533(s) NMR(DMSO-d₆) δ: 9.00 (2H, dd, J=5.1, 1.5 Hz, Ar—H), 8.90 (4H, m, Ar—H), 8.41 (2H, brs, NH×2), 8.10–8.30 (4H, m, Ar—H), 7.90 (2H, dd, J=8.4, 5.1 Hz, Ar—H), 3.84 (2H, m, NCH×2), 3.18 (4H, d, J=7.3 Hz, NCH₂×2), 1.4–1.9 (30H, m), 0.95 (4H, m) Elemental analysis (for C₄₂H₅₄N₆O₂.2HCl.H₂O) Calculated (%): C, 65.87; H, 7.63; N, 10.97. Found (%): C, 66.08; H, 7.90; N, 10.60.

Example 20

Trans-1,4-bis[[1-cycloheptyl-3-(1-methylindoli-5-ne)ureido]methyl]cyclohexane

The title compound was synthesized by the method in accordance with Example 1.

mp: 150°–153° C. (dihydrochloric acid salt) MS(FAB): m/e=682 (M++1) IR(KBr) ν MAX: 2919(brs), 1641(s), 1536(s) NMR(DMSO-d₆) δ: 8.03 (2H, brs, NH×2), 7.42 (2H, brs, Ar—H), 7.27(2H, brs, Ar—H), 7.05 (2H, brs, Ar—H), 3.76 (2H, brs, NCH×2), 2.8–3.2 (14H, m, NCH₂×2, NCH₂CH₂×2), 1.4–1.8 (30H, m), 0.90 (4H, m) Elemental analysis (for C₄₂H₆₂N₆O₂.2HCl.2H₂O) Calculated (%): C, 63.70; H, 8.65; N, 10.61. Found (%): C, 63.90; H, 8.89; N, 10.40.

Example 21

Trans-1,4-bis[[1-cycloheptyl-3-(4-dimethylaminophenyl)ureido]methyl]cyclohexane

The title compound was synthesized by the method in accordance With Example 1.

mp: 172°–176° C. (maleic acid salt) MS(FAB): m/e=659 (M⁺⁺1) IR(KBr) ν MAX: 2929(brs), 1630(s), 1521(s) NMR (DMSO-d₆) δ: 7.67 (2H, brs, NH×2), 7.22 (4H, d, J=9.2 Hz, Ar—H), 6.71 (4H, d, J=8.4 Hz, Ar—H), 6.19 (2H, s, =CH×2), 3.74 (2H, m, NCH×2), 3.03 (4H, d, J=7.3 Hz, NCH₂×2), 2.85 (12H, s, N(CH₃)₂×2), 1.45–1.75 (30H, m), 0.91 (4H, m) Elemental analysis (for C₄₀H₆₂N₆O₂.C₄H₄O₄) Calculated (%): C, 68.19; H, 8.58; N, 10.84. Found (%): C, 68.45; H, 8.91; N, 11.03.

Example 22

Trans-1,4-bis[[1-cycloheptyl-3-(4-dimethyaminophenyl)ureido]methyl]cyclohexane

The title compound was synthesized by the method in accordance with Example 1.

mp: 198°–202° C. (fumaric acid salt) MS(FAB): m/e=658 (M⁺) IR(KBr) ν MAX: 2924(brs), 1626(s), 1520(s) NMR (DMSO-d₆) δ: 7.61 (2H, brs, NH×2), 7.18 (4H, brs, Ar—H), 6.62 (4H, brs, Ar—H), 6.56 (2H, s, =CHx2), 3.76 (2H, m, NCH×2), 3.02 (4H, d, J=7.3 Hz, NCH₂×2), 2.81 (12H, s, N(CH$_3$)$_2$×2), 1.44–1.73 (30H, m), 0.91 (4H, m) Elemental analysis (for C$_{40}$H$_{62}$N$_6$O$_2$.C$_4$H$_4$O$_4$) Calculated (%): C, 68.19; H, 8.58; N, 10.84. Found (%): C, 68.30; H, 8.70; N, 10.56.

Example 23

Trans-1,4-bis[[1-cycloheptyl-3-(4-dimethyaminophenyl)ureido]methyl]cyclohexane

The title compound was synthesized by the method in accordance with Example 1.

mp: 218°–222° C. (dioxalic acid salt) MS(FAB): m/e=659 (M$^+$+1) IR(KBr) ν MAX: 2926(brs), 1633(s), 1520(s) NMR (DMSO-d$_6$) δ: 7.64 (2H, brs, NH×2), 7.20 (4H, d, J=9.2 Hz, Ar—H), 6.67 (4H, d, J=9.2 Hz, Ar—H), 3.75 (2H, m, NCH×2), 3.03 (4H, d, J=7.3 Hz, NCH$_2$×2), 2.82 (12H, s, N(CH$_3$)$_2$×2), 1.44–1.75 (30H, m), 0.91 (4H, m) Elemental analysis (for C$_{40}$H$_{62}$N$_6$O$_2$.2C$_2$H$_2$O$_4$.H$_2$O) Calculated (%): C, 62.71; H, 7.79; N, 9.54. Found (%): C, 62.51; H, 8.26; N, 9.90.

Example 24

Trans-1,4-bis[[1-cycloheptyl-3-(4-dimethyaminophenyl)ureido]methyl]cyclohexane

The title compound was synthesized by the method in accordance with Example 1.

mp: 112°–117° C. (dimethanesulfonic acid salt) MS(FAB): m/e=658 (M$^+$) IR(KBr) ν MAX: 2929(brs), 1637(s), 1518(s) NMR(DMSO-d$_6$) δ: 8.24 (2H, brs, NH×2), 7.55 (4H, d, J=9.2 Hz, Ar—H), 7.43 (4H, d, J=9.2 Hz, Ar—H), 3.77 (2H, m, NCH×2), 3.13 (12H, s, N(CH$_3$)$_2$×2), 3.08 (4H, d, J=7.3 Hz, NCH$_2$×2), 2.39 (6H, s, SCH$_2$×2), 1.45–1.75 (3OH, m), 0.91 (4H, m) Elemental analysis (for C$_{40}$H$_{62}$N$_6$O$_2$.2CH$_4$O$_3$S.6H$_2$O) Calculated (%): C, 52.59; H, 8.62; N, 8.76. Found (%): C, 52.44; H, 8.72; N, 8.65.

Example 25

Trans-1,4-bis[[1-cycloheptyl-3-(4-dimethyaminophenyl)ureido]methyl]cyclohexane

The title compound was synthesized by the method in accordance with Example 1.

mp: 142°–146° C. (di-p-toluenesulfonic acid salt) MS(FAB): m/e=658 (M$^+$) IR(KBr) ν MAX: 2929(brs), 1637(s), 1517(s) NMR(DMSO-d$_6$) δ: 8.21 (2H, brs, NH×2), 7.52 (8H, m, Ar—H), 7.43 (4H, d, J=8.8 Hz, Ar—H), 7.10 (4H, d, J=8.8 Hz, Ar—H), 3.76 (2H, m, NCH×2), 3.11 (12H, s, N(CH$_3$)$_2$×2), 3.07 (4H, d, J=7.3 Hz, NCH$_2$×2), 2.28 (6H, Ph—CH$_2$×2), 1.42–1.74 (30H, m), 0.90 (4H, m) Elemental analysis (for C$_{40}$H$_{62}$N$_6$O$_2$.2C$_7$H$_8$O$_3$S.2H$_2$O) Calculated (%): C, 62.40; H, 7.95; N, 8.09. Found (%): C, 62.64; H, 8.20; N, 7.83.

Example 26

Trans-1,4-bis[[1-cyclooctyl-3-(4-dimethyaminophenyl)ureido]methyl]cyclohexane

The title compound was synthesized by the method in accordance with Example 1.

mp: 194°–196° C. (dihydrochloric acid salt) MS(FAB): m/e=687 (M$^+$+1) IR(KBr) ν MAX: 2921(brs), 1648(s), 1519(s) NMR(DMSO-d$_6$) δ: 8.17 (2H, s, NH×2), 7.52 (8H, s, Ar—H), 3.78 (2H, s, NCH×2), 3.0–3.1 (16H, NCH$_2$×2, N(CH$_3$)$_2$×2), 1.4–1.9 (34H, m), 0.8–1.0 (4H, m) Elemental analysis (for C$_{42}$H$_{66}$N$_6$O$_2$.2HCl.H$_2$O) Calculated (%): C, 64.84; H, 9.07; N, 10.80. Found (%): C, 64.50; H, 9.00; N, 10.70.

Example 27

Trans-1,4-bis[[3-(4-dimethyaminophenyl)-1-(2-norbornyl)ureido]methyl]cyclohexane The title compound was synthesized by the method in accordance with Example 2.

mp: 174°–178° C. (free form) MS(FAB): m/e=655 (M$^+$+1) IR(KBr) ν MAX: 2954(s), 1625(s), 1590(s), 1519(s) NMR(DMSO-d$_6$) δ: 7.66 (2H, s, NH×2), 7.19 (4H, d, J=9.0 Hz, Ar—H), 6.62 (4H, d, J=9.0 Hz, Ar—H), 3.70 (2H, m, NCH×2), 3.0–3.4 (4H, m, NCH$_2$×2), 2.81 (12H, s, N(CH$_3$)$_2$×2), 0.8–2.3 (30H, m) Elemental analysis (for C$_{40}$H$_{58}$N$_6$O$_2$.3H$_2$O) Calculated (%): C, 67.76; H, 9.10; N, 11.85. Found (%): C, 67.69; H, 8.86; N, 11.66.

Example 28

Trans-1,4-bis[[3-(4-dimethylaminophenyl)-1-(4-methylcyclohexyl)ureido]methyl]cyclohexane The title compound was synthesized by the method in accordance with Example 1.

mp: 150°–153° C. (dihydrochloric acid salt) MS(FAB): m/e=658 (M$^+$) IR(KBr) ν MAX: 2923(brs), 1637(s), 1519(s) NMR(DMSO-d$_6$) δ: 8.24 (2H, S, NH×2), 7.4–7.7 (8H, S, Ar—H), 3.6–3.9 (2H, m, NCH×2), 3.0–3.2 (16H, br, NCH$_2$×2, N(CH$_3$)$_2$×2), 0.8–1.9 (34H, m) Elemental analysis (for C$_{40}$H$_{62}$N$_6$O$_2$.2HCl.2H$_2$O) Calculated (%): C, 62.56; H, 8.93; N, 10.94. Found (%): C, 62.31; H, 8.80; N, 10.90.

Example 28-1

Trans-1,4-bis[[3-(4-dimethylaminophenyl)-1-(4-methylcyclohexyl)ureido]methyl]cyclohexane The title compound was synthesized by the method in accordance with Example 1.

mp: 148°–155° C. (dihydrochloric acid salt) MS(FAB): m/e=715 (M$^+$) IR(KBr) ν MAX: 2931(brs), 1631(s), 1532(s) NMR(DMSO-d$_6$) δ: 8.39 (2H, s, NH×2), 7.2–7.6 (8H, br, Ar—H), 3.4–3.9 (10H, m, NCH×2, N(CH$_2$)$_2$×2), 3.0–3.2 (4H, br, NCH$_2$×2), 0.8–1.8 (46H, m) Elemental analysis (for C$_{44}$H$_{70}$N$_6$O$_2$.2HCl.2H$_2$O) Calculated (%): C, 64.14; H, 9.30; N, 10.20. Found (%): C, 64.21; H, 9.19; N, 10.16.

Example 28-2

Trans-1,4-bis[[1-(4-methylcyclohexyl)-3-(4-pyrrolidinophenyl)ureido]methyl]cyclohexane The title compound was synthesized by the method in accordance with Example 1.

mp: 149°–155° C. (dihydrochloric acid salt) MS(FAB): m/e=711 (M$^+$) IR(KBr) ν MAX: 2939(brs), 1635(s), 1538(s) NMR(DMSO-d$_6$) δ: 8.20 (2H, s, NH×2), 7.2–7.6 (8H, br, Ar—H), 3.4–3.9 (10H, m, NCH×2, N(CH$_2$)$_2$×2), 3.0–3.2 (4H, br, NCH$_2$×2), 0.8–2.2 (42H, m) Elemental analysis (for C$_{44}$H$_{66}$N$_6$O$_2$.2HCl.2H$_2$O) Calculated (%): C, 64.45; H, 8.85; N, 10.25. Found (%): C, 64.23; H, 8.60; N, 10.08.

Example 28-3

Trans-1,4-bis[[1-(4-methylcyclohexyl)-3-(4-piperidinophenyl)ureido]methyl]cyclohexane The title compound was synthesized by the method in accordance with Example 1.

mp: 161°–165° C. (dihydrochloric acid salt) MS(FAB) m/e=739 (M⁺) IR(KBr) ν MAX: 2935(brs), 1633(s), 1531(s) NMR(DMSO-$d_6$) δ: 8.29 (2H, brs, NH×2), 7.3–7.7 (8H, br, Ar—H), 3.2–3.9 (10H, m, NCH×2, N(CH$_2$)$_2$×2), 3.0–3.2 (4H, br, NCH$_2$×2), 0.8–1.8 (46H, m) Elemental analysis (for $C_{44}H_{66}N_6O_2$·2HCl·2H$_2$O) Calculated (%): C, 65.15; H, 9.03; N, 9.91. Found (%): C, 64.95; H, 8.82; N, 10.01.

Example 29

Trans-1,4-bis[[1-(2-adamantyl)-3-(4-dimethylaminophenyl)ureido]methyl]cyclohexane The title compound was synthesized by the method in accordance with Example 5.

mp: 182°–185° C. (free form) MS(FAB): m/e=735 (M⁺+1) IR(KBr) ν MAX: 2908(brs), 1627(s), 1589(s), 1519(s) NMR(DMSO-$d_6$) δ: 8.24 (2H, s, NH×2), 7.19 (4H, d, J=9.2 Hz, Ar—H), 6.63 (4H, d, J=9.2 Hz, Ar—H), 3.64 (2H, s, NCH×2), 3.15 (4H, br, NCH$_2$×2), 2.80 (12H, s, N(CH$_3$)$_2$×2), 2.23 (4H, m), 1.4–1.9 (30H, m), 0.7–0.9 (4H, m) Elemental analysis (for $C_{46}H_{66}N_6O_2$·3H$_2$O) Calculated (%): C, 71.65; H, 9.15; N, 10.90. Found (%): C, 71.69; H, 9.63; N, 10.39.

Example 30

Trans-1,4-bis[[1-benzyl-3-(4-dimethylaminophenyl) ureido]methyl]cyclohexane

The title compound was synthesized by the method in accordance with Example 1.

mp: 142°–144° C. (dihydrochloric acid salt) MS(FAB): m/e=647 (M⁺+1) IR(KBr) ν MAX: 2921(brs), 1646(s), 1519(s) NMR(DMSO-$d_6$) δ: 8.55 (2H, s, NH×2), 7.5–7.7 (8H, brs, Ar—H), 7.2–7.35 (10H, m, Ar—H), 4.59 (4H, brs, Ph—CH$_2$×2), 3.0–3.3 (16H, N(CH$_3$)$_2$×5, NCH$_2$×2), 1.5–1.7 (6H, m), 0.8–1.0 (4H, m) Elemental analysis (for $C_{40}H_{50}N_6O_2$·2HCl) Calculated (%): C, 66.75; H, 7.28; N, 11.68. Found (%): C, 66.50; H, 7.00; N, 11.40.

Example 31

Trans-1,4-bis[[3-(4-dimethylaminophenyl)-1-(2-phenetyl)ureido]methyl]cyclohexane The title compound was synthesized by the method in accordance with Example 1.

mp: 203°–205° C. (dihydrochloric acid salt) MS(FAB): m/e=675 (M⁺+1) IR(KBr) ν MAX: 2925(brs), 1664(s), 1533(s) NMR(DMSO-$d_6$) δ: 8.34 (2H, s, NH×2), 7.56 (8H, br, Ar—H), 7.1–7.3 (10H, m, Ar—H), 3.54 (4H, t, J=7.5 Hz, NCH$_2$×2), 3.13 (4H, d, J=7.0 Hz, NCH$_2$×2), 3.06 (12H, N(CH$_3$)$_2$×2), 2.80 (4H, t, J=7.5 Hz, Ph—CH$_2$×2) Elemental analysis (for $C_{42}H_{54}N_6O_2$·2HCl·H$_2$O) Calculated (%): C, 65.87; H, 7.63; N, 10.97. Found (%): C, 66.06; H, 7.41; N, 11.07.

Example 32

Trans-1,4-bis[[3-(4-dimethylaminophenyl)-1-[2-(1-cyclohexenyl)ethyl]ureido]methyl]cyclohexane The title compound was synthesized by the method in accordance with Example 1.

mp: 208°–210° C. (dihydrochloric acid salt) MS(FAB): m/e=683 (M⁺+1) IR(KBr) ν MAX: 2923(brs), 1637(s), 1519(s) NMR(DMSO-$d_6$) δ: 8.42 (2H, brs, NH×2), 7.5–7.7 (8H, br, Ar—H), 5.40 (2H, brs, =CH×2), 3.0–3.6 (20H, br, NCH$_2$×2, NCH$_2$×2, N(CH$_3$)$_2$×2), 0.9–2.2 (30H, m) Elemental analysis (for $C_{42}H_{62}N_6O_2$·2HCl·3/2H$_2$O) Calculated (%): C, 64.43; H, 8.63; N, 10.73. Found (%): C, 64.62; H, 8.82; N, 10.79.

Example 33

Trans-1,4-bis[[3-(4-dimethylaminophenyl)-1-furfurylureido]methyl]cyclohexane

The title compound was synthesized by the method in accordance with Example 2.

mp: 195°–199° C. (free form) MS(FAB): m/e=627 (M⁺+1) IR(KBr) ν MAX: 2884(brs), 1619(s), 1594(s), 1519(s) NMR(DMSO-$d_6$) δ: 7.88 (2H, s, NH×2), 7.53 (2H, s, Ar—H), 7.21 (4H, 6.37 (2H, m, Ar—H), 6.27 (2H, m, Ar—H), 4.51 (4H, s, NH$_2$×2), 3.15 (4H, d, J=7.3 Hz, NCH$_2$×2), 2.82 (12H, s, N(CH$_3$)$_2$×2), 1.5–1.7 (6H, m), 0.8–1.0 (4H, m) Elemental analysis (for $C_{36}H_{46}N_6O_4$) Calculated (%): C, 68.99; H, 7.40; N, 13.41. Found (%): C, 68.96; H, 7.72; N, 13.85.

Example 34

Cis-1,4-bis[[3-(4-dimethylaminophenyl)-1-normalheptylureido]methyl]cyclohexane

The title compound was synthesized by the method in accordance with Example 1.

mp: 112°–114° C. (free form) MS(FAB): m/e=663 (M⁺+1) IR(KBr) ν MAX: 2925(brs), 1617(s), 1521(s) NMR (DMSO-$d_6$) δ: 7.69 (2H, s, NH×2), 7.21 (4H, d, J=9.2 Hz, Ar—H), 6.62 (4H, d, J=9.2 Hz, Ar—H), 3.1–3.3 (8H, m, NCH$_2$×4), 2.81 (12H, s, N(CH$_3$)$_2$×2), 1.77 (2H, brs), 1.2–1.6 (28H, m), 0.86 (6H, t, J=7.0 Hz, CH$_2$×2) Elemental analysis (for $C_{40}H_{66}N_6O_2$) Calculated (%): C, 72.46; H, 10.03; N, 12.68. Found (%): C, 72.80; H, 10.24; N, 12.80.

Example 35

Cis-1,4-bis[[3-(4-dimethylaminophenyl)-1-normaloctylureido]methyl]cyclohexane

The title compound was synthesized by the method in accordance with Example 1.

mp: 105°–107° C. (free form) MS(FAB): m/e=690 (M⁺) IR(KBr) ν MAX: 2921(brs), 1620(s), 1521(s) NMR (DMSO-$d_6$) δ: 7.67 (2H, s, NH×2), 7.20 (4H, d, J=9.2 Hz, Ar—H), 6.60 (4H, d, J=9.2 Hz, Ar—H), 3.1–3.3 (8H, m, NCH$_2$×4), 2.82 (12H, s, N(CH$_3$)$_2$×2), 1.78 (2H, brs), 1.2–1.6 (32H, m), 0.86 (6H, t, J=7.0 Hz, CH$_2$×2) Elemental analysis (for $C_{42}H_{70}N_6O_2$·1/2H$_2$O) Calculated (%): C, 72.06; H, 10.22; N, 12.01. Found (%): C, 72.16; H, 10.59; N, 11.94.

Example 36

Cis-1,4-bis[[3-(4-dimethylaminophenyl)-1-normalnonylureido]methyl]cyclohexane

The title compound was synthesized by the method in accordance with Example 1.

mp: 96°–98° (free form) MS(FAB): m/e=719 (M⁺+1) IR(KBr) ν MAX: 2913(brs), 1619(s), 1519(s) NMR (DMSO-$d_6$) δ: 7.71 (2H, s, NH×2), 7.22 (4H, d, J=9.0 Hz, Ar—H), 6.64 (4H, d, J=9.0 Hz, Ar—H), 3.1–3.3 (8H, m, NCH$_2$×4), 2.82 (12H, s, N(CH$_3$)$_2$×2), 1.77 (2H, brs, CH×2), 1.2–1.6 (36H, m), 0.85 (6H, t, J=6.6 Hz, CH$_2$×2) Elemental analysis (for $C_{44}H_{74}N_6O_2$·H$_2$O) Calculated (%): C, 71.70; H, 10.39; N, 11.40. Found (%): C, 71.91; H, 10.74; N, 11.29.

Example 37

Cis-1,4-bis[[3-(4-dimethylaminophenyl)-1-normaldecylureido]methyl]cyclohexane

The title compound was synthesized by the method in accordance with Example 1.

mp: 125°–127° (free form) MS(FAB): m/e=747 (M⁺+1) IR(KBr) ν MAX: 2915(brs), 1619(s), 1521(s) NMR (DMSO-d₆) δ: 7.71 (2H, s, NH×2), 7.22 (4H, d, J=9.1 Hz, Ar—H), 6.61 (4H, d, J=9.1 Hz, Ar—H), 3.1–3.3 (8H, m, NCH₂×4), 2.81 (12H, s, N(CH₃)₂), 1.77 (2H, brs, CH×2), 1.2–1.6 (40H, m, CH₂×20), 0.85 (6H, t, J=7.0 Hz, CH₂×2) Elemental analysis (for C₄₆H₇₈N₆O₂.3H₂O) Calculated (%): C, 68.96; H, 10.57; N, 10.49. Found (%): C, 68.79; H, 10.82; N, 10.60.

Example 38

Cis-1,4-bis[[3-(4-dimethylaminophenyl)-1-neopentylureido]methyl]cyclohexane

The title compound was synthesized by the method in accordance with Example 1.

mp: 178°–181° C. (dihydrochloric acid salt) MS(FAB): m/e=606 (M⁺) IR(KBr) ν MAX: 2933(brs), 1648(s), 1519(s) NMR(DMSO-d₆) δ: 8.52 (2H, s, NH×2), 7.5–7.6 (8H, m, ArH×2), 3.39 (4H, d, J=7.0 Hz, NCH₂×2), 3.20 (4H, NCH₂×2), 3.05 (12H, s), 1.82 (2H, brs), 1.1–1.3 (8H, m), 0.86 (18H, s, (CH₃)₂×2) Elemental analysis (for C₃₆H₅₃N₆O₂.2HCl.2H₂O) Calculated (%): C, 60.40; H, 9.01; N, 11.74. Found (%): C, 60.09; H, 9.17; N, 11.54.

Example 39

Cis-1,4-bis[1-cyclohexylmethyl-3-(4-dimethylaminophenyl)ureido]methyl]cyclohexane The title compound was synthesized by the method in accordance with Example 1.

mp: 172°–175° C. (dihydrochloric acid salt) MS(FAB): m/e=659 (M⁺+1) IR(KBr) ν MAX: 2925(brs), 1643(s), 1517(s) NMR(DMSO-d₆) δ: 8.40 (2H, s, NH×2), 7.4–7.7 (8H, s, Ar—H), 3.30 (4H, brs, NCH₂×2), 3.17 (4H, m, NCH₂×2), 3.06 (12H, s, N(CH₃)₂×2), 0.8–0.9 (32H, m) Elemental analysis (for C₄₀H₆₂N₆O₂.2HCl.2H₂O) Calculated (%): Cr 62.56; H, 8.93; N, 10.94. Found (%): C, 62.28; H, 8.75; N, 11.27.

Example 40

Cis-1,4-bis[[3-(4-dimethylaminophenyl)-1-(4-heptyl)ureido]methyl]cyclohexane

The title compound was synthesized by the method in accordance with Example 2.

mp: 180°–183° C. (free form) MS(FAB): m/e=663 (M⁺+1) IR(KBr) ν MAX: 3453(brs), 1620(s), 1592(s), 1519(s) NMR(DMSO-d₆) δ: 7.58 (2H, s, NH×2), 7.19 (4H, d, J=8.8 Hz, Ar—H), 6.62 (4H, d, J=8.8 Hz, Ar—H), 3.87 (2H, m, NCH×2), 3.07 (4H, d, J=7.0 Hz, NCH₂×2), 2.81 (12H, s, N(CH₃)₂×2), 1.2–1.8 (26H, m), 0.87 (12H, t, J=7.0 Hz, CH₃×4) Elemental analysis (for C₄₀H₆₆N₆O₂) Calculated (%): C, 72.46; H, 10.03; N, 12.68. Found (%): C, 72.83; H, 10.49; N, 12.64.

Example 41

Cis-1,4-bis[[1-cyclopentyl-3-(4-dimethylaminophenyl)ureido]methyl]cyclohexane

The title compound was synthesized by the method in accordance with Example 1.

mp: 162°–165° C. (dihydrochloric acid salt) MS(FAB): m/e=603 (M⁺+1) IR(KBr) ν MAX: 2917(brs), 1631(s), 1517(s) NMR(DMSO-d₆) δ: 8.37 (2H, s, NH×2), 7.4–7.6 (8H, brs, Ar—H), 4.11 (2H, m, NCH×2), 3.23 (4H, br, NCH₂×2), 3.06 (12H, brs, N(CH₃)₂×2), 1.3–1.8 (26H, m) Elemental analysis (for C₃₆H₅₄N₆O₂.2HCl.2H₂O) Calculated (%): C, 60.75; H, 8.50; N, 11.81. Found (%): C, 60.89; H, 8.44; N, 11.50.

Example 42

Cis-1,4-bis[[1-cyclohexyl-3-(4-dimethylaminophenyl)ureido]methyl]cyclohexane

The title compound was synthesized by the method in accordance with Example 1.

mp: 145°–147° C. (dihydrochloric acid salt) MS(FAB): m/e=631 (M⁺+1) IR(KBr) ν MAX: 2933(brs), 1635(s), 1517(s) NMR(DMSO-d₆) δ: 8.39 (2H, s, NH×2), 7.4–7.7 (8H, brs, Ar—H), 3.77 (2H, brs, NCH×2), 3.22 (4H, brs, NCH₂×2), 3.06 (12H, brs, N(CH₃) 2×2), 1.0–1.8 (30H, m) Elemental analysis (for C₃₈H₅₈N₆O₂.2HCl.2H₂O) Calculated (%): C, 61.69; H, 8.72; N, 11.36. Found (%): C, 61.70; H, 8.70; N, 10.90.

Example 43

Cis-1,4-bis[[1-cycloheptyl-3-(4-dimethylaminophenyl)ureido]methyl]cyclohexane

The title compound was synthesized by the method in accordance with Example 1.

mp: 160°–163° C. (dihydrochloric acid salt) MS(FAB): m/e=659 (M⁺+1) IR(KBr) ν MAX: 2929(brs), 1656(s), 1637(s), 1515(s) NMR(DMSO-d₆) δ: 8.36 (2H, s, NH×2), 7.4–7.7 (8H, m, Ar—H), 3.73 (2H, m, NCH×2), 3.23 (4H, d, J=7.0 Hz, NCH₂×2), 3.06 (12H, s, N(CH₃)₂×2), 1.3–1–9 (34H, m) Elemental analysis (for C₄₀H₆₂N₆O₂.2HCl.5/2H₂O) Calculated (%): C, 61.84; H, 8.95; N, 10.82. Found (%): C, 61.96; H, 8.65; N, 10.94.

Example 44

Cis-1,4-bis[[1-cyclooctyl-3-(4-dimethylaminophenyl)ureido]methyl]cyclohexane

The title compound was synthesized by the method in accordance with Example 1.

mp: 197°–200° C. (dihydrochloric acid salt ) MS(FAB): m/e=606 (M⁺) IR(KBr) ν MAX: 2927(brs), 1643(s)r 1523 (s) NMR(DMSO-d₆) δ: 8.10 (2H, brs, NH×2), 7.2–7.6 (8H, s, Ar—H), 3.72 (2H, m, NCH×2), 3.20 (4H, m), 3.01 (12H, s, N(CH₃)₂×2), 1.3–2.0 (38H, m) Elemental analysis (for C₄₂H₆₆N₆O₂.2HCl) Calculated (%): C, 66.38; H, 9.02; N, 11.06. Found (%): C, 66.25; H, 9.48; N, 10.97.

Example 45

Cis-1,4-bis [[3-(4-dimethylaminophenyl)-1-(2-norbornyl)ureido]methyl]cyclohexane The title compound was synthesized by the method in accordance with Example 2.

mp: 188°–191° C. (free form) MS(FAB): m/e=655 (M⁺+1) IR(KBr) ν MAX: 2942(brs), 1631(s), 1517(s) NMR (DMSO-d₆) δ: 7.87 (2H, t, J=9.0 Hz, NH×2), 7.20 (4H, d, J=9.2 Hz, Ar—H), 6.62 (4H, d, J=9.2 Hz, Ar—H)r 2.9–3.7 (6H, m, NCH₂×2, NCH×2), 2.80 (12H, s, N(CH₃)₂×2), 0.8–2.4 (30H, m) Elemental analysis (for C₄₀H₅₈N₆O₂.H₂O) Calculated (%): C, 71.39; H, 8.99; N, 12.49. Found (%): C, 71.37; H, 8.91; N, 12.04.

Example 46

Cis-1,4-bis[[1-(2-adamantyl)-3-(4-dimethylaminophenyl)ureido]methyl]cyclohexane

The title compound was synthesized by the method in accordance with Example 2.

mp: 251°–255° C. (dihydrochloric acid salt) MS(FAB): m/e=735 (M⁺+1) IR(KBr) ν MAX: 2910(brs), 1708(s), 1560(s), 1515(s) NMR(DMSO-d₆) δ: 8.59 (2H, brs, NH×2), 7.5–7.7 (8H, m, Ar—H), 3.24 (2H, brs, NCH×2), 3.06 (12H, s, N(CH₃)₂×2), 2.88 (4H, brs, NCH₂×2), 1.4–2.8 (38H, m) Elemental analysis (for C₄₆H₆₆N₆O₂·2HCl·3H₂O) Calculated (%): C, 64.09; H, 8.65; N, 9.75. Found (%): C, 63.75; H, 8.76; N, 9.78.

Example 47

Cis-1,4-bis[1-benzyl-3-(4-dimethylaminophenyl)ureido]methyl]cyclohexane

The title compound was synthesized by the method in accordance with Example 1.

mp: 155°–157° C. (dihydrochloric acid salt) MS(FAB): m/e=647 (M⁺+1) IR(KBr) ν MAX: 2923(brs), 1641(s), 1517(s) NMR(DMSO-d₆) δ: 8.60 (2H, s, NH×2), 7.2–7.7 (8H, br, Ar—H), 4.60 (4H, br, Ph—CH₂×2), 3.31 (4H, br, NCH₂×2), 3.05 (12H, brs, N(CH₃)₂×2), 1.83 (2H, br), 1.38 (8H, m) Elemental analysis (for C₄₀H₅₀N₆O₂·2.2HCl·2H₂O) Calculated (%): C, 63.57; H, 7.47; N, 11.12. Found (%): C, 63.35; H, 7.70; N, 10.91.

Example 48

Cis-1,4-bis[[3-(4-dimethylaminophenyl)-1-(2-phenetyl)ureido]methyl]cyclohexane

The title compound was synthesized by the method in accordance with Example 1.

mp: 153°–155° C. (free form) MS(FAB): m/e=675 (M⁺+1) IR(KBr) ν MAX: 2927(brs), 1610(s), 1521(s) NMR (DMSO-d₆) δ: 7.75 (2H, s, NH×2), 7.1–7.4 (14H, m, Ar—H), 6.62 (4H, d, J=8.8 Hz, Ar—H), 3.50 (4H, m, NCH₂×2), 3.1–3.2 (4H, m, NCH₂×2), 2.7–2.9 (16H, m, N(CH₃)₂×2, ArCH₂×2), 1.76 (2H, brs), 1.36 (8H, brs) Elemental analysis (for C₄₂H₅₄N₆O₂·2H₂O) Calculated (%): C, 72.80; H, 8.15; N, 12.13. Found (%): C, 72.45; H, 8.37; N, 12.12.

Example 49

Cis-1,4-bis[[1-[2-(1-cyclohexenyl)ethyl]-3-(4-dimethylaminophenyl)ureido]methyl]cyclohexane The title compound was synthesized by the method in accordance with Example 1.

mp: 152°–155° C. (free form) MS(FAB): m/e=683 (M⁺+1) IR(KBr) ν MAX: 2921(brs), 1612(s), 1519(s) NMR (DMSO-d₆) δ: 7.71 (2H, s, NH×2), 7.21 (4H, d, J=9.0 Hz, Ar—H), 6.62 (4H, d, J=9.0 Hz, Ar—H), 5.41 (2H, s, =CH×2), 3.35 (4H, t, J=7.3 Hz, NCH₂×2), 3.22 (4H, d, J=7.3 Hz, NCH₂×2), 2.11 (4H, t, J=7.3 Hz, CH₂×2), 1.3–2.6 (26H, m) Elemental analysis (for C₄₂H₆₂N₆O₂) Calculated (%): C, 73.86; H, 9.15; N, 12.31. Found (%): C, 73.76; H, 9.27; N, 12.32.

Example 50

Cis-1,4-bis[[3-[4-dimethylaminophenyl)-1-furfurylureido]methyl]cyclohexane

The title compound was synthesized by the method in accordance with Example 2.

mp: 129°–132° C. (free form) MS(FAB): m/e=627 (M⁺+1) IR(KBr) ν MAX: 2911(brs), 1635(s), 1612(s), 1519(s) NMR(DMSO-d₆) δ: 7.91 (2H, d, NH×2), 7.55 (4H, d, J=1.8 Hz, Ar—H), 7.22 (4H, d, J=9.0 Hz, Ar—H), 6.63 (4H, d, J=9.0 Hz, Ar—H), 6.38 (2H, mr Ar—H), 6.28 (2H, d, J=3.3 Hz, Ar—H), 4.52 (4H, s, NCH₂×2), 3.25 (4H, d, J=7.3 Hz, NCH₂×2), 2.81 (12H, s, N(CH₃)₂×2), 1.81 (2H, brs), 1.37 (8H, brs) Elemental analysis (for C₃₆H₄₆N₆O₂) Calculated (%): C, 68.99; H, 7.40; N, 13.41. Found (%): C, 68.71; H, 7.63; N, 13.72.

Example 51

Trans-1,3-bis[[3-[4-dimethylaminophenyl)-1-normalpentylureido]methyl]cyclohexane The title compound was synthesized by the method in accordance with Example 2.

mp: 124°–127° C. (free form) MS(FAB): m/e=607 (M⁺+1) IR(KBr) ν MAX: 2925(brs), 1631(s), 1587(s), 1519(s) NMR(DMSO-d₆) δ: 7.67 (2H, s, NH×2), 7.19 (4H, d, J=9.0 Hz, Ar—H), 6.59 (4H, d, J=9.0 Hz, Ar—H), 3.1–3.3 (8H, m, NCH₂×2), 2.79 (12H, s, N(CH₃)₂×2), 1.96 (2H, brs, CH₂× 2), 1.1–1.5(20H, m), 0.84 (6H, t, J=7.0 Hz, CH₂×2) Elemental analysis (for C₃₆H₅₈N₆O₂·H₂O) Calculated (%): C, 69.19; H, 9.68; N, 13.45. Found (%): C, 68.85; H, 10.05; N, 13.28.

Example 52

Trans-1,3-bis[[3-[4-dimethylaminophenyl)-1-normalhexylureido]methyl]cyclohexane

The title compound was synthesized by the method in accordance with Example 1.

mp: 144°–150° C. (dihydrochloric acid salt) MS(FAB): m/e=635 (M⁺+1) IR(KBr) ν MAX: 2921(brs), 1648(s), 1519(s) NMR(DMSO-d₆) δ: 8.38 (2H, s, NH×2), 7.5–7.65 (8H, m, Ar—H), 3.1–3.4 (8H, m, NCH₂×4), 3.05 (12H, s, N(CH₃)₂×2), 1.97 (2H, brs), 1.1–1.6 (24H, m), 0.84 (6H, t, J=7.0 Hz, CH₂×2) Elemental analysis (for C₃₈H₆₂N₆O₂·2HCl·H₂O) Calculated (%): C, 62.88; H, 9.16; N, 11.58. Found (%): C, 63.04; H, 9.26; N, 11.70.

Example 53

Trans-1,3-bis[[3-[4-dimethylaminophenyl)-1-normalheptylureido]methyl]cyclohexane The title compound was synthesized by the method in accordance with Example 1.

mp: 121°–126° C. (dihydrochloric acid salt) MS(FAB): m/e=663 (M⁺+1) IR(KBr) ν MAX: 2927(brs), 1643(s), 1517(s) NMR(DMSO-d₆) δ: 8.31 (2H, s, NH×2), 7.4–7.7 (8H, br, Ar—H), 3.0–3.4 (20H, m, NCH₂×4, N(CH₃)₂×2), 1.98 (2H, brs), 1.2–1.6 (28H, m), 0.84 (6H, t, J=7.0 Hz, CH₂×2) Elemental analysis (for C₄₀H₆₆N₆O₂·2HCl·2H₂O) Calculated (%): C, 60.82; H, 9.44; N, 10.64. Found (%): C, 60.63; H, 9.63; N, 10.61.

Example 54

Trans-1,3-bis[[3-[4-dimethylaminophenyl)-1-normaloctylureido]methyl]cyclohexane

The title compound was synthesized by the method in accordance with Example 1.

mp: 115°–119° (dihydrochloric acid salt) MS(FAB): m/e= 691 (M⁺+1) IR(KBr) ν MAX: 2923(brs), 1641(s), 1519(s) NMR(DMSO-d₆) δ: 8.34 (2H, brs, NH×2), 7.5–7.6 (8H, br, Ar—H), 3.1–3.4 (8H, m, NCH₂×4), 3.05 (12H, s, N(CH₃)₂), 1.96 (2H, m), 1.46 (6H, m), 1.2–1.4 (26H, m), 0.84 (6H,

Example 55

Trans-1,3-bis [[3- [4-dimethylaminophenyl)-1-normalnonylureido]methyl]cyclohexane The title compound was synthesized by the method in accordance with Example 1.

mp: 116°–120° C. (dihydrochloric acid salt) MS(FAB): m/e=719 (M$^+$+1) IR(KBr) ν MAX: 2908(brs), 1656(s), 1639(s), 1517(s) NMR(DMSO-d$_6$) δ: 8.38 (2H, s, NH×2), 7.5–7.7 (8H, m, Ar—H), 3.1–3.4 (8H, m, NCH$_2$×4), 3.07 (12H, s, N(CH$_3$)$_2$×2), 1.98 (2H, brs), 1.2–1–6 (36H, m), 0.85 (6H, t, J=7.0 Hz, CH$_2$×2) Elemental analysis (for C$_{44}$H$_{74}$N$_6$O$_2$.2HCl.1/2H$_2$O) Calculated (%): C, 65.98; H, 9.69; N, 10.49. Found (%): C, 65.70; H, 9.54; N, 9.92.

Example 56

Trans-1,3-bis[[3-(4-dimethylaminophenyl)-1-normaldecylureido]methyl]cyclohexane

The title compound was synthesized by the method in accordance with Example 2.

mp: 115°–117° C. (dihydrochloric acid salt) MS(FAB): m/e=747 (M$^+$+1) IR(KBr) ν MAX: 2921(brs), 1652(s), 1517(s) NMR(DMSO-d$_6$) δ: 8.35 (2H, s, NH×2), 7.5–7.7 (8H, m, Ar—H), 3.1–3.4 (8H, m, NCH$_2$×4), 3.05 (12H, s, N(CH$_3$)$_2$×2), 1.96 (2H, m), 1.2–1.6 (40H, m), 0.84 (6H, t, J=7.0 Hz, CH$_3$×2) Elemental analysis (for C$_{46}$H$_{78}$N$_6$O$_2$.2HCl.5/2H$_2$O) Calculated (%): C, 63.86; H, 9.90; N, 9.71. Found (%): C, 63.64; H, 9.67; N, 9.66.

Example 57

Trans-1,3-bis[[1-cyclohexylmethyl-3-(4-dimethylaminophenyl)ureido]methyl]cyclohexane The title compound was synthesized by the method in accordance with Example 2.

mp: 161°–164° C. (free form) MS(FAB): m/e=659 (M$^+$+1) IR(KBr) ν MAX: 2850(brs), 1629(s), 1590(s), 1519(s) NMR(DMSO-d$_6$) δ: 7.62 (2H, s, NH×2), 7.15 (4H, d, J=9.0 Hz, Ar—H), 6.55 (4H, d, J=9.0 Hz, Ar—H), 3.0–3.3 (8H, m, NCH$_2$×2), 2.74 (12H, s, N(CH$_3$)$_2$×2), 1.92 (2H, brs), 0.7–1.6 (30H, m) Elemental analysis (for C$_{40}$H$_{62}$N$_6$O$_2$.½H$_2$O) Calculated (%): C, 71.92; H, 9.51; N, 12.58. Found (%): C, 71.74; H, 10.04; N, 12.33.

Example 58

Trans-1,3-bis[[3-(4-dimethylaminophenyl)-1-(4-normalheptyl)ureido]methyl]cyclohexane The title compound was synthesized by the method in accordance with Example 2.

mp: 122°–126° C. (dihydrochloric acid salt) MS(FAB): m/e=663 (M$^+$+1) IR(KBr) ν MAX: 2917(brs), 1631(s), 1519(s) NMR(DMSO-d$_6$) δ: 8.26 (2H, s, NH×2), 7.5–7.7 (8H, m, Ar—H), 3.90 (2H, m, NCH×2), 2.9–3.2 (4H, m, NCH$_2$×4), 3.05 (12H, s, N(CH$_3$)$_2$×2), 1.86 (2H, brs, CH×2), 1.2–1.6 (24H, m), 0.8–0.9 (12H, m, CH$_2$×4) Elemental analysis (for C$_{40}$H$_{66}$N$_6$O$_2$.2HCl.3H$_2$O) Calculated (%): C, 60.82; H, 9.44; N, 10.64. Found (%): C, 60.95; H, 9.34; N, 10.39.

Example 59

Trans-1,3-bis[[1-cyclopentyl-3-(4-dimethylaminophenyl)ureido]methyl]cyclohexane

The title compound was synthesized by the method in accordance with Example 1.

mp: 142°–147° C. (free form) MS(FAB): m/e=603 (M$^+$+1) IR(KBr) ν MAX: 2938(brs), 1639(s), 1617(s), 1519(s) NMR(DMSO-d$_6$) δ: 7.69 (2H, s, NH×2), 7.19 (4H, d, J=9.2 Hz, Ar—H), 6.61 (4H, d, J=9.2 Hz, Ar—H), 4.06 (2H, m, NCH×2), 3.0–3.2 (4H, m, NCH$_2$×2), 2.81 (12H, s, N(CH$_3$)$_2$×2), 1.2–2.0 (26H, m) Elemental analysis (for C$_{36}$H$_{54}$N$_6$O$_2$) Calculated (%): C, 71.72; H, 9.03; N, 13.94. Found (%): C, 71.57; H, 9.55; N, 14.03.

Example 60

Trans-1,3-bis[[1-cyclohexyl-3-(4-dimethylaminophenyl)ureido]methyl]cyclohexane

The title compound was synthesized by the method in accordance with Example 1.

mp: 153°–159° C. (dihydrochloric acid salt) MS(FAB): m/e=631 (M$^+$+1) IR(KBr) ν MAX: 2927(brs), 1639(s), 1517(s) NMR(DMSO-d$_6$) δ: 8.38 (2H, s, NH×2), 7.56 (8H, s, Ar—H), 3.78 (2H, brs, NCH×2), 3.0–3.3 (16H, NCH$_2$×2), 3.06 (12H, s, N(CH$_3$)$_2$×2), 1.1–2.0 (28Hr m) Elemental analysis (for C$_{38}$H$_{58}$N$_6$O$_2$.2HCl.3H$_2$O) Calculated (%): Cr 60.22; H, 8.78; N, 11.09. Found (%): C, 59.83; H, 8.56; N, 11.29.

Example 61

Trans-1,3-bis[[1-cycloheptyl-3-(4-dimethylaminophenyl)ureido]methyl]cyclohexane

The title compound was synthesized by the method in accordance with Example 1.

mp: 109°–114° C. (dihydrochloric acid salt) MS(FAB): m/e=659 (M$^+$+1) IR(KBr) ν MAX: 2927(brs), 1643(s), 1592(s), 1516(s) NMR(DMSO-d$_6$) δ: 8.36 (2H, s, NH×2), 7.5–7.7 (8H, m, Ar—H), 3.74 (2H, m, NCH×2), 2.9–3.2 (4H, m, NCH$_2$×2), 3.06 (12H, s, N(CH$_3$)$_2$×2), 1.0–2.0 (34H, m) Elemental analysis (for C$_{40}$H$_{62}$N$_6$O$_2$.2HCl.2H$_2$O) Calculated (%): C, 62.56; H, 8.93; N, 10.94. Found (%): C, 62.30; H, 8.83; N, 10.93.

Example 62

Trans-1,3-bis[[3-(4-dimethylaminophenyl)-1-(2-norbornyl)ureido]methyl]cyclohexane The title compound was synthesized by the method in accordance with Example 2.

mp: 126°–129° C. (free form) MS(FAB): m/e 655 (M$^+$+1) IR(KBr) ν MAX: 2933(brs), 1629(s), 1594(s), 1519(s) NMR (DMSO-d$_6$) δ: 7.68 (2H, s, NH×2), 7.19 (4H, m, Ar—H), 6.62 (4H, m, Ar—H), 3.67 (2H, m, NCH×2), 2.9–3.5 (4H, m, NCH$_2$×2), 2.80 (12H, s, N(CH$_3$)$_2$×2), 1.0–2.4 (30H, m) Elemental analysis (for C$_{40}$H$_{58}$N$_6$O$_2$.H$_2$O) Calculated (%): C, 71.39; H, 8.99; N, 12.49. Found (%): C, 71.41; H, 9.38; N, 12.48.

Example 63

Trans-1,3-bis[[3-(4-dimethylaminophenyl)-1-(4-methylcyclohexyl)ureido]methyl]cyclohexane The title compound was synthesized by the method in accordance with Example 2.

mp: 106°–110° (free form) MS(FAB): m/e=659 (M$^+$+1) IR(KBr) ν MAX: 2918(brs), 1629(s), 1592(s), 1517(s) NMR (DMSO-d$_6$) δ: 7.69 (2H, s, NH×2), 7.19 (4H, d, J=9.0 Hz, Ar—H), 6.61 (4H, d, J=9.0 Hz, Ar—H), 3.6–3.8 (2H, m, NCH×2), 3.0–3.2 (4H, m, NCH$_2$×4), 2.81 (12H, s, N(CH$_3$)

$_2\times2$), 0.8–2.0 (22H, m) Elemental analysis (for $C_{40}H_{62}N_6O_2 \cdot 5/2H_2O$) Calculated (%): C, 68.24; H, 9.59; N, 11.94. Found (%): C, 68.01; H, 9.60; N, 11.49.

Example 64

Trans-1,3-bis[[3-(4-dimethylaminophenyl)-1-benzylureido]methyl]cyclohexane

The title compound was synthesized by the method in accordance with Example 1.

mp: 158°–163° (free form) MS(FAB): m/e=646 ($M^+$) IR(KBr) ν MAX: 3461(brs), 1633(s), 1458(s) NMR (DMSO-$d_6$) δ: 8.66 (2H, s, NH×2), 7.5–7.7 (8H, brs, Ar—H), 7.1–7.35 (10H, m, Ar—H), 4.61 (4H, brs, NCH$_2$Ph×2), 3.18 (4H, NCH$_2$×2), 3.04 (12H, N(CH$_3$)$_2$×2), 2.03 (2H, brs), 1.1–1.6 (8H, m) Elemental analysis (for $C_{40}H_{50}N_6O_2 \cdot 2HCl \cdot 2H_2O$) Calculated (%): C, 63.48; H, 7.51; N, 10.97. Found (%): C, 63.57; H, 7.47; N, 11.12.

Example 65

Trans-1,3-bis[[3-(4-dimethylaminophenyl)-1-(2-phenetyl)ureido]methyl]cyclohexane The title compound was synthesized by the method in accordance with Example 1.

mp: 130°–135° C. (free form) MS(FAB): m/e=675 ($M^++1$) IR(KBr) ν MAX: 2925(brs), 1633(s), 1592(s), 1523(s) NMR(DMSO-$d_6$) δ: 7.33 (2H, s, NH×2), 7.1–7.3 (14H, m, Ar—H), 6.61 (4H, d, J=8.8 Hz, Ar—H), 3.48 (4H, m, NCH$_2$×2), 3.13 (4H, m, J=7.7 Hz, NCH$_2$×2), 2.7–2.9 (16H, m, N(CH$_3$)$_2$×2, PhCH$_2$×2), 1.95 (2H, brs), 1.1–1.5 (8H, m) Elemental analysis (for $C_{42}H_{54}N_6O_2$) Calculated (%): C, 74.74; H, 8.06; N, 12.45. Found (%): C, 74.60; H, 8.36; N, 12.37.

Example 66

Trans-1,3-bis[[1-[2-(1-cyclohexenyl)ethyl]-3-(4-dimethylaminophenyl)ureido]methyl]cyclohexane The title compound was synthesized by the method in accordance with Example 1.

mp: 129°–131° C. (free form) MS(FAB): m/e=683 ($M^++1$) IR(KBr) ν MAX: 2927(brs), 1641(s), 1594(s), 1529(s) NMR(DMSO-$d_6$) δ: 7.72 (2H, s, NH×2), 7.23 (4H, d, J=8.8 Hz, Ar—H), 6.64 (4H, d, J=8.8 Hz, Ar—H), 5.42 (2H, s, =CH×2), 3.37 (4H, m, NCH$_2$×2), 3.1–3.2 (4H, m, NCH$_2$×2), 2.83 (12H, s, N(CH$_3$)$_2$×2), 2.11 (4H, m, =C—CH$_2$×2), 1.95 (10H, m), 1.2–1.7 (16H, m) Elemental analysis (for $C_{42}H_{62}N_6O_2$) Calculated (%): C, 73.86; H, 9.15; N, 12.31. Found (%): C, 73.77; H, 9.48; N, 12.10.

Example 67

Cis-1,3-bis[[3-(4-dimethylaminophenyl)-1-normalpentylureido]methyl]cyclohexane

The title compound was synthesized by the method in accordance with Example 1.

mp: 172°–176° C. (dihydrochloric acid salt) MS(FAB): m/e=607 ($M^++1$) IR(KBr) ν MAX: 2929(brs), 1650(s), 1519(s) NMR(DMSO-$d_6$) δ: 8.26 (2H, brs, NH×2), 7.4–7.6 (8H, m, Ar—H), 3.28 (4H, d, J=7.0 Hz, NCH$_2$×2), 3.17 (4H, NCH$_2$×2), 3.05 (12H, s, N(CH$_3$)$_2$×2), 1.1–1.8 (20H, m), 0.6–1.0 (8H, m) Elemental analysis (for $C_{36}H_{58}N_6O_2 \cdot 2HCl$) Calculated (%): C, 62.77; H, 8.93; N, 12.20. Found (%): C, 62.66; H, 9.42; N, 12.46.

Example 68

Cis-1,3-bis[[3-(4-dimethylaminophenyl)-1-normalhexylureido]methyl]cyclohexane

The title compound was synthesized by the method in accordance with Example 1.

mp: 121°–125° C. (dihydrochloric acid salt) MS(FAB): m/e=635 ($M^++1$) IR(KBr) ν MAX: 2929(brs), 1650(s), 1521(s) NMR(DMSO-$d_6$) δ: 8.32 (2H, s, NH×2), 7.5–7.7 (8H, m, Ar—H), 3.10–3.35 (8H, m, NCH$_2$×4), 3.06 (12H, s, N(CH$_3$)$_2$×2), 0.6–1.8 (32H, m) Elemental analysis (for $C_{38}H_{62}N_6O_2 \cdot 2HCl$) Calculated (%): C, 63.67; H, 9.14; N, 11.73. Found (%): C, 63.78; H, 9.06; N, 11.77.

Example 69

Cis-1,3-bis[[3-(4-dimethylaminophenyl)-1-normalheptylureido]methyl]cyclohexane

The title compound was synthesized by the method in accordance with Example 1.

mp: 124°–127° C. (dihydrochloric acid salt) MS(FAB): m/e=663 ($M^++1$) IR(KBr) ν MAX: 2929(brs), 1650(s), 1521(s) NMR(DMSO-$d_6$) δ: 8.35 (2H, s, NH×2), 7.5–7.7 (8H, m, Ar—H), 3.10–3.35 (8H, m, NCH$_2$×4), 3.07 (12H, m, N(CH$_3$)$_2$×2), 0.6–1.8 (36H, m) Elemental analysis (for $C_{40}H_{66}N_6O_2 \cdot 2HCl \cdot H_2O$) Calculated (%): C, 63.72; H, 9.36; N, 11.15. Found (%): C, 63.43; H, 9.05; N, 11.44.

Example 70

Cis-1,3-bis[[3-(4-dimethylaminophenyl)-1-normaloctylureido]methyl]cyclohexane

The title compound was synthesized by the method in accordance with Example 1.

mp: 118°–121° C. (dihydrochloric acid salt) MS(FAB): m/e=690 ($M^+$) IR(KBr) ν MAX: 2927(brs), 1643(s), 1519(s) NMR(DMSO-$d_6$) δ: 8.32 (2H, brs, NH×2), 7.5–7.6 (8H, br, Ar—H), 3.28 (4H, m, NCH$_2$×2), 3.17 (4H, m, NCH$_2$×2), 3.05 (12H, s, N(CH$_3$)$_2$×2), 1.4–1.8 (8H, m), 1.24 (24H, brs, CH$_2$×2), 0.6–0.9 (8H, m) Elemental analysis (for $C_{42}H_{70}N_6O_2 \cdot 2HCl \cdot 3/2H_2O$) Calculated (%): C, 63.78; H, 9.86; N, 10.63. Found (%): C, 63.68; H, 9.79; N, 10.83.

Example 71

Cis-1,3-bis[[3-(4-dimethylaminophenyl)-1-normalnonylureido]methyl]cyclohexane

The title compound was synthesized by the method in accordance with Example 1.

mp: 132°–133° C. (dihydrochloric acid salt) MS(FAB): m/e=719 ($M^++1$) IR(KBr) ν MAX: 2925(brs), 1646(s), 1521(s) NMR(DMSO-$d_6$) δ: 8.34 (2H, s, NH×2), 7.5–7.65 (8H, br, Ar—H), 3.15–3.35 (8H, m, NCH$_2$×4), 3.06 (12H, s, N(CH$_3$)$_2$×2), 0.55–1.8 (44H, m) Elemental analysis (for $C_{44}H_{74}N_6O_2 \cdot 2HCl$) Calculated (%): C, 65.98; H, 9.69; N, 10.49. Found (%): C, 65.77; H, 10.19; N, 10.35.

Example 72

Cis-1,3-bis[[3-(4-dimethylaminophenyl)-1-normaldecylureido]methyl]cyclohexane

The title compound was synthesized by the method in accordance with Example 1.

mp: 165°–170° C. (dihydrochloric acid salt) MS(FAB): m/e=747 ($M^++1$) IR(KBr) ν MAX: 2921(brs), 1650(s), 1519(s) NMR(DMSO-d$_6$) δ: 8.28 (2H, brs, NH×2), 7.4–7.6 (8H, br, Ar—H), 3.28 (4H, br, NCH$_2$×2), 3.17 (4H, m, NCH$_2$×2), 3.05 (12H, s, N(CH$_3$)$_2$×2), 1.1–1.8 (40H, m), 0.6–0.9 (8H, m) Elemental analysis (for C$_{46}$H$_{78}$N$_6$O$_2$.2HCl) Calculated (%): C, 66.64; H, 9.85; N, 10.14. Found (%): C, 66.60; H, 10.14; N, 10.34.

Example 73

Cis-1,3-bis[[3-(4-dimethylaminophenyl)-1-neopentylureido]methyl]cyclohexane

The title compound was synthesized by the method in accordance with Example 1.

mp: 171°–173° C. (dihydrochloric acid salt) MS(FAB): m/e=607 (M$^+$+1) IR(KBr) ν MAX: 2931(brs), 1644(s), 1542(s) NMR(DMSO-d$_6$) δ: 8.50 (2H, s, NH×2), 7.58 (8H, s, Ar—H), 3.10–3.35 (8H, m, NCH$_2$×4), 3.06 (12H, s, N(CH$_3$)$_2$×2), 1.68–1.75 (6H, m), 0.55–1.2 (20H, m) Elemental analysis (for C$_{36}$H$_{58}$N$_6$O$_2$.2HCl.H$_2$O) Calculated (%): C, 61.96; H, 8.96; N, 12.04. Found (%): C, 61.69; H, 8.74; N, 12.22.

Example 74

Cis-1,3-bis[[1-cyclohexylmethyl-3-(4-dimethylaminophenyl)ureido]methyl]cyclohexane The title compound was synthesized by the method in accordance with Example 1.

mp: 136°–140° C. (dihydrochloric acid salt) MS(FAB): m/e=659 (M$^+$+1) IR(KBr) ν MAX: 2921(brs), 1635(s), 1527(s) NMR(DMSO-d$_6$) δ: 8.41 (2H, s, NH×2), 7.55–7.65 (8H, brs, Ar—H), 3.1–3.3 (8H, br, NCH$_2$×4), 3.07 (12H, s, N(CH$_3$)$_2$×2), 0.6–1.8 (32H, m) Elemental analysis (for C$_{40}$H$_{62}$N$_6$O$_2$.2HCl.22H$_2$O) Calculated (%): C, 62.56; H, 8.93; N, 10.94. Found (%): C, 62.43; H, 8.83; N, 10.88.

Example 75

Cis-1,3-bis[[1-isopropyl-3-(4-dimethylaminophenyl)ureido]methyl]cyclohexane

The title compound was synthesized by the method in accordance with Example 1.

mp: 139°–141° C. (dihydrochloric acid salt) MS(FAB): m/e=551 (M$^+$+1) IR(KBr) ν MAX: 2919(brs), 1644(s), 1523(s) NMR(DMSO-d$_6$) δ:8.35 (2H, s, NH×2), 7.56 (8H, br, Ar—H), 4.18 (2H, m, NCH×2), 3.0–3.15 (16H, m, NCH$_2$×2, N(CH$_3$)$_2$×2), 1.55–1.8 (6H, m), 0.6–1.2 (22H, m) Elemental analysis (for C$_{32}$H$_{50}$N$_6$O$_2$.2HCl.H$_2$O) Calculated (%): C, 59.89; H, 8.48; N, 13.10. Found (%): C, 59.50; H, 8.44; N, 13.30.

Example 76

Cis-1,3-bis[[3-(4-dimethylaminophenyl)-1-(3-pentyl)ureido]methyl]cyclohexane The title compound was synthesized by the method in accordance with Example 2.

mp: 157°–160° C. (free form) MS(FAB): m/e=607 (M$^+$+1) IR(KBr) ν MAX: 2927(brs), 1629(s), 1592(s), 1521(s) NMR(DMSO-d$_6$) δ: 7.62 (2H, s, NH×2), 7.19 (4H, d, J=9.2 Hz, Ar—H), 6.61 (4H, d, J=9.2 Hz, Ar—H), 3.67 (2H, m, NCH×2), 2.97 (4H, m, NCH$_2$×2), 2.81 (12H, s, N(CH$_3$)$_2$×2), 1.4–1.9 (18H, m), 0.83 (12H, m, CH$_2$×4) Elemental analysis (for C$_{36}$H$_{58}$N$_6$O$_2$) Calculated (%): C, 71.25; H, 9.63; N, 13.85. Found (%): C, 71.76; H, 9.97; N, 13.73.

Example 77

Cis-1,3-bis[[3-(4-dimethylaminophenyl)-1-(4-heptyl)ureido]methyl]cyclohexane The title compound was synthesized by the method in accordance with Example 2.

mp: 130°–140° C. (dihydrochloric acid salt) MS(FAB): m/e=663 (M$^+$+1) IR(KBr) ν MAX: 2960(brs), 1633(s), 1519(s) NMR(DMSO-d$_6$) δ: 8.25 (2H, s, NH×2), 7.54 (8H, m, Ar—H), 3.93 (2H, m, NCH×2), 2.9–3.1 (4H, m, NCH$_2$×2), 3.06 (12H, s, N(CH$_3$)$_2$×2), 0.6–1.8 (38H, m) Elemental analysis (for C$_{40}$H$_{66}$N$_6$O$_2$.2HCl.3H$_2$O) Calculated (%): C, 60.82; H, 9.44; N, 10.64. Found (%): C, 60.55; H, 9.70; N, 10.87.

Example 78

Cis-1,3-bis[[1-cyclopentyl-3-(4-dimethylaminophenyl)ureidomethyl]cyclohexane The title compound was synthesized by the method in accordance with Example 1.

mp: 138°–140° C. (dihydrochloric acid salt) MS(FAB): m/e=602 (M$^+$) IR(KBr) ν MAX: 2919(brs), 1648(s), 1519(s) NMR(DMSO-d$_6$) δ: 8.37 (2H, s, NH×2), 7.5–7.7 (8H, m, Ar—H), 4.16 (2H, m, NCH×2), 3.05–3.2 (16H, m, NCH$_2$×2, N(CH$_3$)$_2$×2), 1.4–1.8 (22H, m), 0.6–1.2 (4H, m) Elemental analysis (for C$_{36}$H$_{54}$N$_6$O$_2$.2HCl.3/2H$_2$O) Calculated (%): C, 61.52; H, 8.46; N, 11.96. Found (%): C, 61.70; H, 8.28; N, 12.48.

Example 79

Cis-1,3-bis[[1-cyclohexyl-3-(4-dimethylaminophenyl)ureido]methyl]cyclohexane The title compound was synthesized by the method in accordance with Example 1.

mp: 145°–146° (dihydrochloric acid salt) MS(FAB): m/e= 631 (M$^+$+1) IR(KBr) ν MAX: 2927(brs), 1648(s), 1523(s) NMR(DMSO-d$_6$) δ: 8.35 (2H, s, NH×2), 7.5–7–6 (8Hr brs, Ar—H), 3.79 (2H, br, NCH×2), 3.0–3.15 (16H, m), 0.55–1.8 (30H, m) Elemental analysis (for C$_{38}$H$_{58}$N$_6$O$_2$.2HCl.3/2H$_2$O) Calculated (%): C, 62.45; H, 8.69; N, 11.50. Found (%): C, 62.05; H, 8.67; N, 11.61.

Example 80

Cis-1,3-bis[[1-cyclohexyl-3-(4-piperidinophenyl)ureido]methyl]cyclohexane

The title compound was synthesized by the method in accordance with Example 1.

mp: 174°–178° C. (dihydrochloric acid salt) MS(FAB): m/e=711 (M$^+$+1) IR(KBr) ν MAX: 2935(brs), 1652(s), 1515(s) NMR(DMSO-d$_6$) δ: 8.36 (2H, s, NH×2), 7.5–7.8 (8H, m, Ar—H), 3.79 (2H, br, NCH×2), 3.2–3.5 (8H, m, N(CH$_2$)$_2$×2), 3.08 (4H, NCH$_2$×2), 0.5–1.8 (42H, m) Elemental analysis (for C$_{44}$H$_{66}$N$_6$O$_2$.2HCl) Calculated (%): C, 67.41; H, 8.74; N, 10.72. Found (%): C, 67.20; H, 9.12; N, 10.60.

Example 81

Cis-1,3-bis[[1-cyclohexyl-3-(4-diethylaminophenyl)ureido]methyl]cyclohexane

The title compound was synthesized by the method in accordance with Example 1.

mp: 170°–172° C. (dihydrochloric acid salt) MS(FAB): m/e=687 (M⁺+1) IR(KBr) ν MAX: 2940(brs), 1646(s), 1515(s) NMR(DMSO-$d_6$) δ: 8.39 (2H, s, NH×2), 7.5–7.8 (8H, m, Ar—H), 3.79 (2H, m, NCH×2), 3.4–3.6 (8H, m, N(CH$_2$)$_2$×2), 3.08 (4H, NCH$_2$×2), 0.5–1.8 (42H, m) Elemental analysis (for $C_{42}H_{66}N_6O_2 \cdot 2HCl \cdot 3H_2O$) Calculated (%): C, 61.97; H, 9.16; N, 10.33. Found (%): C, 61.60; H, 8.89; N, 10.44.

Example 82

Cis-1,3-bis[[1-cyclohexyl-3-(1-methylindoli-5-ne)ureido]methyl]cyclohexane

The title compound was synthesized by the method in accordance with Example 1.

mp: 154°–156° C. (dihydrochloric acid salt) MS(FAB): m/e=654 (M⁺+1) IR(KBr) ν MAX: 2921(s), 1644(s), 1496 (s) NMR(DMSO-$d_6$) δ: 8.22 (2H, s, NH×2), 7.1–7.6 (6H, m, Ar—H), 3.6–3.9 (6H, m, NCH×2, NCH$_2$CH$_2$×2), 2.9–3.2 (14H, m, NCH$_2$×2, NCH$_2$CH$_2$×2, NCH$_2$×2), 0.5–1.8 (30H, m) Elemental analysis (for $C_{40}H_{58}N_6O_2 \cdot 2HCl \cdot 5/2H_2O$) Calculated (%): C, 62.16; H, 8.48; N, 10.87. Found (%): C, 62.26; H, 8.25; N, 10.98.

Example 83

Cis-1,3-bis[[1-cycloheptyl-3-(4-dimethylaminophenyl)ureido]methyl]cyclohexane

The title compound was synthesized by the method in accordance with Example 1.

mp: 166°–168° C. (dihydrochloric acid salt) MS(FAB): m/e=659 (M⁺+1) IR(KBr) ν MAX: 2927(s), 1646(s), 1593 (s), 1524(s) NMR(DMSO-$d_6$) δ: 8.36 (2H, s, NH×2), 7.5–7.7 (8H, m, Ar—H), 3.76 (2H, m, NCH×2), 3.0–3.2 (4H, m, NCH$_2$×2), 3.06 (12H, s, N(CH$_3$)$_2$×2), 0.5–1.8 (34H, m, CH$_2$×17) Elemental analysis (for $C_{40}H_{62}N_6O_2 \cdot 2HCl \cdot 3/2H_2O$) Calculated (%): C, 63.31; H, 8.63; N, 11.07. Found (%): C, 62.25; H, 8.75; N, 11.10.

Example 84

Cis-1,3-bis[[1-cyclooctyl-3-(4-dimethylaminophenyl)ureido]methyl]cyclohexane

The title compound was synthesized by the method in accordance with Example 1.

mp: 147°–149° (dihydrochloric acid salt) MS(FAB): m/e=687 (M⁺+1) IR(KBr) ν MAX: 2921(s), 1643(s), 1521(s) NMR(DMSO-$d_6$) δ: 8.23 (2H, s, NH×2), 7.54 (8H, s, Ar—H), 3.78 (2H, m, NCH×2), 3.0–3.2 (16H, NCH$_2$×2, N)CH$_3$)$_2$2), 0.6–1.9 (38H, m) Elemental analysis (for $C_{42}H_{66}N_6O_2 \cdot 2HCl$) Calculated (%): C, 65.60; H, 9.04; N, 10.93. Found (%): C, 65.49; H, 9.10; N, 11.36.

Example 85

Cis-1,3-bis[[3-(4-dimethylaminophenyl)-1-(2-norbornyl)ureido]methyl]cyclohexane

The title compound was synthesized by the method in accordance with Example mp: 110°–115° C. (free form) MS(FAB): m/e=655 (M⁺+1) IR(KBr) ν MAX: 2950(s), 1635(s), 1627(s), 1519(s) NMR(DMSO-$d_6$) δ: 7.67 (2H, brs, NH×2), 7.20 (4H, m, Ar—H), 6.62 (4H, mr Ar—H), 3.72 (2H, m, NCH×2), 2.9–3.3 (4H, m, NCH$_2$×2), 2.81 (12H, s, N(CH$_3$)$_2$×2), 2.27 (2H, brs), 2.19 (2H, brs), 0.7–1.9 (26H, m) Elemental analysis (for $C_{40}H_{58}N_6O_2 \cdot 2H_2O$) Calculated (%): C, 69.53; H, 9.04; N, 12.16. Found (%): C, 69.72; H, 9.20; N, 11.72.

Example 86

Cis-1,3-bis[[3-(4-dimethylaminophenyl)-1-benzylureido]methyl]cyclohexane

The title compound was synthesized by the method in accordance with Example 1.

mp: 129°–133° C. (dihydrochloric acid salt) MS(FAB): m/e=646 (M⁺) IR(KBr) ν MAX: 2925(brs), 1648(s), 1521(s) NMR(DMSO-$d_6$) δ: 8.55 (2H, s, NH×2), 7.50–7.65 (6H, m, Ar—H), 7.15–7.35 (8H, mr Ar—H), 4.53–4.65 (4H, m, PhCH$_2$×2), 3.18 (4H, t, J=7.3 Hz, NCH$_2$×2), 3.06 (12Hr s, N(CH$_3$)$_2$×2), 1.5–1.8 (6H, m), 0.6–1.2 (4H, m) Elemental analysis (for $C_{40}H_{50}N_6O_2 \cdot 2HCl \cdot 1/2H_2O$) Calculated (%): C, 65.92; H, 7.33; N, 11.53. Found (%): C, 65.92; H, 7.66; N, 11.20.

Example 87

Cis-1,3-bis[[3-(4-dimethylaminophenyl)-1-(2-phenetyl)ureido]methyl]cyclohexane

The title compound was synthesized by the method in accordance with Example 1.

mp: 167°–171° C. (dihydrochloric acid salt) MS(FAB): m/e=675 (M⁺+1) IR(KBr) ν MAX: 2925(s), 1648(s), 1521 (s) NMR(DMSO-$d_6$) δ: 8.34 (2H, s, NH×2), 7.5–7.6 (8H, brs, Ar—H), 7.1–7.3 (10H, m, Ar—H), 3.54 (4H, m, N-CH$_2$CH$_2$Ph×2), 3.13 (4H, m, NCH$_2$×2), 3.06 (12H, s, N(CH$_3$)$_2$×2), 2.79 (4H, t, J=7.5 Hz, PhCH$_2$×2), 1.5–1.8 (6H, m), 0.55–1.2 (4H, m) Elemental analysis (for $C_{42}H_{54}N_6O_2 \cdot 2HCl$) Calculated (%): C, 66.65; H, 7.59; N, 11.10. Found (%): C, 66.44; H, 8.06; N, 11.49.

Example 88

Cis-1,3-bis[[1-[2-(1-cyclohexenyl)ethyl]-3-(4-dimethylaminophenyl)ureido]methyl]cyclohexane The title compound was synthesized by the method in accordance with Example 1.

mp: 80°–83° C. (free form) MS(FAB): m/e=683 (M⁺+1) IR(KBr) ν MAX: 2921(brs), 1633(s), 1590(s), 1517(s) NMR (DMSO-$d_6$) δ: 7.73 (2H, s, NH×2), 7.24 (4H, d, J=8.8 Hz, Ar—H ), 6.66 (4H, d, J=8.8 Hz, Ar—H ), 5.44 (2H, s, =CH×2), 3.38 (4H, m, NCH$_2$×2), 3.17 (4H, m, NCH$_2$×2), 2.85 (12H, s, N(CH$_3$)$_2$×2), 2.13 (4H, m, =C—CH$_2$×2), 0.6–2.1 (26H, m) Elemental analysis (for $C_{42}H_{62}N_6O_2$) Calculated (%): C, 73.86; H, 9.15; N, 12.31. Found (%): C, 73.61; H, 9.17; N, 12.18.

Example 89

Cis-1,3-bis[[3-(4-dimethylaminophenyl)-1-furfurylureido]methyl]cyclohexane

The title compound was synthesized by the method in accordance with Example 2.

mp: 68°–73° C. (free form) MS(FAB): m/e=627 (M⁺+1) IR(KBr) ν MAX: 2927(brs), 1639(s), 1519(s) NMR (DMSO-$d_6$) δ: 7.91 (2H, s, NH×2), 7.55 (2H, m, Ar—H), 7.22 (4H, d, J=9.2 Hz, Ar—H), 6.64 (4H, d, J=9.2 Hz, Ar—H), 6.38 (2H, m, Ar—H), 6.28 (2H, m, Ar—H), 4.52 (4H, s, Ar—CH$_2$×2), 3.15 (4H, d, J=5.5 Hz, NCH$_2$×2), 2.82 (12H, s, N(CH$_3$)$_2$×2), 0.6–1.8 (10H, m) Elemental analysis (for $C_{36}H_{46}N_6O_4 \cdot H_2O$) Calculated (%): C, 67.06; H, 7.50; N, 13.03. Found (%): C, 66.91; H, 7.21; N, 12.82.

Example 90

Cis-1,2-bis[[3-(4-dimethylaminophenyl)-1-normalheptylureido]methyl]cyclohexane

The title compound was synthesized by the method in accordance with Example 1.

mp: 135°–138° C. (free form) MS(FAB): m/e=663 (M$^+$+1) IR(KBr) ν MAX: 2923(brs), 1631(s), 1596(s), 1519(s) NMR(DMSO-d$_6$) δ: 7.74 (2H, s, NH×2), 7.19 (4H, d, J=9.0 Hz, Ar—H ), 6.60 (4H, d, J=9.0 Hz, Ar—H ), 3.2–3.4 (8H, m, NH$_2$×4), 2.81 (12H, s, N(CH$_3$)$_2$×2), 1.90 (2H, brs, CH×2), 1.2–1.7 (28H, m), 0.85 (6H, t, J=7.0 Hz, CH$_2$×2) Elemental analysis (for C$_{40}$H$_{66}$N$_6$O$_2$.H$_2$O) Calculated (%): C, 70.55; H, 10.06; N, 12.34. Found (%): C, 70.38; H, 10.26; N, 12.00.

Example 91

Trans-1,2-bis[[1-cyclohexyl-3-(4-dimethylaminophenyl)ureido]methyl]cyclohexane

The title compound was synthesized by the method in accordance with Example 1.

mp: 108°–114° C. (free form) MS(FAB): m/e =631 (M$^+$+1) IR(KBr) ν MAX: 2933(brs), 1629(s), 1616(s), 1519(s) NMR (DMSO-d$_6$) δ: 7.77 (2H, s, NH×2), 7.18 (4H, d, J=8.8 Hz, Ar—H), 6.62 (4H, d, J=8.8 Hz, Ar—H), 3.74 (2H, m, NCH×2), 3.45 (2H, m, CH$_2$×2), 3.1–3.2 (2H, m, CH$_2$×2), 2.81 (12H, s, N(CH$_3$)$_2$×2), 1.0–1.8 (30H, m) Elemental analysis (for C$_{38}$H$_{58}$N$_6$O$_2$) Calculated (%): C, 72.34; H, 9.27; N, 13.32. Found (%): C, 72.08; H, 9.50; N, 13.10.

Example 92

Trans-1,2-bis[[1-cycloheptyl-3-(4-dimethylaminophenyl)ureido]methyl]cyclohexane

The title compound was synthesized by the method in accordance with Example 1.

mp: 125°–129° C. (dihydrochloric acid salt) MS(FAB): m/e=659 (M$^+$+1) IR(KBr) ν MAX: 2920(s), 1646(s), 1629 (s), 1556(s), 1517(s) NMR(DMSO-d$_6$) δ: 8.39 (2H, s, NH×2), 7.4–7.7 (8H, m, Ar—H), 3.1–3.8 (6H, m, NCH×2, NCH$_2$×2), 3.06 (12H, s, N(CH$_3$)$_2$×2), 1.0–1.9 (34H, m) Elemental analysis (for C$_{40}$H$_{62}$N$_6$O$_2$.2HCl3H$_2$O) Calculated (%): C, 61.13; H, 8.98; N, 10.69. Found (%): C, 61.24; H, 8.80; N, 10.41.

Example 93

Trans-1,2-bis[[3-(4-dimethylaminophenyl)-1-benzylureido]methyl]cyclohexane

The title compound was synthesized by the method in accordance with Example 2.

mp: 109°–113° C. (free form) MS(FAB): m/e=647 (M$^+$+1) IR(KBr) ν MAX: 2927(s), 1629(s), 1592(s), 1519(s) NMR(DMSO-d$_6$) δ: 7.96 (2H, s, NH×2), 7.1–7.4 (14H, m, Ar—H), 6.60 (4H, d, J=9.1 Hz, Ar—H), 4.54 (4H, s, NCH$_2$×2), 3.1–3.5 (4H, m, NCH$_2$×2), 2.81 (12H, s, N(CH$_3$)$_2$×2), 1.5–1.8 (6H, m), 1.0–1.2 (4H, m) Elemental analysis (for C$_{40}$H$_{50}$N$_6$O$_2$) Calculated (%): C, 74.27; H, 7.79; N, 12.99. Found (%): C, 74.10; H, 8.05; N, 12.70.

Example 94

Trans-1,2-bis[[3-(4-dimethylaminophenyl)-1-normalhexylureido]methyl]cyclohexane

The title compound was synthesized by the method in accordance with Example 2.

mp: 112°–117° C. (dihydrochloric acid salt) MS(FAB): m/e=663 (M$^+$+1) IR(KBr) ν MAX: 2910(brs), 1652(s), 1517(s) NMR(DMSO-d$_6$) δ: 8.40 (2H, s, NH×2), 7.5–7.7 (8H, m, Ar—H), 3.0–3.6 (2OH, NCH$_2$×4, N(CH$_3$)$_2$×2), 0.8–1.7 (36H, m) Elemental analysis (for C$_{40}$H$_{66}$N$_6$O$_2$.2HCl.3H$_2$O) Calculated (%): C, 60.82; H, 9.44; N, 10.64. Found (%): C, 60.60; H, 9.93; N, 10.49.

Example 95

Cis-1,2-bis[[1-cyclohexylmethyl-3-(4-dimethylaminophenyl)ureido]methyl]cyclohexane The title compound was synthesized by the method in accordance with Example 1.

mp: 102°–106° C. (free form) MS(FAS): m/e=659 (M$^+$+1) IR(KBr) ν MAX: 2927(brs), 1631(s), 1590(s), 1521(s) NMR(DMSO-d$_6$) δ: 7.75 (2H, s, NH×2), 7.20 (4H, d, J=8.8 Hz, Ar—H), 6.61 (4H, J=8.8 Hz, Ar—H), 3.32 (4H, m, NCH$_2$×2), 3.13 (4H, m, NCH$_2$×2), 2.80 (12H, s, N(CH$_3$)$_2$× 2), 0.8–2.2 (32H, m) Elemental analysis (for C$_{40}$H$_{62}$N$_6$O$_2$) Calculated (%): C, 72.91; H, 9.48; N, 12.75. Found (%): C, 72.87; H, 9.83; N, 12.53.

Example 96

Cis-1,2-bis[[1-cyclohexyl-3-(4-dimethylaminophenyl)ureido]methyl]cyclohexane

The title compound was synthesized by the method in accordance with Example 1.

mp: 149°–154° C. (dihydrochloric acid salt) MS(FAB): m/e=631 (M$^+$+1) IR(KBr) ν MAX: 2933(brs), 1646(s), 1556(s), 1540(s) NMR(DMSO-d$_6$) δ: 8.47 (2H, s, NH×2), 7.4–7.7 (8H, m, Ar—H), 3.73 (2H, m, NCH×2), 3.2–3.5 (4H, m, NCH$_2$×2), 3.06 (12H, s, N(CH$_3$)$_2$×2), 1.0–1.9 (30H, m) Elemental analysis (for C$_{38}$H$_{58}$N$_6$O$_2$.2HCl.22H$_2$O) Calculated (%): C, 61.69; H, 8.72; N, 11.36. Found (%): C, 61.79; H, 8.90; N, 11.10.

Example 97

Cis-1,2-bis[[1-cycloheptyl-3-(4-dimethylaminophenyl)ureido]methyl]cyclohexane

The title compound was synthesized by the method in accordance with Example 1.

mp: 107°–112° C. (dihydrochloric acid salt) MS(FAB): m/e=659 (M$^+$+1) IR(KBr) ν MAX: 2921(brs), 1646(s), 1590(s), 1519(s) NMR(DMSO-d$_6$) δ: 8.45 (2H, s, NH×2), 7.5–7.7 (8H, m, Ar—H), 3.2–3.8 (6H, m, NCH×2, NCH$_2$× 2), 3.05 (12H, s, N(CH$_3$)$_2$×2), 1.0–2.0 (34H, m) Elemental analysis (for C$_{40}$H$_{62}$N$_6$O$_2$.2HCl) Calculated (%): C, 65 64; H, 8.81; N 11.48. Found (%): C, 66.02; H, 8.43; N, 11.42.

Example 98

Cis-1,2-bis[[3-(4-dimethylaminophenyl)-1-furfurylureido]methyl]cyclohexane

The title compound was synthesized by the method in accordance with Example 2.

mp: 106°–110° C. (dihydrochloric acid salt) MS(FAB): m/e=627 (M$^+$+1) IR(KBr) ν MAX: 2929(brs), 1656(s), 1646(s), 1517(s) NMR(DMSO-d$_6$) δ: 8.43 (2H, s, NH×2), 7.55 (2H, m, Ar—H), 7.2–7.5 (8H, m, Ar—H), 6.37 (2H, m, Ar—H), 6.30 (2H, d, J=3.0 Hz, Ar—H), 4.5–4.7 (4H, m, NCH$_2$×2), 3.2–3.5 (4H, m, NCH$_2$×2), 3.01 (12H, s, N(CH$_3$)$_2$×2), 1.93 (2H, brs, CH×2), 1.2–1.7 (8H, m) Elemental analysis (for $C_{36}H_{46}N_6O_4 \cdot 2HCl \cdot H_2O$) Calculated (%): C, 60.24; H, 7.02; N, 11.71. Found (%): C, 60.10; H, 7.30; N, 11.55.

Pharmacological Test Examples

Compounds of the present invention were tested for their pharmacological effects by the following methods.

1) Inhibitory effect on ACAT (Acyl-CoA: cholesterol acyltransferase) enzyme (No.1)

Compounds of the invention were tested for their inhibitory effects on ACAT enzyme of rabbit liver microsome by the method of J. G. Heider (J. of Lipid Res., vol. 24, 1127–1134, 1983). More specifically, the test was done by measuring the amount of labelled cholesterol oleate ester produced from oleic acid CoA (coenzyme A) labelled by radiation. Table 1 shows the concentration of each test compound needed to inhibit 50% of the enzyme activity of the control group.

TABLE 9

| Inhibitory effect on ACAT enzyme activity | |
|---|---|
| Example no. of test compound | $IC_{50}(M)$ |
| 7 | $10.0 \times 10^{-8}$ |
| 11 | $4.7 \times 10^{-8}$ |
| 15 | $3.8 \times 10^{-8}$ |
| 28 | $2.5 \times 10^{-8}$ |
| 42 | $6.0 \times 10^{-8}$ |
| 43 | $5.0 \times 10^{-8}$ |
| 61 | $3.6 \times 10^{-8}$ |
| 83 | $4.6 \times 10^{-8}$ |
| YM-17E*[)] | $2.3 \times 10^{-8}$ |

Note: *[)]a compound described in Example 47 of Japanese Unexamined Patent Publication No. 117651/1990

2) Inhibitory effect on ACAT (Acyl-CoA: cholesterol acyltransferase) enzyme (No.2)

[2-1] ACAT enzyme activities of rabbit liver and small intestine mucosa microsomes A white male rabbit was fed with a 12 cholesterol-containing food for four weeks and bleeding-slaughtered to extract its liver and small intestine. Microsomes of the liver and small intestine mucosa were prepared by the method of C. Marco et al. (Biochim. Biophys. Acta, 617, 458–471, 1980).

ACAT enzyme activities of the microsomes were determined by the method of J. G. Heider (J. Lipid Res., 24, 1127–1134, 1983). A test sample dissolved in 1% dimethylsulfoxide was added to a microsome fraction (100 μg), a phosphoric acid buffer (0.154M) having pH 7.4, 1-$^{14}$C-oleoyl CoA (36 μM), dithiosleitol (2 mM) and bovine blood serum albumin (36 μg/ml). The reaction mixture adjusted to a final capacity of 0.5 ml was incubated at 37° C. for 60 minutes. A mixture (6 ml) of chloroform and methanol (2:1) was added and the reaction was stopped. Cholesterol oleate was extracted with chloroform and separated by thin-layer chromatography. ACAT enzyme activities of the microsome fractions were determined by radiation measurement. Table 10 shows the results.

TABLE 10

| Inhibitory effect on ACAT enzyme activity | | |
|---|---|---|
| | $IC_{50}(nM)$ | |
| Example no. of test compound | Liver of rabbit | Small intestine of rabbit |
| 12 | 36 | 24 |
| 13 | 35 | 130 |
| 22 | 83 | 18 |
| 28 | 42 | 30 |
| 14-1 | 180 | 140 |
| 14-2 | 62 | 52 |
| 12-1 | 78 | 29 |
| YM-17E*[)] | 23 | — |

Note: *[)]a compound described in Example 47 of Japanese Unexamined Patent Publication No. 117651/1990

[2-2] ACAT enzyme activities of human HepG2 and CaCo2 cells

Human HepG2 and CaCo2 cells purchased from ATCC (AMERICAN TYPE CULTURE COLLECTION) were used in this test.

Using RPMI 1640 medium for HepG2 and DMEM medium for CaCo2, HepG2 and CaCo2 cells were cultured with 40 ml of each medium containing 10% bovine blood serum, 50 I.U. of penicillin and 50 μg/ml of streptomycin in a 5% $CO_2$ incubator at 37° C. The cells were then monolayer-cultured with 80 ml of each medium containing 10 pg/ml of cholesterol and 5 μg/ml of 25-OH cholesterol in a 175 cm flask for 5 hours. The homogenizes of these cells were subjected to centrifugation at 105,000 g to collect microsome fractions. ACAT enzyme activities of the microsome fractions were determined by the above-mentioned method. Table 11 shows the results.

TABLE 11

| Inhibitory effect on ACAT enzyme activity | | |
|---|---|---|
| Example No. | $IC_{50}(nM)$ | |
| of test compound | Human HepG2 | Human CaCo2 |
| 12 | 1.1 | 0.74 |
| 13 | 0.86 | 1.1 |
| 22 | 0.32 | 0.22 |
| 28 | 1.2 | 0.52 |
| 14-1 | 0.40 | 0.80 |
| 14-2 | 0.27 | 1.6 |
| 12-1 | 1.5 | 1.5 |
| YM-17E*[)] | 9.6 | 14 |

*[)]a compound described in Example 47 of Japanese Unexamined Patent Publication No. 117651/1990

3) Cholesterol Lowering Effect

[3-1] Using a rat having high cholesterol, compounds of the invention were tested for their serum cholesterol lowering effects by the following method. A 6-week-old SD-type (Sprague-Dawley) male rat was fed with food containing 1% of cholesterol, 0.5% of cholic acid and 5% of olive oil for 2 days and then orally administered the food and a compound of the invention as dissolved in saline once a day for 5 days starting on day 3. Four hours after the final administration, a blood sample was taken. The total cholesterol in the serum of the test group was measured and compared with that of the control group. Table 2 shows what percentage of the cholesterol in the serum of the control group was reduced by means of the test compound.

TABLE 12

| | Cholesterol lowering effect | |
|---|---|---|
| Example no. of test compound | % 10 mg/kg | % 3 mg/kg |
| 7 | 103 | 105 |
| 11 | 101 | 108 |
| 15 | 99 | 93 |
| 28 | 100 | 106 |
| 42 | 102 | 110 |
| 43 | 107 | 88 |
| 61 | 82 | 48 |
| 83 | 91 | 43 |
| YM-17E*) | 91 | 38 |

*)a compound described in Example 47 of Japanese Unexamined Patent Publication No. 117651/1990

As clear from the above, the compounds of the present invention can inhibit ACAT enzyme activities of the experimental systems in vitro or in vivo.

[3-2] Using a rat having high cholesterol, compounds of the invention were tested for their serum cholesterol lowering effects by the following method. A 6-week-old SD-type (Sprague-Dawley) male rat was fed with food containing 1% of cholesterol, 0.5% of cholic acid and 5% of olive oil for 7 days. For the last 5 days, a test sample suspended in some drops of Tween 80 and saline was orally administered once a day. Four hours after the final administration, a blood sample was taken from celiac aorta of the rat under etherization. The total cholesterol in the serum of the test group was measured by the oxygen method and compared with that of the control group. Table 13 shows what percentage of the cholesterol of the serum of the control group was reduced by means of the test compound.

TABLE 13

| | Cholesterol lowering effect | |
|---|---|---|
| Example No. of test compound | % 3 mg/kg | % 1 mg/kg |
| 12 | 92.6 | 96.2 |
| 13 | 96.2 | 76.8 |
| 22 | 97.2 | 77.6 |
| 28 | 106.5 | 70.2 |
| 14-1 | 96.2 | 80.9 |
| 14-4 | 98.8 | 79.9 |
| 12-1 | 108.3 | 100.4 |
| YM-17E*) | 38.0 | — |

*)a compound described in Example 47 of Japanese Unexamined Patent Publication No. 117651/1990

What is claimed is:

1. A cyclohexanediurea derivative represented by the following formula (I):

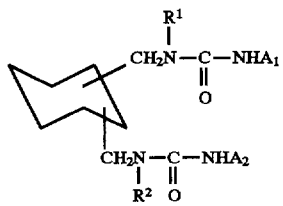

wherein $R^1$ and $R^2$ are the same or different and they each represent a straight-chain or branched alkyl group having at least 3 carbons, a cycloalkyl group, a cycloalkyl group having a bridge head, a furyl group, a furyl lower alkyl group or an aralkyl group, $A_1$ and $A_2$ are the same or different and they each represent a phenyl, pyridyl, quinolyl, isoquinolyl or indolyl group which may have a substituent; or a salt thereof.

2. A cyclohexanediurea derivative according to claim 1 wherein $R^1=R^2$ and $A_1=A_2$; or a salt thereof.

3. A cyclohexanediurea derivative according to claim 1 wherein the urea derivative is linked to the cyclohexane ring by a trans-1,4, cis-1,4 or cis-1,3 bond, $R^1$ and $R^2$ are the same or different and they each represent a cycloalkyl group or a branched alkyl group, and $A_1$ and $A_2$ represent 4-dimethylaminophenyl, 4-pyrrolidinophenyl or 4-piperidinophenyl; or a salt thereof.

4. A cyclohexanediurea derivative according to claim 1 wherein $R^1$ and $R^2$ are the same or different and they each represent cyclopentyl, cyclohexyl, cyclobutyl or 4-methylcyclohexyl; or a salt thereof.

5. A cyclohexanediurea derivative according to claim 1 wherein $A_1$ and $A_2$ are the same or different and they each represent 4-dimethylaminophenyl, 4-diethylaminophenyl, 4-pyrrolidinophenyl, 4-piperidinophenyl, or 4-morpholynophenyl; or a salt thereof.

6. A cyclohexanediurea derivative or a salt thereof which is one of the compounds or salts given below in (1)–(10):

(1) a trans-1,4-bis[[1-cyclopentyl-3-(4-dimethylaminophenyl)ureido]methyl]cyclohexane or a salt thereof;

(2) a trans-1,4-bis[[1-cyclohexyl-3-(4-dimethylaminophenyl)ureido]methyl]cyclohexane or a salt thereof;

(3) a trans-1,4-bis[[1-cyclohexyl-3-(4-diethylaminophenyl)ureido]methyl]cyclohexane or a salt thereof;

(4) a trans-1,4-bis[[1-cyclohexyl-3-(4-pyrrolidinophenyl)ureido]methyl]cyclohexane or a salt thereof;

(5) a trans-1,4-bis[[1-cyclohexyl-3-(4-piperidinophenyl)ureido]methyl]cyclohexane or a salt thereof;

(6) a trans-1,4-bis[[3-(4-dimethylaminophenyl)-1-(4-methylcyclohexyl)ureido]methyl]cyclohexane or a salt thereof;

(7) a trans-1,4-bis[[1-cycloheptyl-3-(4-dimethylaminophenyl)ureido]methyl]cyclohexane or a salt thereof;

(8) a trans-1,4-bis[[1-cycloheptyl-3-(4-diethylaminophenyl)ureido]methyl]cyclohexane or a salt thereof;

(9) a trans-1,4-bis[[1-cycloheptyl-3-(4-pyrrolidinophenyl)ureido]methyl]cyclohexane or a salt thereof; and

(10) a trans-1,4-bis[[1-cycloheptyl-3-(4-piperidinophenyl)ureido]methyl]cyclohexane.

7. A cyclohexanediamine derivative represented by the following formula (II):

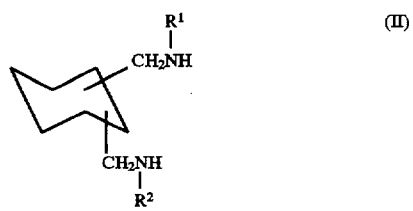

wherein $R^1$ and $R^2$ are the same or different and each represent a member selected from the group consisting of a straight chain or branched alkyl group having at least three carbons, a cycloalkyl group, a cycloalkyl group having a bridge head, a furyl group, and a furyl lower alkyl group; or a salt thereof.

8. A cyclohexanediamine derivative according to claim 7 wherein $R^1=R^2$; or a salt thereof.

9. A pharmaceutical composition for inhibiting an ACAT enzyme comprising an effective amount of the cyclohexanediurea derivative or its salt defined in claim 1 and a pharmaceutically acceptable carrier.

10. A pharmaceutical composition for hyperlipidemia which comprises an effective amount of the cyclohexanediurea derivative or its salt defined in claim 1 and a pharmaceutically acceptable carrier.

11. A pharmaceutical composition for atherosclerosis which comprises an effective amount of the cyclohexanediurea derivative or its salt defined in claim 1 and a pharmaceutically acceptable carrier.

12. A method for inhibiting ACAT (Acyl-CoA: cholesterol acyltransferase) enzyme which comprises administering to a patient an effective amount of the cyclohexanediurea derivative or its salt defined in claim 1.

13. A method for treating hyperlipidemia which comprises administering to a patient an effective amount of the cyclohexanediurea derivative or its salt defined in claim 1.

14. A method for treating atherosclerosis which comprises administering to a patient an effective amount of the cyclohexanediurea derivative or its salt defined in claim 1.

15. A method for producing a cyclohexanediurea derivative represented by the following formula (I):

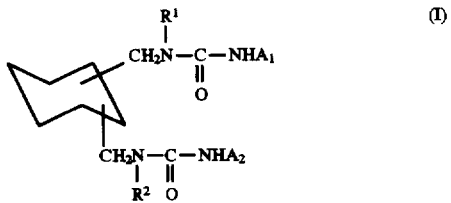

wherein $R^1$ and $R^2$ are the same or different and they each represent a straight-chain or branched alkyl group having at least 3 carbons, a cycloalkyl group, a cycloalkyl group having a bridge head, a furyl group, a furyl lower alkyl group or an aralkyl group, $A_1$ and $A_2$ are the same or different and they each represent a phenyl, pyridyl, quinolyl, isoquinolyl or indolyl group which may have substituents, by one of the following processes A–D:

<Process A>

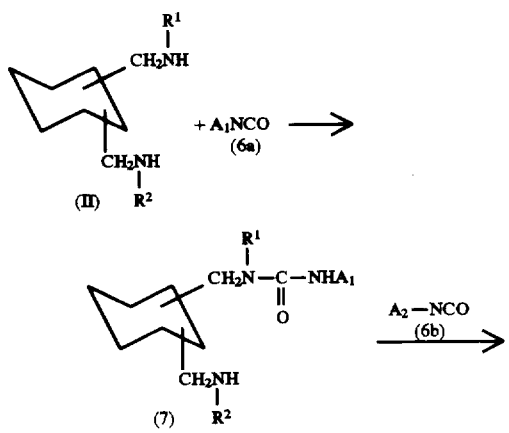

-continued

<Process A>

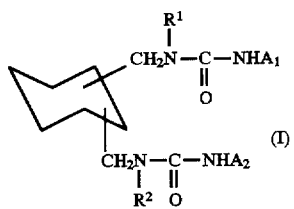

wherein $R^1$, $R^2$, $A_1$ and $A_2$ are as defined above,

<Process B>

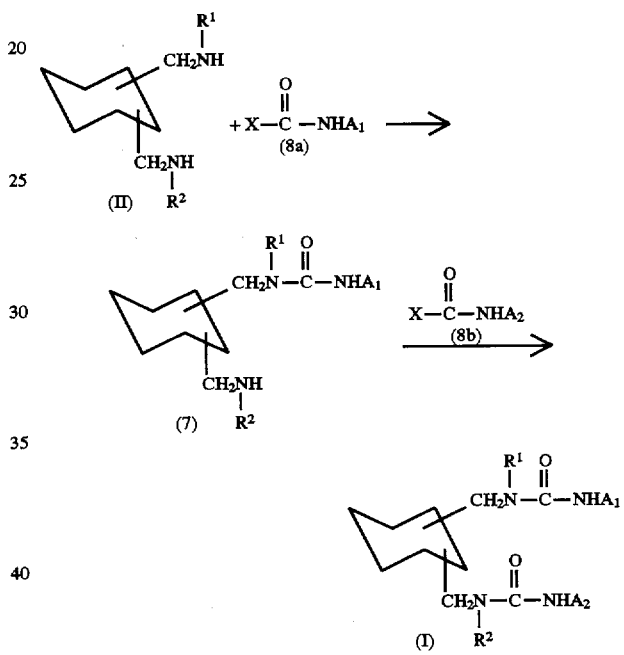

wherein $R^1$, $R^2$, $A_1$ and $A_2$ are as defined above,

<Process C>

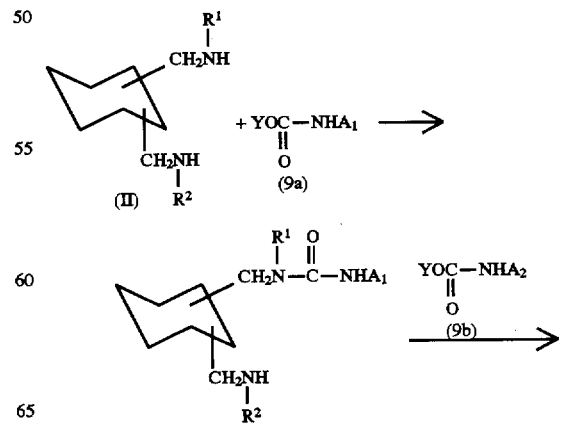

-continued
<Process C>
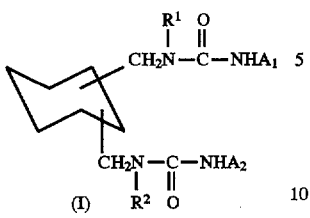
wherein $R^1$, $R^2$, $A_1$ and $A_2$ are as defined above, and
<Process D>
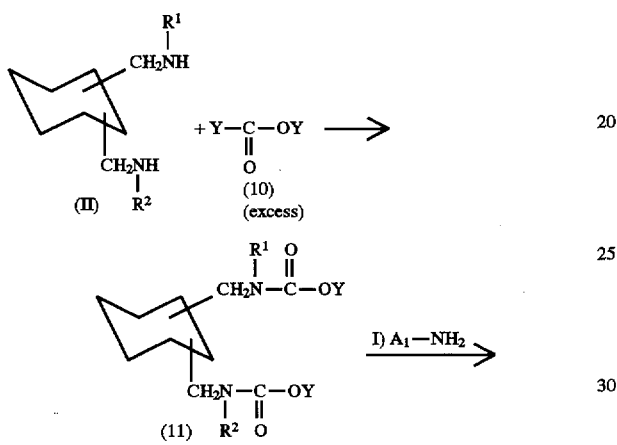
-continued
<Process D>
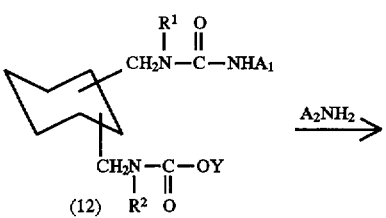
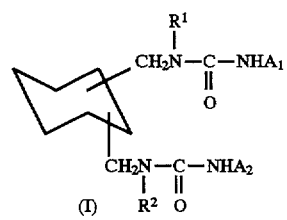
wherein $R^1$, $R^2$, $A_1$ and $A_2$ are as defined above.
* * * * *